US010253315B2

(12) United States Patent
Bruniaux et al.

(10) Patent No.: US 10,253,315 B2
(45) Date of Patent: Apr. 9, 2019

(54) METHOD FOR TRANSFECTION OF NUCLEIC ACIDS INTO EUKARYOTIC CELLS IN 3D SCAFFOLD

(71) Applicant: Commissariat à l'énergie atomique et aux énergies alternatives, Paris (FR)

(72) Inventors: Jonathan Bruniaux, Tours (FR); Xavier Gidrol, Saint Paul de Vence (FR); Fabrice Navarro Y Garcia, Fontaine (FR); Eric Sulpice, Biviers (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 679 days.

(21) Appl. No.: 14/556,751

(22) Filed: Dec. 1, 2014

(65) Prior Publication Data
US 2015/0159153 A1 Jun. 11, 2015

Related U.S. Application Data

(63) Continuation-in-part of application No. PCT/EP2013/066821, filed on Aug. 12, 2013, and a continuation-in-part of application No. PCT/EP2013/075279, filed on Dec. 2, 2013.

(30) Foreign Application Priority Data

Aug. 30, 2012 (FR) .................................. 12 58115
Nov. 30, 2012 (FR) .................................. 12 61520

(51) Int. Cl.
*C12N 15/10* (2006.01)
*C12N 5/071* (2010.01)
*C12N 15/64* (2006.01)
*C12Q 1/68* (2018.01)
*C12N 5/09* (2010.01)
*C12N 15/87* (2006.01)
*B82Y 5/00* (2011.01)

(52) U.S. Cl.
CPC ....... *C12N 15/1065* (2013.01); *C12N 5/0683* (2013.01); *C12N 5/0693* (2013.01); *C12N 15/64* (2013.01); *C12N 15/87* (2013.01); *B82Y 5/00* (2013.01); *C12N 2510/00* (2013.01); *C12N 2513/00* (2013.01)

(58) Field of Classification Search
CPC .......................... C12N 15/1056; C12N 5/0683
See application file for complete search history.

(56) References Cited

U.S. PATENT DOCUMENTS 9,080,186 B2   7/2015  Cui et al.
2009/0221684 A1  9/2009  Grinstaff et al.

2011/0201695 A1   8/2011  Mourier-Robert et al.
2012/0156251 A1   6/2012  Brito et al.
2012/0289584 A1  11/2012  Cui et al.

FOREIGN PATENT DOCUMENTS

WO   WO2009/031911    *  3/2009
WO   WO2010018223       2/2010
WO   WO-2012/019765     2/2012

OTHER PUBLICATIONS

Dalesandro et al. et al. (The Journal of Thoracic and Cardiovascular Surgery. 1996; 111(2): 416-422).*
Marler et al. (Advanced Drug Delivery Reviews. 1998; 33: 165-182).*
Gerrits et al. (Blood. 2010; 115(13): 2610-2618).*
Romberg et al. (Pharmaceutical Research. Jan. 2008; 25(1): 55-71) (Year: 2008).*
International Search Report and Written Opinion dated Jan. 3, 2014 in PCT/EP2013/075279.
International Search Report and Written Opinion dated Oct. 1, 2013 in PCT/EP2013/066821.
Berns, K., et al., "A large-scale RNAi screen in human cells identifies new components of the p53 pathway", Mar. 25, 2004, pp. 431-437, vol. 428, Nature: International Weekly Journal of Science (and Supplementary Information), Nature Publishing Group, United Kingdom.
Xian-Zhu, Yang, et al., "Systemic delivery of siRNA with cationic lipid assisted PEG-PLA nanoparticles for cáncer therapy", Jul. 26, 2011, pp. 203-211, vol. 156, No. 2, Journal of Controlled Release, Elsevier, Amsterdam, NL.
Santel, A, et al., "A novel siRNA-lipoplex technology for RNA interference in the mouse vascular endothelium", Apr. 20, 2006, pp. 1222-1234, vol. 13, No. 16, Gene Therapy, Nature Publishing Group, GB.
Gerrits, et al., "Cellular barcoding tool for clonal analysis in the hematopoietic system", Apr. 1, 2010, pp. 2610-2618, vol. 115, No. 13, Blood.
Dalesandro, et al, "Gene Therapy for Donor Hearts: Ex Vivo Liposome-Mediated Transfection", Feb. 1996, pp. 416-422, vol. 111, No. 2, The Journal of Thoracic and Cardiovascular Surgery.
Chono, et al., An efficient and low immunostimulatory nanoparticle formulation for system siRNA delivery to the tumor, 2008, pp. 64-69, vol. 131, Journal of Controlled Release.

(Continued)

*Primary Examiner* — Scott Long
(74) *Attorney, Agent, or Firm* — B. Aaron Schulman, Esq.; Stites & Harbison, PLLC

(57) ABSTRACT

The present invention concerns a method for in vitro or ex vivo transfection of a nucleic acid into a eukaryotic cell in 3D scaffold by contacting eukaryotic cells in 3D scaffold with a formulation in nanoemulsion form which comprises a continuous aqueous phase and a least one dispersed phase, and which comprises said nucleic acid. The invention further relates to a method of screening implementing said method of transfection, and to 3D scaffold comprising eukaryotic cells and said formulation in nanoemulsion form which comprises a continuous aqueous phase and a least one dispersed phase, and which comprises said nucleic acid.

16 Claims, 18 Drawing Sheets

(56) References Cited

OTHER PUBLICATIONS

Cui, et al., "Topical immunization using nanoengineered genetic vaccines", 2002, pp. 173-184, vol. 81, Journal of Controlled Release.
Marler, et al., "Transplantation of cells in matrices for tissue regeneration", 1998, pp. 165-182, vol. 33, Advanced Drug Delivery Reviews.
Gerrits, et al., "Cellular barcoding tool for clonal analysis in the hematopoietic system", Apr. 1, 2010, pp. 2610-2618, vo.. 115, No. 13, Blood.
Teixeira, et al., "Submicron Cationic Emulsions as a New Delivery System for Oligonucleotides", 1999, pp. 30-36, vol. 16, No. 1, Pharmaceutical Research.
Verzijlbergen, "A Barcode Screen for Epigenetic Regulators Reveals Role for the NuB4/HAT-B Histone Acetyltransferase Complex in Histone Turnover", Oct. 2011, pp. 1-15, vol. 7, No. 10, PLoS Genetics.

\* cited by examiner

M: molecular weight marker
1: 11/20
2: 5.5/10
3: 2.75/5
4: 1.37/2.5
5: 0.68/1.25
6: 0.34/0.62
7: 0.17/0.31
} ng siRNA / ng DNA tag used for complexation with nanoparticles 8: siRNA (0.17ng) without nanoparticles
9: DNA tag (0.31ng) without nanoparticles (From Brendon M. Baker and Christopher S. Chen. J Cell Sci. Jul 1, 2012; 125(13): 3015–3024).

METHOD FOR TRANSFECTION OF NUCLEIC ACIDS INTO EUKARYOTIC CELLS IN 3D SCAFFOLD

CROSS-REFERENCE TO RELATED APPLICATIONS

This application is a Continuation-In-Part of international patent applications PCT/EP2013/075279, filed Dec. 2, 2013, and PCT/EP2013/066821, filed Aug. 12, 2013, both of said applications hereby incorporated by reference in their entirety.

FIELD OF THE INVENTION

The present invention concerns a method for in vitro or ex vivo transfection of a nucleic acid into a eukaryotic cell in 3D scaffold by contacting eukaryotic cells in 3D scaffold with a formulation in nanoemulsion form which comprises a continuous aqueous phase and a least one dispersed phase, and which comprises said nucleic acid. The invention further relates to a method of screening implementing said method of transfection, and to 3D scaffold comprising eukaryotic cells and said formulation in nanoemulsion form which comprises a continuous aqueous phase and a least one dispersed phase, and which comprises said nucleic acid.

BACKGROUND OF THE INVENTION

Cells growing in tissues are in a three dimensional environment with biophysical and biomechanical characteristics signals. These signals influence major cellular functions such as migration, adhesion, proliferation and gene expression.

However, most in vitro tests performed in the laboratory focus on a cell culture in two dimensions, easier to implement. In this manner, the cells are grown on plastic polystyrene dishes which are very stiff and unnatural. Adhesion of these cells on these synthetic structures is done by adhesions different from what can be found in vivo (FIG. 1). Indeed, the cell undergoes many constraints to spread and migrate in xy. The microenvironment of the cell is neglected and thus the results can give interpretations that do not correspond to what can be found in the tissues.

For about thirty years, a three-dimensional cell culture has been developing to more accurately mimic the physiology of natural tissues and organs. By this way, the cells bind to each other formants physical cell to cell bonds (FIG. 2). In addition, the material used to allow the natural three-dimensional development is malleable as natural tissues, and comprised of complex proteins in their native configuration thereby providing important biological instructions for cells. In this environment, cells can exert forces on each other by their interactions stimulating creating gap junction, by ion exchange, or even by electrical currents. These special links provide more complex phenotypes and closer to native tissues cellular functions by enhanced communication and signaling.

Two advantages are obvious for the study of pathological conditions in vitro, particularly in the search for biomarkers and new therapeutic targets and drug tests. First, the cells do not have the same response to treatment: for example, breast cancer cells grown in 2D can be easily killed by low doses of chemotherapeutic drugs and low doses of radiation. These same cells in 3D with the same doses of drug or radiation are more resistant, like cancer in vivo. Validation is therefore more accurate and representative of the actual physiology through three-dimensional tests. Second, unlike the 2D culture where cells form a very thin monolayer on the plastic surface, 3D culture show a series of cell layers. The need to diffuse through to reach the deepest cells is important. This is paramount in choosing the ideal vehicle for the desired application. Studies are also underway, including for drug delivery in this type of structure.

The development of high-throughput screening in 3D culture is proving to be an important next step in research through RNAi. Its use will allow being closer to the physiological conditions and avoiding false positives and/or false negatives inherent to the difference in environment of cells cultivated in petri dish.

To this end, products helping in the transfection of nucleic acids into eukaryotic cells in 3D scaffold are needed.

SUMMARY OF THE INVENTION

The invention relates to a method for in vitro or ex vivo transfection of a nucleic acid into a eukaryotic cell in 3D scaffold, said method comprising the steps of:
  a) providing eukaryotic cells in 3D scaffold;
  b) contacting the eukaryotic cells in 3D scaffold with at least one formulation in nanoemulsion form, under conditions sufficient to allow a nucleic acid and which is contained in said formulation in nanoemulsion form to transfect the eukaryotic cells in 3D scaffold,
  wherein said at least one formulation in nanoemulsion form comprises a continuous aqueous phase and a least one dispersed phase, and comprises:
    i) at least 5 mole % of amphiphilic lipid;
    ii) 15 to 70 mole % of at least one cationic surfactant comprising:
      ii-1) at least one lipophilic group selected from the group consisting of:
        an R or R—(C=O)— group, where R is a linear hydrocarbon chain having 11 to 23 carbon atoms,
        an ester or amide of fatty acids having 12 to 24 carbon atoms and phosphatidylethanolamine, and
        a poly(propylene oxide), and
      ii-2) at least one hydrophilic group comprising at least one cationic group selected from the group consisting of:
        a linear or branched alkyl group having 1 to 12 carbon atoms and interrupted and/or substituted by at least one cationic group; and
        a hydrophilic polymeric group comprising at least one cationic group; and
    vi) 10% to 55 mole % of a co-surfactant comprising at least one poly(ethylene oxide) chain comprising at least 25 ethylene oxide units;
    vii) a solubilising lipid; and
    viii) said nucleic acid;
  wherein the mole percentages of amphiphilic lipid, cationic surfactant and co-surfactant are relative to the whole (amphiphilic lipid/cationic surfactant/co-surfactant/optional helper lipid).

The invention also relates to a method of screening for a nucleic acid of interest, which method comprises the steps consisting of:
  a) providing eukaryotic cells in 3D scaffold;
  b) contacting the eukaryotic cells in 3D scaffold with at least one formulation in nanoemulsion form, under conditions sufficient to allow a candidate nucleic acid and which is contained in said formulation in nanoemulsion form to transfect the eukaryotic cells in 3D scaffold, wherein said at least one formulation in nanoemulsion form comprises a continuous aqueous phase and a least one dispersed phase, and comprises:
  i) at least 5 mole % of amphiphilic lipid;
  ii) 15 to 70 mole % of at least one cationic surfactant comprising:
    ii-1) at least one lipophilic group selected from the group consisting of:
      an R or R—(C=O)— group, where R is a linear hydrocarbon chain having 11 to 23 carbon atoms,
      an ester or amide of fatty acids having 12 to 24 carbon atoms and phosphatidylethanolamine, and
      a poly(propylene oxide), and
    ii-2) at least one hydrophilic group comprising at least one cationic group selected from the group consisting of:
      a linear or branched alkyl group having 1 to 12 carbon atoms and interrupted and/or substituted by at least one cationic group; and
      a hydrophilic polymeric group comprising at least one cationic group; and
  vi) 10% to 55 mole % of a co-surfactant comprising at least one poly(ethylene oxide) chain comprising at least 25 ethylene oxide units;
  vii) a solubilising lipid; and
  viii) said candidate nucleic acid;
wherein the mole percentages of amphiphilic lipid, cationic surfactant and co-surfactant are relative to the whole (amphiphilic lipid/cationic surfactant/co-surfactant/optional helper lipid);
  c) detecting if the eukaryotic cells in 3D scaffold contacted with said at least one formulation in nanoemulsion form display a phenotype of interest; and
  d) identifying the candidate nucleic acid as a sequence of interest if a phenotype of interest has been detected, or identifying the candidate nucleic acid as a sequence of no interest if a phenotype of interest has not been detected.

According to another aspect of the invention, it is provided an in vitro or ex vivo 3D scaffold comprising:
  a three-dimensional scaffold;
  eukaryotic cells; and
  at least one formulation in nanoemulsion form comprising
    a continuous aqueous phase and a least one dispersed phase, and which comprises:
    i) at least 5 mole % of amphiphilic lipid;
    ii) 15 to 70 mole % of at least one cationic surfactant comprising:
      ii-1) at least one lipophilic group selected from the group consisting of:
        an R or R—(C=O)— group, where R is a linear hydrocarbon chain having 11 to 23 carbon atoms,
        an ester or amide of fatty acids having 12 to 24 carbon atoms and phosphatidylethanolamine, and
        a poly(propylene oxide), and
      ii-2) at least one hydrophilic group comprising at least one cationic group selected from the group consisting of:
        a linear or branched alkyl group having 1 to 12 carbon atoms and interrupted and/or substituted by at least one cationic group; and
        a hydrophilic polymeric group comprising at least one cationic group; and
    vi) 10% to 55 mole % of a co-surfactant comprising at least one poly(ethylene oxide) chain comprising at least 25 ethylene oxide units;
    vii) a solubilising lipid; and
    viii) a nucleic acid;
wherein the mole percentages of amphiphilic lipid, cationic surfactant and co-surfactant are relative to the whole (amphiphilic lipid/cationic surfactant/co-surfactant/optional helper lipid).

According to an embodiment of said methods and said in vitro or ex vivo 3D scaffold comprising eukaryotic cells, said at least one formulation in nanoemulsion form is a plurality of formulations in nanoemulsion form, each formulation in nanoemulsion form comprising:
  a different nucleic acid (intended to be transfected),
  a tracer and
  a single DNA tag specific to said nucleic acid (intended to be transfected),
thereby forming a library of formulations in nanoemulsion form containing a nucleic acid.

with formulation B10 and a ratio between amount of positive charges due to the cationic surfactant in the «premix» formulation and amount of negative charges provided by the siRNA of 8:1 (quantitative complexing), with lipofectamine (comparative example) (incomplete complexing).

Figure 6:
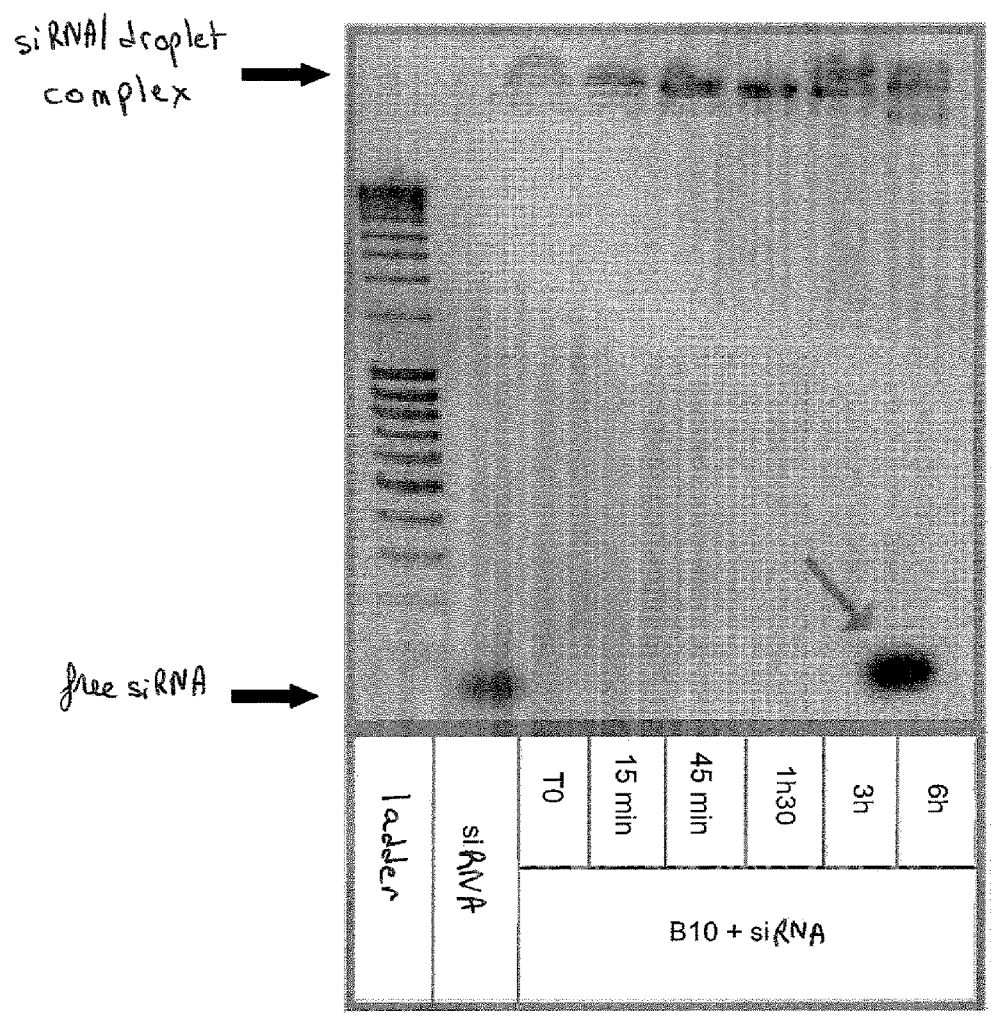

FIG. 6 shows an electrophoresis gel after UV detection of a siRNA/B10 formulation complex just after complexing (T0) then 15 min, 45 min, 1 h30, 3 h and 6 h after complexing. The scale and siRNA (reference) are on the left.

Figure 7:
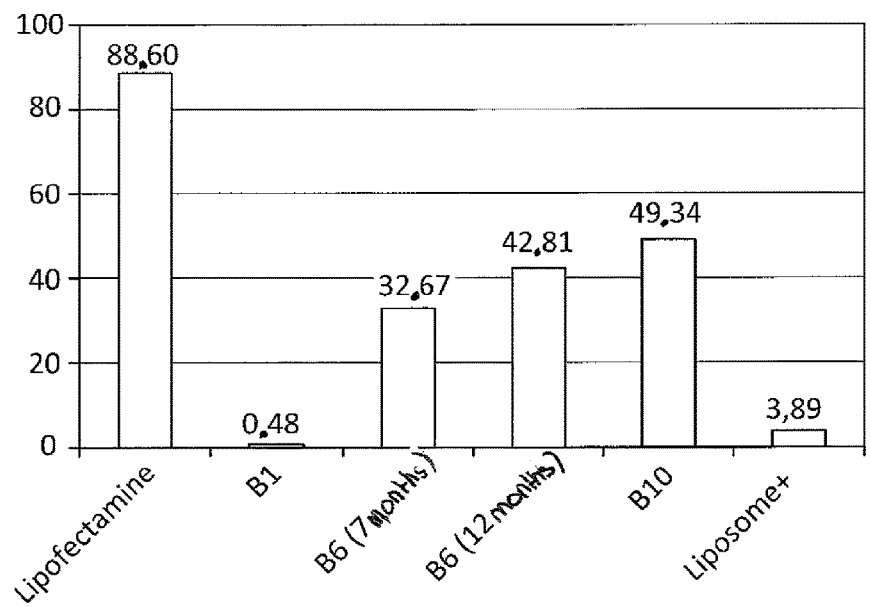

FIG. 7 gives the decrease in FITC fluorescence intensity as a % when transfecting the cell lines with:
Lipofectamine RNAimax (commercial agent);
siRNA/formulation B1 complex;
siRNA/formulation B6 complex, the formulation having been stored for 7 months at ambient temperature prior to complexing;
siRNA/formulation B6 complex, the formulation having been stored for 12 months at ambient temperature prior to complexing;
siRNA/formulation B10 complex, the formulation having been stored for 12 months at ambient temperature prior to complexing;
complex of siRNA/formulation of cationic liposomes comprising DOTAP (58 wt. %), DOPE (18 wt. %), cholesterol (2 wt. %) and DSPE-PEG3000 (22 wt. %)) (comparative).

Figure 8:
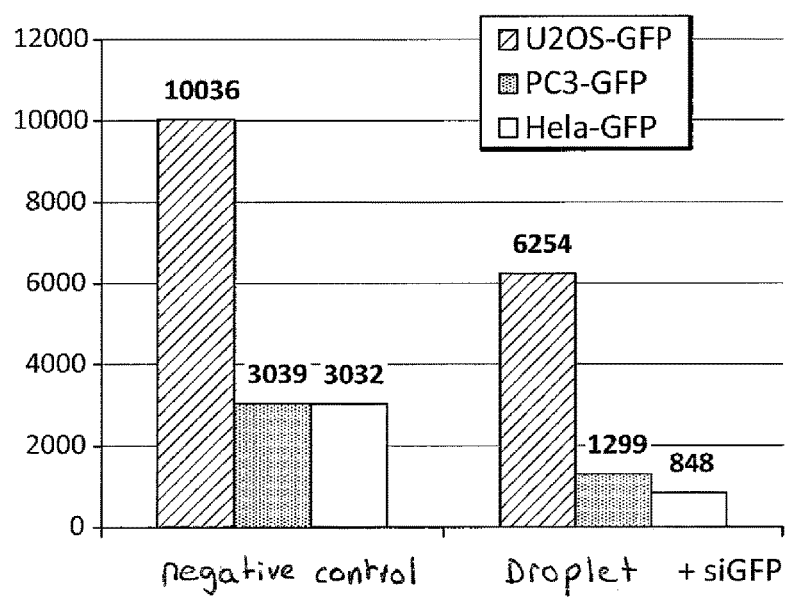

FIG. 8 gives the fluorescence intensity (FITC) for 3 cell lines experimentally overexpressing the fluorescent protein GFP (green fluorescent protein): U2OS, PC3 and Hela for the siRNA/formulation B10 complex, the siRNA called siGFP being targeted against the mRNA encoding the GFP protein, and for the negative reference (cells incubated with a B10 formulation complexed with a negative reference siRNA i.e. «inert» without effect on the transcriptome of the cell called siAllStar).

Figure 9:
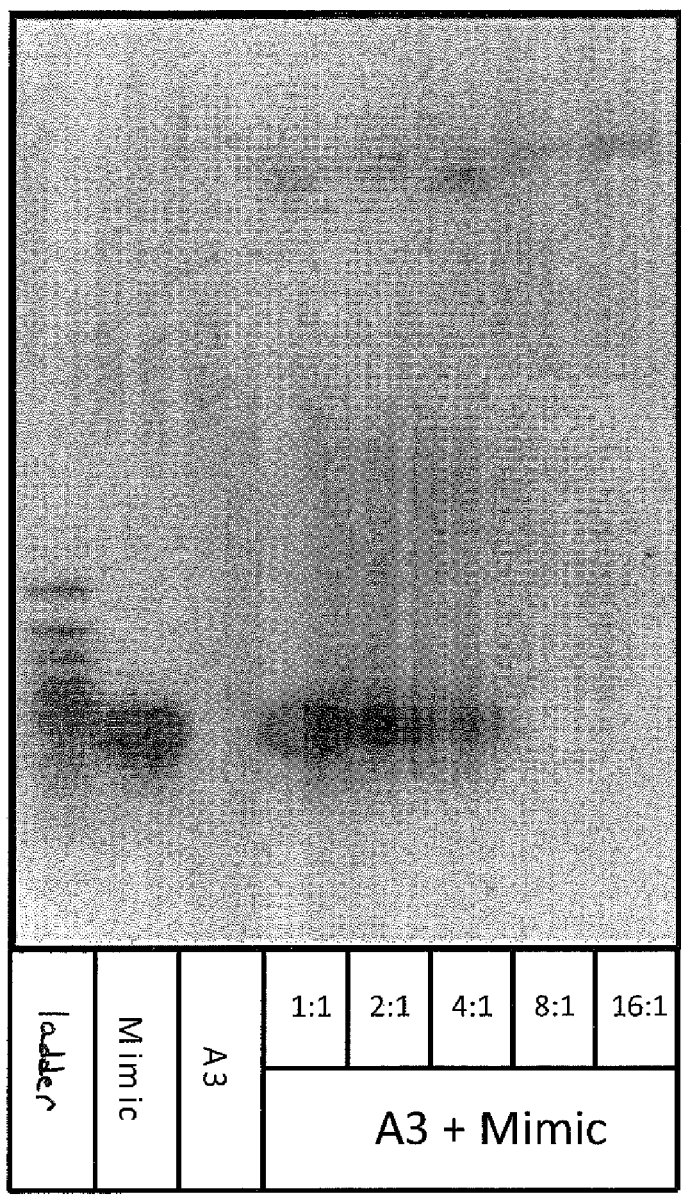

FIG. 9 shows an electrophoresis gel with UV detection after complexing of synthetic microRNA of mimic type with the A3 formulation at the concentrations specified in Table 9. The scale and the microRNA Mimic (reference) and the non-complexed A3 premix formulation are on the left. The final formulations derived from complexing the A3 premix formulation and the Mimics with five different N/P ratios are given on the right.

Figure 10:
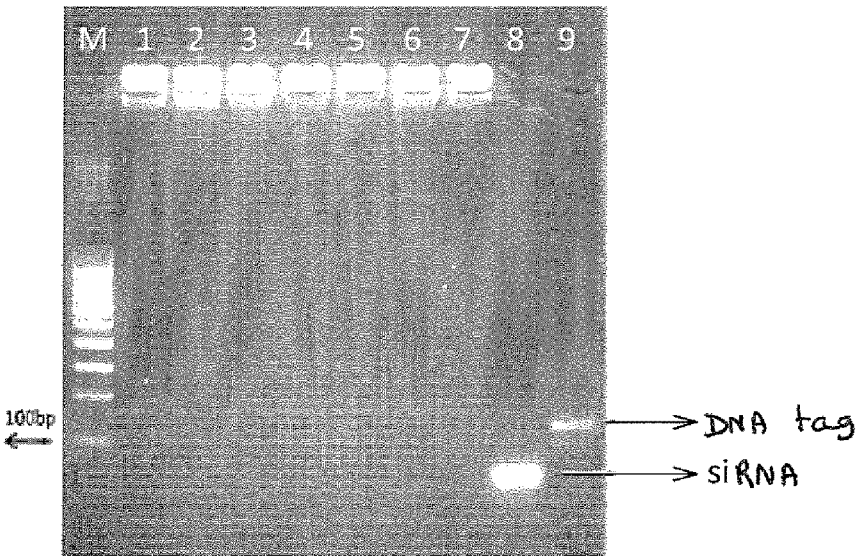

FIG. 10 illustrates an electrophoresis gel revealing the nanoparticles A3/DNA tag/siRNA complexes. The nucleic acids are revealed by means of the reagent, GelRed Nucleic Acid Gel Stain (Interchim, Ref. BY1740)

Figure 11:
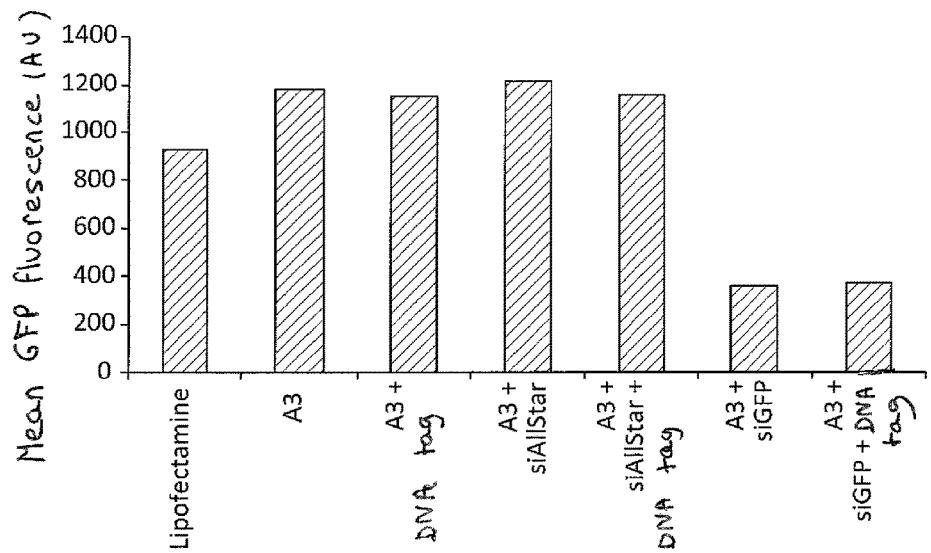

FIG. 11 illustrates the quantification of the averages of fluorescence for GFP after FACS analysis of the HeLa cells and incubated for 72 h with nanoparticles A3/DNA tag/siGFP complexes.

Figure 12:
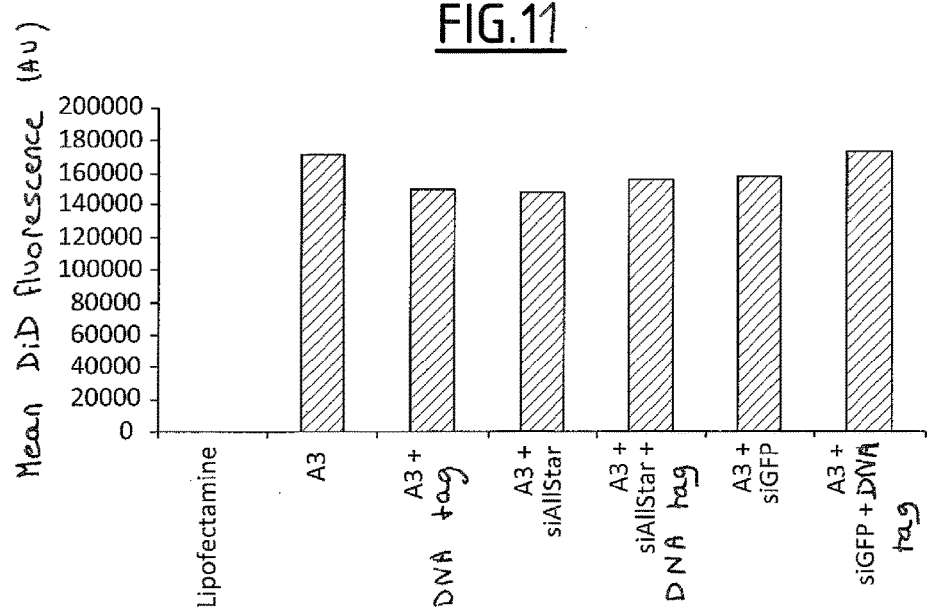

FIG. 12 illustrates the quantification of averages of fluorescence for the encapsulated DID fluorophore after FACS analysis of the HeLa cells and incubated for 72 h with nanoparticles A3/DNA tag/siGFP complexes.

Figure 13:
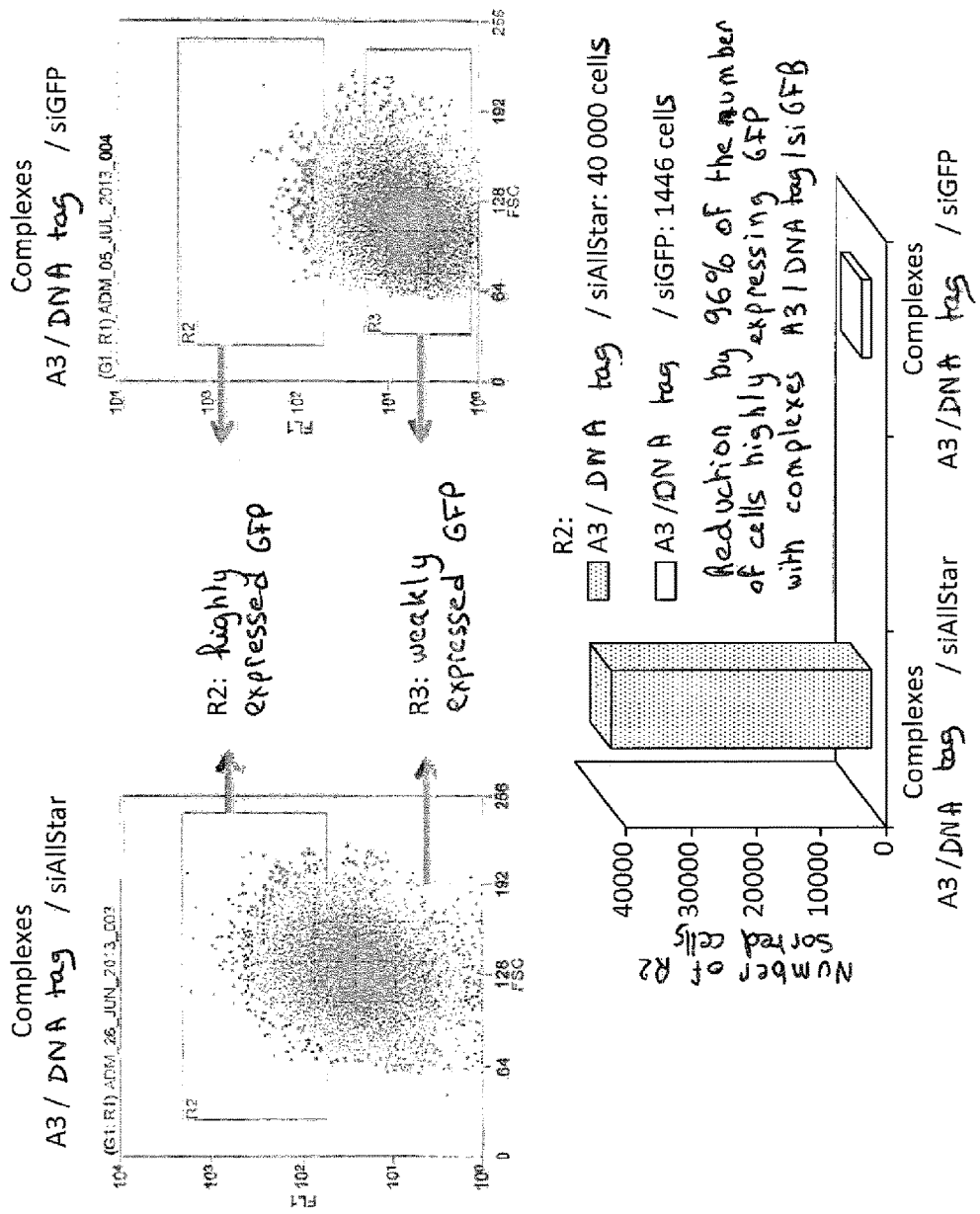

FIG. 13 illustrates the FACS analysis of the FITC signal corresponding to expression of GFP by the HeLa cells. The sorting of these cells was accomplished according to their criterion of expression of GFP and allows identification of two populations: a population which strongly expresses GFP and a population which weakly expresses GFP.

Figure 14:
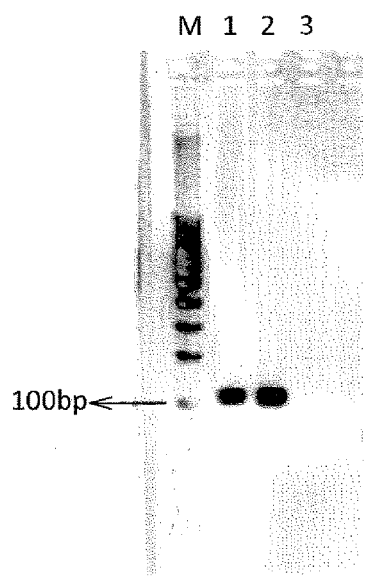

FIG. 14 illustrates an electrophoresis gel of the DNA tags after extraction and amplification with PCR on HeLa cells sorted beforehand.

Figure 15:
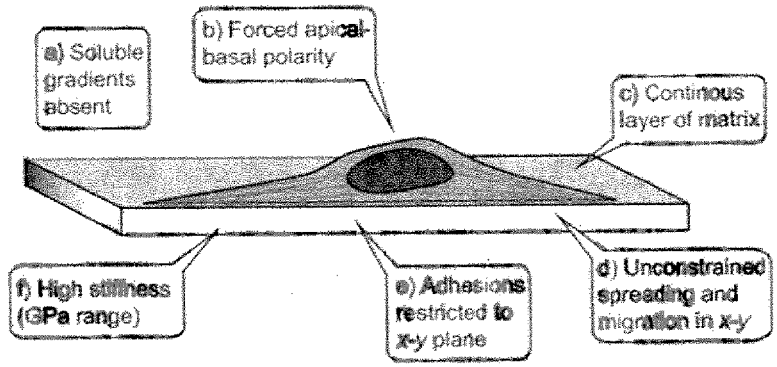
Figure 15:
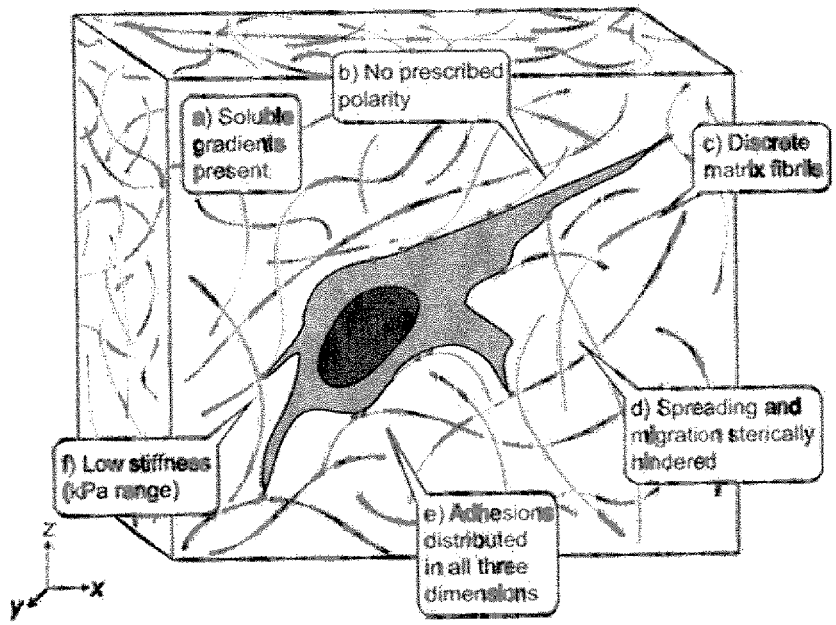

FIG. 15: Stress difference on cells between the 2D culture and 3D cells: cells grown on petri dish undergo adhesion, migration and polarity constraints, whereas cells grown in Matrigel® are representative of physiological conditions.

Figure 16:
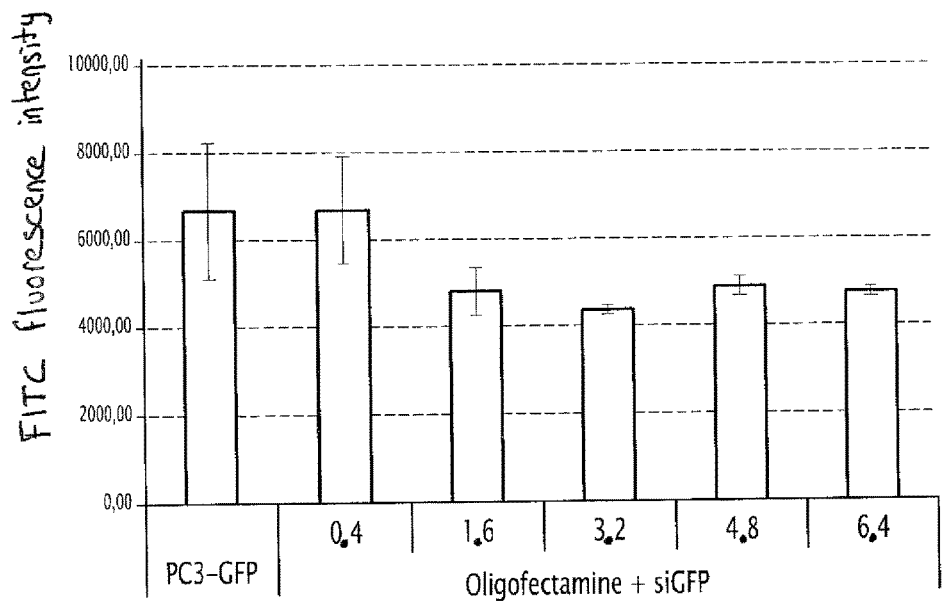

FIG. 16: FITC fluorescence intensity (expression of GFP protein) after siGFP transfection with Oligofectamine™. The figure shows the mean fluorescence intensity obtained by flow cytometry, each point representing the mean value of triplicate, each tube containing 10,000 cells. Untransfected PC3-GFP cells are used as control.

Figure 17:
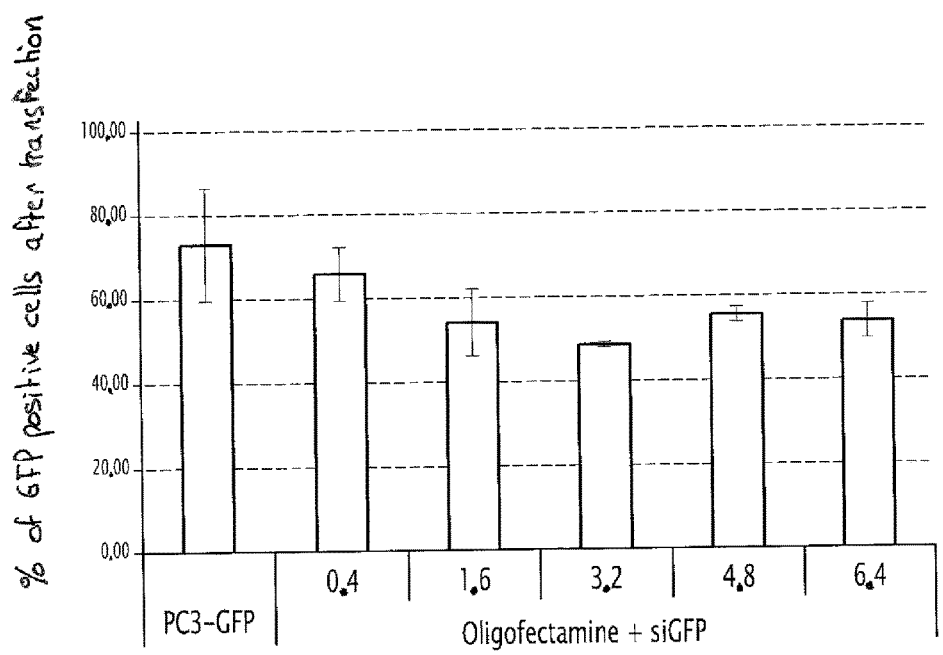

FIG. 17: Percentage of GFP positive cells after transfection of siGFP with Oligofectamine™.

Figure 18:
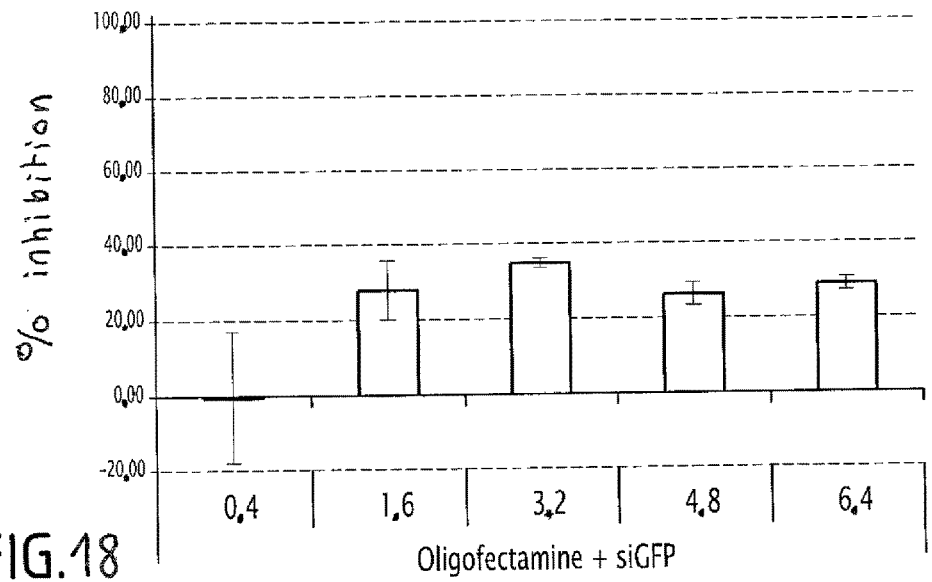

FIG. 18: Percent inhibition of the normalized GFP compared to untransfected cells and compared to the volume concentration of Oligofectamine™.

Figure 19:
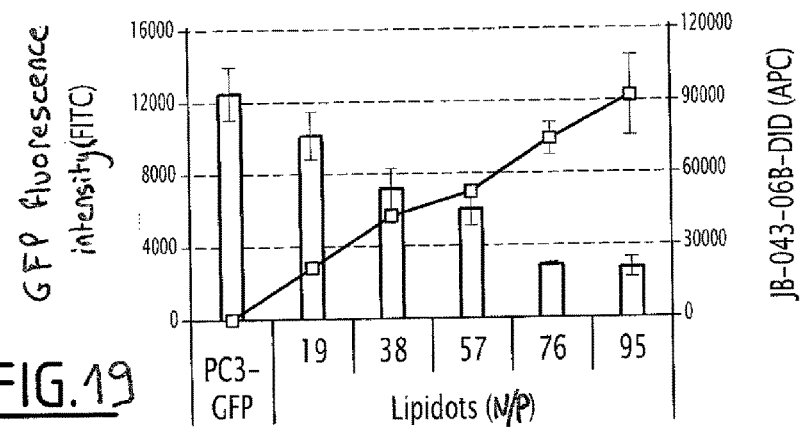

FIG. 19: Fluorescence intensity after siGFP transfection with lipid nanoparticles (Lipidots). The N/P ratio of 19/1 to 95/1 means the ratio between the lipid nanoparticle and siRNA. Histogram: intensity of GFP fluorescence. Curve: fluorescence intensity of perchlorate 1,1'-dioctadecyl-3,3,3', 3'-tétraméthylindodicarbocyanine (DiD) in the core of the particle.

Figure 20:
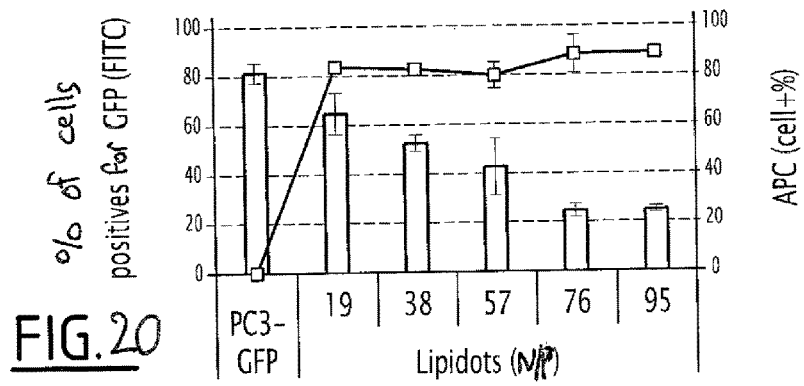

FIG. 20: Percentage of GFP positive cells after transfection with lipid nanoparticles (Lipidots). Histogram: percentage of GFP-positive cells. Curve: percentage of positive cells DiD (cells that have captured the nanoparticle).

Figure 21:
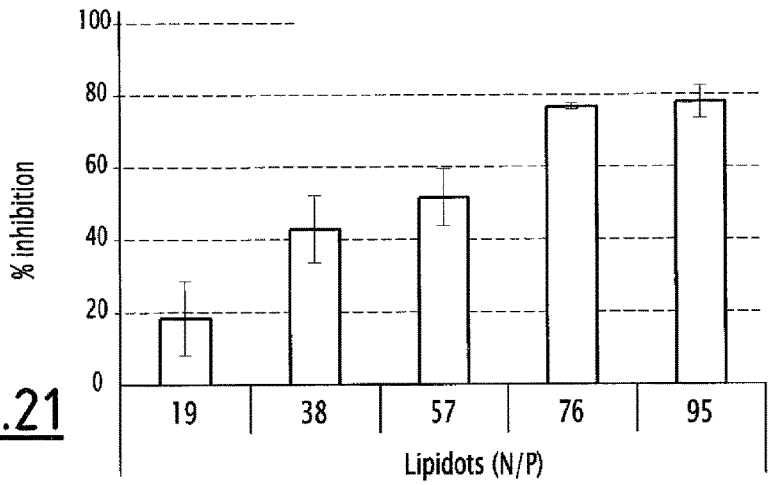

FIG. 21: Percent inhibition of the normalized GFP compared to non-transfected PC3-GFP cells.

Figure 22:
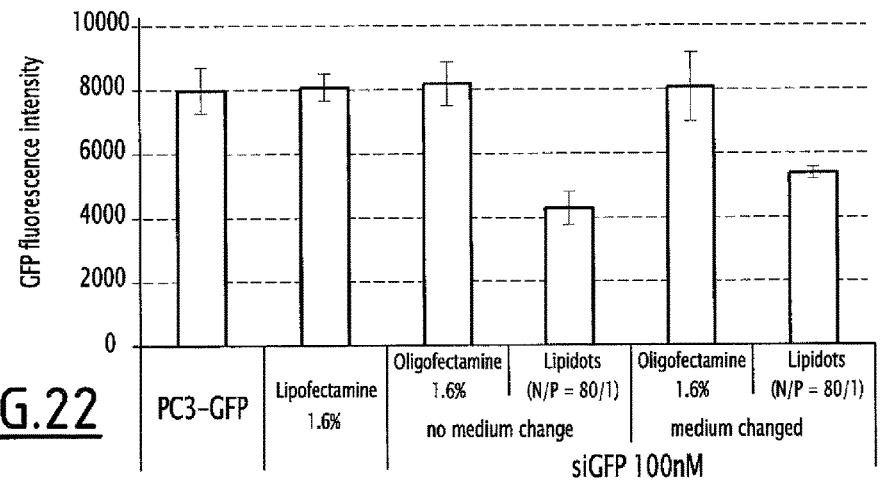

FIG. 22: Fluorescence intensity after transfection with and without medium change to "Transfection+day 1". FITC fluorescence intensity after transfection.

Figure 23:
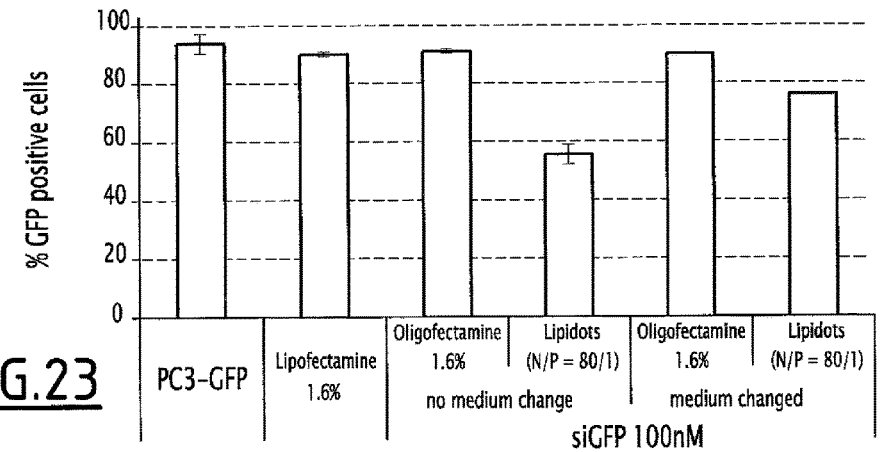

FIG. 23: Fluorescence intensity after transfection with and without medium change to "Transfection+day 1". Percentage of GFP positive cells following transfection.

Figure 24:
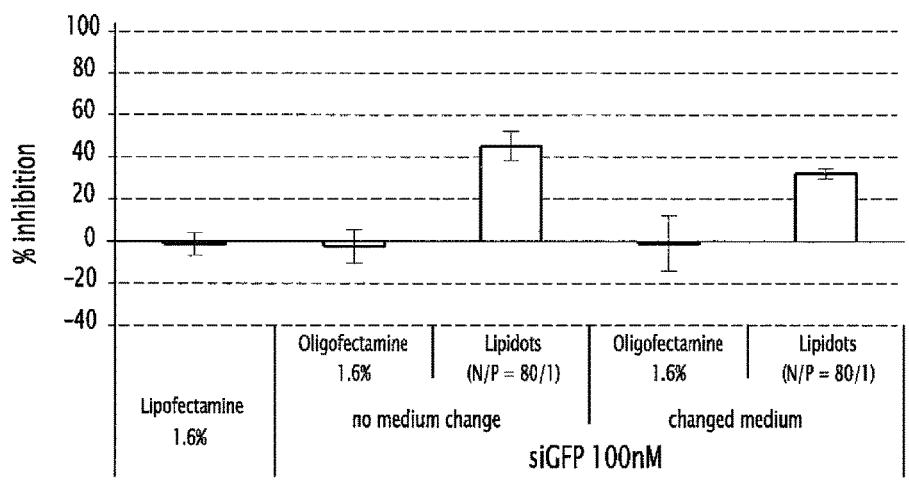

FIG. 24: Percent Inhibition of normalized GFP compared to non-transfected cells

Figure 25:
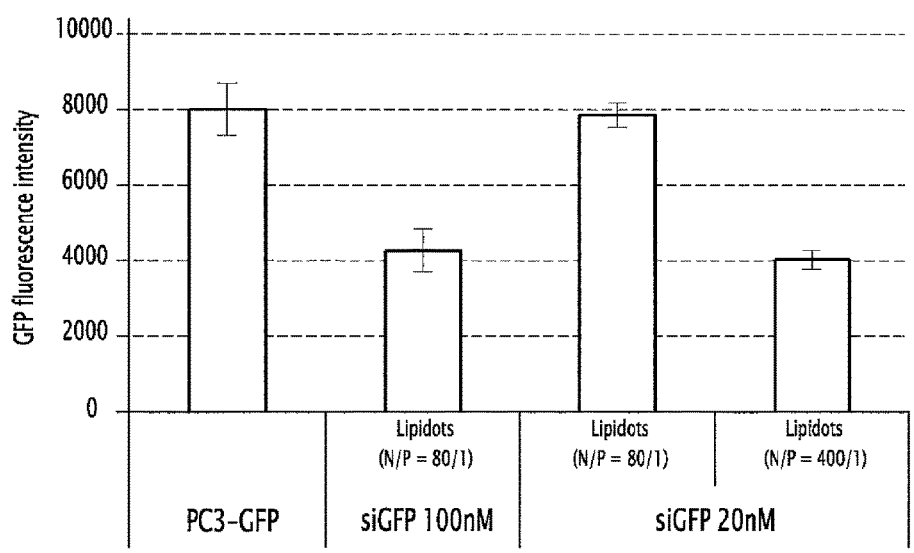

FIG. 25: FITC fluorescence intensity after transfection of siGFP (20 or 100 nM) by Lipidots, with N/P=80/1 or 400/1. Untransfected PC3-GFP cells are used as control.

Figure 26:
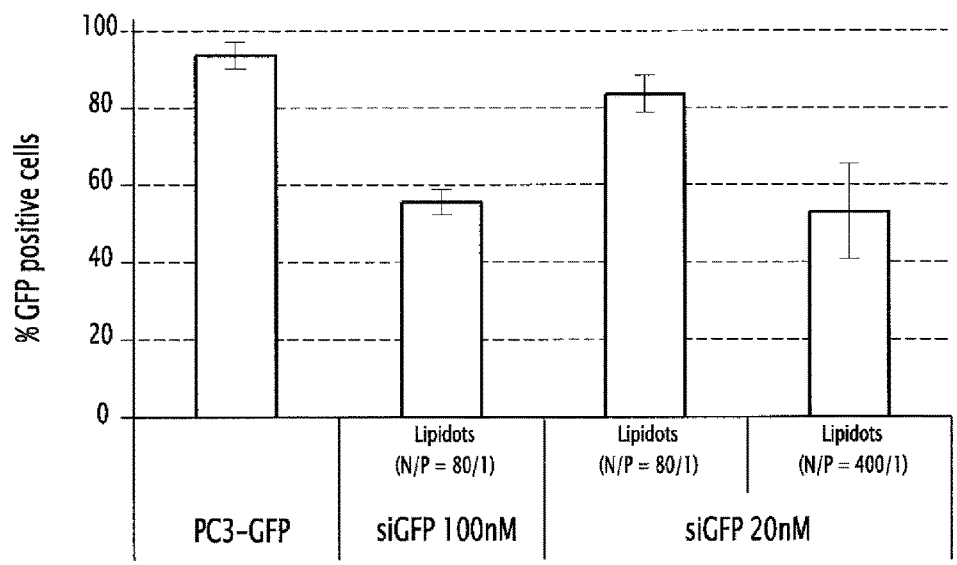

FIG. 26: Percentage of cells positive for GFP after transfection of siGFP (20 or 100 nM) by Lipidots, with N/P=80/1 or 400/1. Untransfected PC3-GFP cells are used as control.

Figure 27:
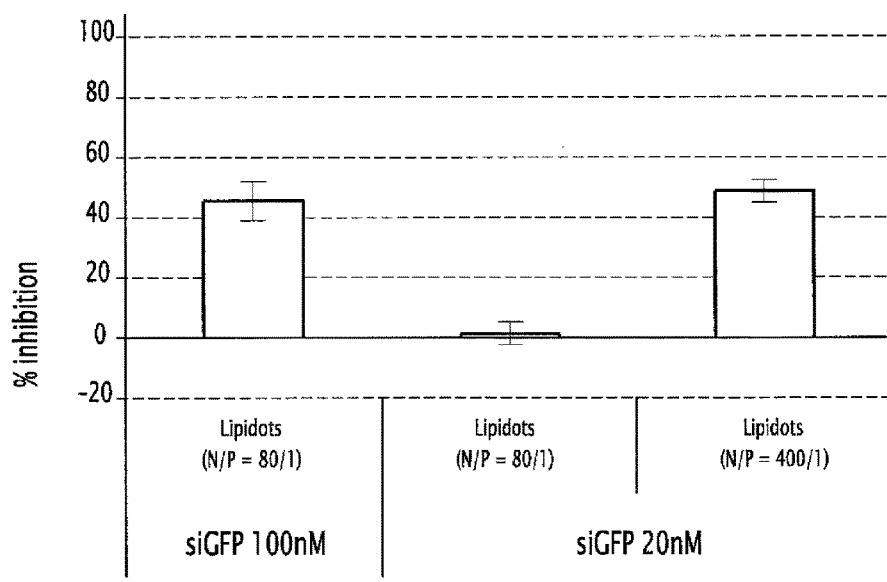

FIG. 27: Percent inhibition of the normalized GFP compared to non-transfected PC3-GFP cells.

DETAILED DESCRIPTION OF THE INVENTION

The inventors have demonstrated that a formulation in the form of a nanoemulsion, comprising a continuous aqueous phase and at least one dispersed phase, and further comprising a nucleic acid, allows for the efficient delivery of said nucleic acid in eukaryotic cells in 3D scaffold. In particular, said formulation achieves more efficient siRNA transfection in 3D culture than the commercial transfection agent, Oligofectamine™.

Without wishing to be bound by this theory, the inventors assume that this improved transfection efficacy in 3D environment, compared to commercial transfection agents such as Oligofectamine™ or more generally lipoplexes, is associated to:
the smaller size of the nanoparticles of the formulations used in the frame of the invention (below 200 nm, and preferably below 100 nm, in particular 20-60 nm, e.g. 40-50 nm) compared to the size of lipoplexes (about 300 nm), facilitates diffusion of the nanoparticles within the 3D scaffold in which cells to be transfected are embedded;

the stronger association of nucleic acids, DNA or RNA, to the nanoparticles of the formulations used in the frame of the invention, compared to lipoplexes.

Definitions

In the present application, by the term «nanoemulsion» is meant a composition having at least two phases, in general an oil phase and an aqueous phase in which the mean size of the dispersed phase is smaller than 1 micron, preferably 10 to 500 nm and in particular 20 to 200 nm, and most preferably 50 to 200 nm (see article by C. Solans, P. Izquierdo, J. Nolla, N. Azemar and M. J. Garcia-Celma, *Cuff Opin Colloid In,* 2005, 10, 102-110).

In the meaning of the present application, the expression «dispersed phase» designates the droplets comprising the optional oil/the cationic surfactant(s)/the solubilising lipid/the amphiphilic lipid/the co-surfactant/optional surfactant of formula (I)/optional helper lipid/optional imaging agent/optional therapeutic agent/optional nucleotide sequences able to modulate endogenous mechanisms of RNA interference. The dispersed phase is generally free of aqueous phase.

The term «droplet» encompasses both the droplets of liquid oil properly so-called and the solid particles derived from emulsions of oil-in-water type in which the dispersed phase is solid. In this latter case, the term solid emulsion is also often used.

The term «lipid» in this description designates all fatty bodies or substances containing fatty acids present in the fats of animal origin and in vegetable oils. They are hydrophobic or amphiphilic molecules chiefly formed of carbon, hydrogen and oxygen and having a density lower than that of water. The lipids may be in the solid state at ambient temperature (25° C.) as in waxes, or liquid state as in oils.

The term «phospholipid» concerns lipids having a phosphate group, in particular phosphoglycerides. Most often the phospholipids comprise a hydrophilic end formed by the optionally substituted phosphate group and two hydrophobic ends formed by fatty acid chains. Amongst the phospholipids, particular mention is made of phosphatidylcholine, phosphatidyl ethanolamine, phosphatidyl, inositol, phosphatidyl serine and sphingomyeline.

The term «lecithin» designates phosphatidylcholine i.e. a lipid formed from a choline, a phosphate, a glycerol and from two fatty acids. It more broadly covers living phospholipid extracts of vegetable or animal origin, provided that they are mostly formed of phosphatidylcholine. These lecithins generally form mixtures of lecithins carrying different fatty acids.

The term «fatty acid» designates aliphatic carboxylic acids having a carbon chain of at least 4 carbon atoms. Natural fatty acids have a carbon chain of 4 to 28 carbon atoms (generally an even number). The term long chain fatty acid is used for a length of 14 to 22 carbons and very long chain if there are more than 22 carbons.

By the term «surfactant» is meant compounds with amphiphilic structure imparting particular affinity thereto for interfaces of oil/water and water/oil type providing them with the capability of reducing the free energy of these interfaces and stabilising dispersed systems.

By the term «co-surfactant» is meant a surfactant acting in addition to a surfactant to further reduce interface energy.

By the term «hydrocarbon chain» it is meant to designate a chain composed of carbon and hydrogen atoms, saturated or unsaturated (double or triple bond). The preferred hydrocarbon chains are the alkyls or alkenyls.

By the term «alkylene» it is meant to designate an aliphatic divalent hydrocarbon group, saturated, linear chain or branched, preferably linear chain.

By «cyclic radical» is meant a radical derived from a crown crown system. For example a phenylene radical is a divalent radical derived from a benzene group. By «crown crown system» is meant a carbocycle or heterocycle, saturated, unsaturated or aromatic (aryl or heteroaryl).

a carbocycle: a saturated crown crown composed of carbon atoms (the preferred saturated carbocycles in particular being a cycloalkyl, such as a cyclopentyl or cyclohexyl), unsaturated (e.g. a cyclohexene) or aromatic (i.e. a phenyl);

a heterocycle: a crown crown group comprising, unless indicated otherwise, 5 to 6 atoms and comprising one or more heteroatoms selected from among O, N and/or S. The said heterocycle can be saturated or partly unsaturated and may comprise one or more double bonds. In this case the term heterocycloalkyl group is used. It may also be aromatic comprising, unless indicated otherwise, 5 to 6 atoms and then represent a heteroaryl group.

as non-aromatic heterocycle or heterocycloalkyl the following can be cited: pyrazolidinyl, imidazolidinyl, tetrahydrothiophenyl, dithiolanyl, thiazolidinyl, tetrahydropyranyl, dioxanyl, morpholinyl, piperidyl, piperazinyl, tetrahydrothiopyranyl, thiomorpholinyl, dihydrofuranyl, 2-imidazolinyl, 2,-3-pyrrolinyl, pyrazolinyl, dihydrothiophenyl, dihydropyranyl, pyranyl, tetrahydropyridyl, dihydropyridyl, tetrahydropyrinidinyl, dihydrothiopyranyl, isoxazolidinyl, as heteroaryl particular mention can be made of the following representative groups:

furyl, imidazolyl, isoxazolyl, isothiazolyl, oxadiazolyl, 1,2,4-oxadiazolyl, 1,3,4-oxadiazolyl, pyrazinyl, pyridazinyl, pyrazolyl, pyridyl, pyrimidinyl, pyrrolyl, 1,3,4-thiadiazolyl, 1,2,3-thiadiazolyl, thiazolyl, thienyl, triazolyl, 1,2,3-triazolyl and 1,2,4-triazolyl.

By «activated ester» is meant a group of formula —CO-LG, and by «activated carbonate» is meant a group of formula —O—CO-LG where LG is a good leaving group selected in particular from among a chlorine, imidazolyl, pentafluorophenolate, pentachlorophenolate, 2,4,5-trichlorophenolate 2,4,6-trichlorophenolate, or from among a group —O-succinimidyl, —O— benzotriazolyl, —O-(7-aza-benzotriazolyl) and —O-(4-nitrophenyl).

Throughout the instant application, the term "comprising" is to be interpreted as encompassing all specifically mentioned features as well optional, additional, unspecified ones. As used herein, the use of the term "comprising" also encompasses the embodiment wherein no features other than the specifically mentioned features are present (i.e. "consisting of") as well as the embodiment wherein features other than the specifically mentioned feature are present provided that the essential characteristics of the composition are not materially affected by their presence (i.e. "consisting essentially of").

Formulation in Nanoemulsion

In the frame of the invention, the formulation in the form of a nanoemulsion, comprising a continuous aqueous phase and at least one dispersed phase, comprises:

i) at least 5 mole % of amphiphilic lipid;

ii) 15 to 70 mole % of at least one cationic surfactant comprising:

ii-1) at least one lipophilic group selected from the group consisting of:
an R or R—(C=O)— group, where R is a linear hydrocarbon chain having 11 to 23 carbon atoms,
an ester or amide of fatty acids having 12 to 24 carbon atoms and phosphatidylethanolamine, and
a poly(propylene oxide), and
ii-2) at least one hydrophilic group comprising at least one cationic group selected from the group consisting of:
a linear or branched alkyl group having 1 to 12 carbon atoms and interrupted and/or substituted by at least one cationic group; and
a hydrophilic polymeric group comprising at least one cationic group; and
vi) 10% to 55 mole % of a co-surfactant comprising at least one poly(ethylene oxide) chain comprising at least 25 ethylene oxide units;
vii) a solubilising lipid; and
viii) a nucleic acid;
wherein the mole percentages of amphiphilic lipid, cationic surfactant and co-surfactant are relative to the (amphiphilic lipid/cationic surfactant/co-surfactant/optional helper lipid) assembly.

In an embodiment, the formulation in the form of a nanoemulsion further comprises a fusogenic or helper lipid.

In an embodiment, said formulation in nanoemulsion form further comprises a DNA tag and/or a tracer.

In an embodiment, said formulation in nanoemulsion form further comprises a biological ligand for targeting a cell and/or an organ.

It also provides a so-called «premix» formulation, free of nucleic acid, which allows the preparation of a formulation comprising a nucleic acid, intended to be transferred to eukaryotic cells, via the complexing of said nucleic acid with this «premix» formulation. This «premix» formulation can therefore advantageously be complexed with a nucleic acid that is adapted in accordance with the desired use of the final formulation.

Formulation of Premix Type

According to the invention, it is provided a formulation in the form of a nanoemulsion, comprising a continuous aqueous phase and at least one dispersed phase, comprises:
i) at least 5 mole % of amphiphilic lipid;
ii) 15 to 70 mole % of at least one cationic surfactant comprising:
ii-1) at least one lipophilic group selected from the group consisting of:
an R or R—(C=O)— group, where R is a linear hydrocarbon chain having 11 to 23 carbon atoms,
an ester or amide of fatty acids having 12 to 24 carbon atoms and phosphatidylethanolamine, and
a poly(propylene oxide), and
ii-2) at least one hydrophilic group comprising at least one cationic group selected from the group consisting of:
a linear or branched alkyl group having 1 to 12 carbon atoms and interrupted and/or substituted by at least one cationic group; and
a hydrophilic polymeric group comprising at least one cationic group; and
v) 10% to 55 mole % of a co-surfactant comprising at least one poly(ethylene oxide) chain comprising at least 25 ethylene oxide units; and
vi) a solubilising lipid;
wherein the mole percentages of amphiphilic lipid, cationic surfactant and co-surfactant are relative to the (amphiphilic lipid/cationic surfactant/co-surfactant/optional helper lipid) assembly.

As explained below, the: amphiphilic lipid/cationic surfactant/co-surfactant/optional helper lipid are the chief components in the crown part of the droplet structure in the «premix» formulation.

The emulsion is therefore an emulsion of oil-in-water type. It may be simple or multiple in particular comprising a second aqueous phase in the dispersed phase. Preferably it is simple.

The invention is based on the unexpected finding that the above-described formulation can be used as an efficient transfection agent and/or for the in vitro or ex vivo delivery of nucleic acids, e.g. of nucleic acids that modulate endogenous mechanisms of RNA interference, to eukaryote cells in 3D scaffold. The formulation advantageously exhibits good bioavailability and can allow limited degradation of the nucleic acid that is to be transfected which is generally observed with other delivery systems, in particular degradation by proteins.

In addition, the formulation is advantageously stable; it can be stored for several hours without any degradation being observed.

Cationic Surfactant

The formulation of the invention comprises a cationic surfactant comprising:
at least one lipophilic group selected from the group consisting of:
an R group representing a linear hydrocarbon chain having 11 to 23 carbon atoms;
an ester or amide of fatty acids having 12 to 24 carbon atoms and phosphatidylethanolamine, such as distearyl phosphatidylethanolamine (DSPE); and
a poly(propylene oxide); and
at least one hydrophilic group comprising at least one cationic group selected from the group consisting of:
a linear-chain or branched alkyl group having 1 to 12 carbon atoms and interrupted and/or substituted by at least one cationic group; and
a hydrophilic polymeric group comprising at least one cationic group, the said polymeric group being particularly selected from the group consisting of:
a poly(ethylene oxide) typically comprising 3 to 500 ethylene oxide units, preferably 20 to 200 ethylene oxide units, and comprising at least one cationic group,
a polysaccharide, such as dextran, cellulose or chitosan, particularly having molecular weights of between 0.5 et 20 kDa, for example between 1 and 12 kDa,
a polyamine, such as a chitosan or polylysine, particularly having molecular weights of between 0.5 and 20 kDa, for example between 1 and 12 kDa.

By «ester or amide of fatty acids having 12 to 24 carbon atoms and phosphatidylethanolamine», is meant a group of formula:

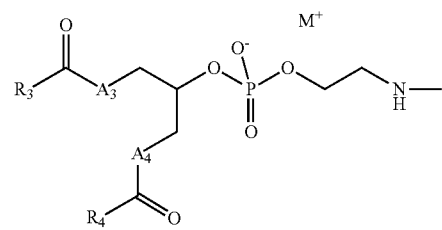

where:
$R_3$ and $R_4$ are independently a linear hydrocarbon chain having 11 to 23 carbon atoms;
$A_3$ and $A_4$ represent O or NH; and
M is H or a cation.

The cationic groups of the cationic surfactant are typically:
oniums selected from the group consisting of ammonium, imidazolium, pyridinium, pyrrolidinium, piperidinium, phosphonium or sulfonium groups; or
metal complexes between a radical of a mono- or multidentate chelating organic group e.g. phenantroline, pyridine, ethylene diamine tetraacetic acid (EDTA), diethylene triamine pentaacetic acid (DTPA), porphyrins, phtalocyanines, chlorins, bacteriochlorins complexed with an inorganic cation such as $Ca^{2+}$, $Al^{3+}$, $Ni^+$, $Zn^{2+}$, $Fe^{2+}$, $Fe^{3+}$ or $Cu^{2+}$,
the ammonium groups, and in particular —$^+NMe_3$, —$^+NHMe_2$, —$^+NH_2Me$ and —$^+NH_3$, particular preference being given to —$^+NH_3$.

Evidently anions are associated with the cationic group(s) so that the formulation is electrically neutral. The type of anion is not limited. As illustrations mention can be made of halides, in particular chlorides or bromides or trifluoroacetate.

In the cationic surfactant the type of linkage group linking the lipophilic group(s) to the hydrophilic group(s) comprising at least one cationic group is not limited. Examples of linkage groups are given below (group L).

In one embodiment, the cationic surfactant has the following formula (A):

$$[(Lipo)_l\text{-L-}(Hydro)_h]^{n+},(n/m)[A]^{m-} \quad (A)$$

where:
l and h are independently integers of between 1 and 4;
n is an integer no lower than 1, generally between 1 and 50;
Lipo represents a lipophilic group such as defined above;
Hydro represents a hydrophilic group such as defined above comprising at least one cationic group;
L is a linkage group;
A is an anion;
m is an integer representing the charge of the anion;
n is an integer representing the charge of the cation $[(Lipo)_l\text{-L-}(Hydro)_h]$.

In above-mentioned formula (A), L is preferably such that:
when l and h represent 1, L is a divalent linkage group selected from the group consisting of:
a single bond;
a Z group selected from the group consisting of —O—, —NH—, —O(OC)—, —(CO)O—, —(CO)NH—, —NH(CO)—, —O—(CO)—O—, —NH—(CO)—O—, —O—(CO)—NH— and —NH—(CO)—NH, —O—PO(OH)—O— or a cyclic divalent radical having 5 to 6 atoms;
an Alk group being an alkylene having 1 to 6 carbon atoms; and
a group: Z-Alk, Alk-Z, Alk-Z-Alk or Z-Alk-Z where Alk and Z are such as defined above and where the two Z groups of the Z-Alk-Z group are the same or different;
when one of the groups l or h represents 1, and the other represents 2, L is a trivalent group selected from the group consisting of a phosphate group OP—(O—)$_3$, a group derived from glycerol of formula —O—$CH_2$—CH—(O—)$CH_2$—O— and a cyclic trivalent radical having 5 to 6 atoms;
for the other values of l and h, L is a cyclic multivalent radical having 5 to 6 atoms.

In particularly preferred manner L is such that:
when l and h represent 1, L is a divalent linkage group selected from the group consisting of:
a single bond;
a Z group selected from the group consisting of —O—, —NH—, —O(OC)—, —(CO)O—, —(CO)NH—, —NH(CO)—, —O—(CO)—O—, —NH—(CO)—O—, —O—(CO)—NH— and —NH—(CO)—NH or —O—PO(OH)—O—,
when one of the groups l or h represents 1 and the other represents 2, L is a trivalent group selected from the group consisting of a phosphate group OP—(O—)$_3$ and a group derived from glycerol of formula —O—$CH_2$—CH—(O—)$CH_2$—O—.

In above-mentioned formula (A), l and h are preferably 1 or 2 independently.

According to a first alternative, the hydrophilic group of the cationic surfactant is a linear-chain or branched alkyl group having 1 to 12 carbon atoms and interrupted and/or substituted by at least one cationic group. As examples of such cationic surfactants the following can be cited: 1) (Lipo)-$(CH_2)_{m1}$—$NR_{30}R_{31}R_{32}$, where Lipo is a lipophilic group such as defined above, m1 is 1 or 2 and $R_{30}$, $R_{31}$ and $R_{32}$ are independently H, Me or —$CH_2$—$CH_2$—OH,

2)

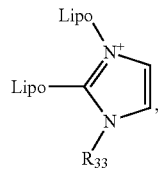

where each Lipo is independently a lipophilic group such as defined above and R33 is H, Me or —$CH_2$—$CH_2$—OH,

3)

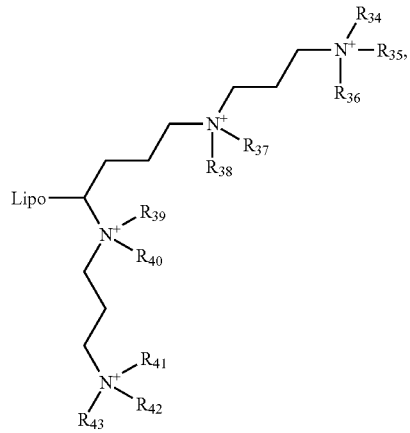

where Lipo is a lipophilic group such as defined above, and $R_{34}$, $R_{35}$, $R_{36}$, $R_{37}$, $R_{38}$, $R_{39}$, $R_{40}$, $R_{41}$, $R_{42}$ and $R_{43}$ are independently H, Me or —$CH_2$—$CH_2$—OH.

In one embodiment, the cationic surfactant is selected from the group consisting of:

N[1-(2,3-dioleyloxy) propyl]-N,N,N-trimethylammonium (DOTMA), 1,2-dioleyl-3-trimethylamonium-propane (DOTAP), N-(2-hydroxyethyl)-N,N-dimethyl-2,3-bis(tetradecyloxy-1-propananium) (DMRIE), 1-[2-(oleoyloxy)ethyl]-2-oleyl-3-(2-hydroxyethyl)imidazolinium (DOTIM), and dioctadecylamidoglycylspermine (DOGS) (in protonated form), and is preferably 1,2-dioleyl-3-trimethylamonium-propane (DOTAP).

According to a second alternative, the hydrophilic group of the cationic surfactant is a hydrophilic polymeric group comprising at least one cationic group.

When the hydrophilic group of the cationic surfactant is polymeric, the cationic group(s) may be terminal or pendant groups. For example:

when the hydrophilic polymeric group is a poly(ethylene oxide), the cationic group(s) are generally positioned on a terminal group at the end of the poly(ethylene oxide) chain;

when the hydrophilic polymeric group is dextran or cellulose, the cationic group(s) are generally positioned on a terminal group at the end of the polysaccharide chain;

when the hydrophilic polymeric group is chitosan, the cationic group(s) are generally a pendant group, in particular —$NH_3^+$ groups present in an acid medium on chitosan.

In one embodiment, the cationic group(s) is/are a terminal group. The pendant groups of adjacent anionic surfactants on the surface of the droplets of the dispersed phase repel one another via electrostatic interactions and, as a result, the formulations comprising cationic surfactants in which the Hydro group comprises pendant groups are generally less stable.

In another embodiment, the cationic group(s) is/are pendant group(s). It is advantageously possible to use a cationic surfactant in which the hydrophilic group comprises several pendant cationic groups, and hence to obtain a formulation with greater positive charge and which will better allow the complexing of negative species such as the nucleotide sequences able to modulate endogenous mechanisms of interfering RNA.

The preferred hydrophilic polymeric group is a radical of a poly(ethylene oxide) typically comprising 3 to 500 ethylene oxide units, preferably 20 to 200 ethylene oxide units, and comprising at least one cationic group.

Therefore in one embodiment, the cationic surfactant has one of the following formulas:

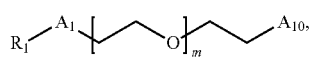

(AI)

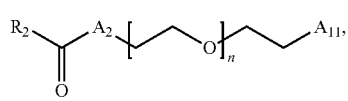

(AII)

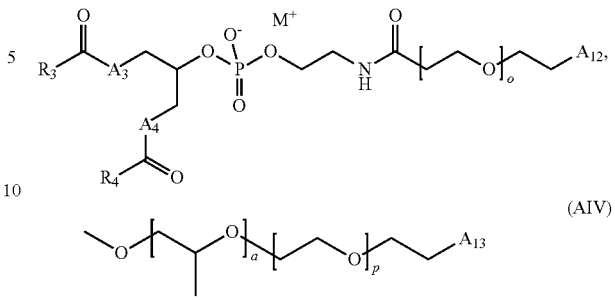

where:
$R_1$, $R_2$, $R_3$ and $R_4$ are independently a linear hydrocarbon chain having 11 to 23 carbon atoms;

$A_1$, $A_2$, $A_3$ and $A_4$ are O or NH;

m, n, o and p independently represent integers from 3 to 500, preferably 20 to 200; and a is an integer from 20 to 120;

M is H or a cation;

$A_{10}$, $A_{11}$, $A_{12}$ and $A_{13}$ are independently a —$^+NR_{20}R_{21}R_{22}$ group where $R_{20}$, $R_{21}$ and $R_{22}$ independently represent H, Me or —$CH_2$—$CH_2$—OH.

In one embodiment, in formula (AII), $A_{11}$ represents —$^+NH_3$, and the cationic surfactant has the following formula:

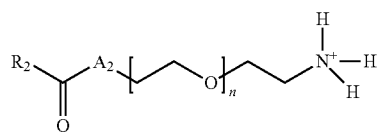

(AV)

where $A_2$, $R_2$ and n are such as defined above. Preferably in formula (AII), $R_2$ represents $C_{17}H_{35}$.

Without wishing to be bound by any particular theory, it would seem that the presence of the hydrophilic polymeric group allows:

stabilisation of the formulation; and protection of the nucleotide sequences able to modulate endogenous mechanisms of interfering RNA located on the surface of the droplets against the proteins of the medium in which the formulation is administered/used, and hence protection against degradation by these proteins of the nucleotide sequences able to modulate endogenous mechanisms of interfering RNA.

According to a third alternative, the formulation of the invention comprises at least two cationic surfactants, of which:

one is selected from the group consisting of:
N[1-(2,3-dioleyloxy) propyl]-N,N,N-trimethylammonium (DOTMA);
1,2-dioleyl-3-trimethylamonium-propane (DOTAP);
N-(2-hydroxyethyl)-N,N-dimethyl-2,3-bis(tetradecyloxy-1-propananium) (DMRIE);
1-[2-(oleoyloxy)ethyl]-2-oleyl-3-(2-hydroxyethyl)imidazolinium chloride (DOTIM); and
dioctadecylamidoglycylspermine (DOGS), and is preferably 1,2-dioleyl-3-trimethylamonium-propane (DOTAP), and the other is a cationic surfactant comprising:
  at least one lipophilic group selected from the group consisting of:
    an R or R—(C═O)— group, where R is a linear hydrocarbon chain having 11 to 23 carbon atoms;
    an ester or an amide of fatty acids having 12 to 24 carbon atoms, and phosphatidylethanolamine, such as distearyl phosphatidylethanolamine (DSPE); and
    a poly(propylene oxide), and
  a hydrophilic polymeric group comprising at least one cationic group, the said polymeric group being selected from the group consisting of:
    a poly(ethylene oxide) typically comprising 3 to 500 units of ethylene oxide, preferably 20 to 200 units of ethylene oxide, and comprising at least one cationic group;
    a polysaccharide, such as dextran, cellulose or chitosan;
    a polyamine, such as a chitosan or polylysine,
  and is preferably a poly(ethylene oxide) comprising at least at least one cationic group.

In one embodiment the formulation of the invention, as cationic surfactants, comprises:
  1,2-dioleyl-3-trimethylamonium-propane; and
  a cationic surfactant comprising:
    at least one lipophilic group selected from the group consisting of:
      an R or R—(C═O)— group, where R is a linear hydrocarbon chain having 11 to 23 carbon atoms;
      an ester or amide of fatty acids having 12 to 24 carbon atoms, and phosphatidylethanolamine such as distearyl phosphatidylethanolamine (DSPE); and
      a poly(ethylene oxide) typically comprising 3 to 500 units of ethylene oxide, preferably 20 to 200 units of ethylene oxide, and comprising at least one cationic group.

In one embodiment the formulation of the invention, as cationic surfactants, comprises:
  1,2-dioleyl-3-trimethylamonium-propane; and
  a compound of formula (AII) such as defined above, in particular of formula (AV).

The cationic surfactant is positioned in the crown part of the droplets of the formulation. It is linked via electrostatic interactions to the nucleotide sequences able to modulate endogenous mechanisms of RNA interference and allows the siRNAs to be maintained on the surface of the droplets.

The formulation comprises 15 to 70 mole % of at least one cationic surfactant relative to the whole (amphiphilic lipid/cationic surfactant/co-surfactant/optional helper lipid). Below 15%, the formulation does not contain sufficient positive charges and subsequent complexing of the «premix» formulation with the nucleotide sequences (negatively charged) is insufficient. Over and above 70%, the formulations are not stable and generally are even unable to be formulated (the forming of the nanoemulsion is not possible since the droplets coalesce to form two phases), and the droplets generally become toxic for the cells.

These proportions are particularly adapted to obtain efficient complexing of the nucleic acid that modulates endogenous mechanisms of interfering RNA, and hence good delivery and/or transfection.

Helper Lipid

In one embodiment, the formulation of the invention comprises a helper lipid which is able to facilitate cytosolic release by destabilising the endosomal membrane. Preferably this lipid is dioleylphosphatidylethanolamine (DOPE).

This lipid allows the promoting of endosomal escape of the droplets of the formulation of the invention, and hence of the nucleotide sequences able to modulate endogenous mechanisms of RNA interference contained therein, and generally improves the silencing efficacy of the gene of interest.

The lipid able to facilitate cytosolic release by destabilising the endosomal membrane is positioned in the crown part of the droplets of the formulation.

Amphiphilic Lipid

The formulation comprises at least one amphiphilic lipid positioned in the crown part of the droplets of the formulation.

To form a stable nanoemulsion, it is necessary to include in the composition at least one amphiphilic lipid as surfactant. The amphiphilic nature of the surfactant ensures the stabilising of the oil droplets in the continuous aqueous phase. Below 5 mole % of amphiphilic lipid relative to the whole (amphiphilic lipid/cationic surfactant/co-surfactant/optional helper lipid), the formulations are not stable, and generally are not even able to be formulated (the forming of the nanoemulsion is not possible since the droplets coalesce to form two phases).

In general, the formulation comprises 5 to 85 mole %, preferably 5 to 75 mole %, in particular 5 to 50 mole % and further particularly 8 to 30 mole % of amphiphilic lipid relative to the whole (amphiphilic lipid/cationic surfactant/co-surfactant/optional helper lipid).

The quantity of amphiphilic lipid advantageously contributes towards controlling the size of the dispersed phase of the nanoemulsion.

The amphiphilic lipids comprise a hydrophilic part and a lipophilic part. They are generally selected from the group consisting of compounds whose lipophilic part comprises a saturated or unsaturated, linear or branched chain having 8 to 30 carbon atoms. They can be selected from the group consisting of phospholipids, cholesterols, lysolipids, sphingomyelins, tocopherols, glucolipids, stearylamines, cardiolipins of natural or synthetic origin; molecules composed of a fatty acid coupled to a hydrophilic group va an ether or ester function such as the esters of sorbitan e.g. sorbitan monooleate and monolaurate marketed under the trade name Span® by Sigma; polymerised lipids; lipids conjugated to short chains of polyethylene oxide (PEG) such as the non-ionic surfactants sold under the trade names Tween® by ICI Americas, Inc. and Triton® by Union Carbide Corp.; sugar esters such as mono- and di-laurate, mono- and di-palmitate, sucrose mono- and distearate; the said surfactants can be used alone or in a mixture.

Phospholipids are the preferred amphiphilic lipids.

Lecithin is a particularly preferred amphiphilic lipid.

Solubilising Lipid

The formulation also comprises a solubilising lipid comprising at least one fatty acid glyceride contained in the dispersed phase of the nanoemulsion, more specifically in the core part of the droplets. This compound has the chief role of solubilising the amphiphilic lipid which is scarcely soluble in the dispersed phase of the nanoemulsion.

The solubilising lipid is a lipid having sufficient affinity for the amphiphilic lipid to allow solubilising thereof. Preferably the solubilising lipid is solid at ambient temperature.

If the amphiphilic lipid is a phospholipid, it may in particular be:
  esters of fatty acid and fatty alcohol such as cetyl palmitate; or
  derivatives of glycerol and in particular of glycerides obtained by esterification of glycerol with fatty acids.

The solubilising lipid used is advantageously selected in relation to the amphiphilic lipid used. It generally has a close chemical structure to ensure the sought-after solubilisation.

It may be an oil or wax. Preferably the solubilising lipid is solid at ambient temperature (20° C.), but liquid at body temperature (37° C.).

The preferred solubilising lipids, in particular for the phospholipids, are the esters of fatty acids and fatty alcohol such as cetyl palmitate, or the glycerides of fatty acids in particular of saturated fatty acids, and particularly saturated fatty acids having 8 to 18 carbon atoms, more preferably 12 to 18 carbon atoms. Advantageously it is a mixture of different glycerides.

Preferably, they are glycerides of saturated fatty acids comprising at least 10% by weight of C12 fatty acids, at least 5% by weight of C14 fatty acids, at least 5% by weight of C16 fatty acids and at least 5% by weight of C18 fatty acids.

Preferably, they are glycerides of fatty acids comprising 0% to 20% by weight of C8 fatty acids, 0% to 20% by weight of C10 fatty acids, 10% to 70% by weight of C12 fatty acids, 5% to 30% by weight of C14 fatty acids, 5% to 30% by weight of C16 fatty acids and 5% to 30% by weight of C18 fatty acids.

Particularly preferred are mixtures of semi-synthetic glycerides solid at ambient temperature sold under the trade name Suppocire® NC by Gattefossé and approved for injection in man. N-type Suppocire® are obtained by direct esterification of fatty acids and glycerol. They are semi-synthetic glycerides of saturated C8 to C18 fatty acids of which the quali-quantitative composition is given in the Table below.

The aforementioned solubilising lipids allow a formulation to be obtained in the form of an advantageously stable nanoemulsion. Without wishing to be bound by any particular theory, it is assumed that the aforementioned solubilising lipids allow the obtaining of droplets in the nanoemulsion which have an amorphous core. The core thus obtained has higher internal viscosity without exhibiting any crystallinity. Crystallisation is harmful for the stability of the nanoemulsion since it generally leads to aggregation of the droplets and/or to expelling of the encapsulated molecules outside the droplets. These physical properties promote the physical stability of the nanoemulsion.

The amount of solubilising lipid may vary extensively in relation to the type and amount of amphiphilic lipid contained in the dispersed phase. In general, the core of the droplets (comprising the solubilising lipid, optional oil, optional imaging agent, optional therapeutic agent if it is lipophilic) comprises 1 to 100% by weight, preferably 5 to 80% by weight and more preferably 40 to 75% by weight of solubilising lipid.

| Fatty acid composition of Suppocire ® NC by Gattefossé | |
|---|---|
| Chain length | [weight %] |
| C8 | 0.1 to 0.9 |
| C10 | 0.1 to 0.9 |
| C12 | 25 to 50 |
| C14 | 10 to 24.9 |
| C16 | 10 to 24.9 |
| C18 | 10 to 24.9 |

Oil

The dispersed phase may also comprise one or more other oils contained in the core of the droplets.

The oils used preferably have a hydrophilic-lipophilic balance (HLB) of less than 8 and more preferably of between 3 and 6. Advantageously the oils are used without chemical or physical modification prior to the forming of the emulsion.

The oils are generally selected from the group consisting of biocompatible oils, and in particular from the group consisting of oils of natural origin (vegetable or animal) or synthetic. Among these oils particular mention can be made of oils of natural vegetable origin amongst which are included soybean, flax, palm, groundnut, olive, grape seed and sunflower seed oil; synthetic oils which particularly include triglycerides, diglycerides and monoglycerides. These oils may be first press, refined or inter-esterified oils.

The preferred oils are soybean oil and flax oil.

In general and when present the oil is contained in the core of the droplets (comprising the solubilising lipid, optional oil, optional imaging agent, optional therapeutic agent if it is lipophilic) in a proportion ranging from 1 to 80% by weight, preferably between 5 and 50% by weight and more preferably 10 to 30% by weight.

The dispersed phase may further contain other additives such as dyes, stabilisers, preserving agents or other active ingredients in suitable amounts.

Co-Surfactant

The formulation comprises a co-surfactant which allows stabilising of the nanoemulsion.

The co-surfactants which can be used in the formulations of the invention are generally water-soluble surfactants. They comprise at least one poly(ethylene oxide) chain comprising at least 25, in particular at least 30, preferably at least 35 units of ethylene oxide. The number of ethylene oxide units is generally lower than 500.

Formulations comprising a co-surfactant comprising a poly(ethylene oxide) chain comprising fewer than 25 units of ethylene oxide are not stable. In general, it is not even possible to prepare the nanoemulsion.

These numbers of units are particularly adapted to prevent leakage of the nucleotide sequences, able to modulate endogenous mechanisms of interfering RNA, outside the droplets.

The inventors have effectively observed that a formulation not comprising a co-surfactant is not sufficiently stable.

In addition, without wishing to be bound by any particular theory, it would seem that the presence of the chain composed of ethylene oxide units in the co-surfactant provides protection of the nucleotide sequences able to modulate endogenous mechanisms of interfering RNAs located on the surface of the droplets against the proteins of the medium in which the formulation is administered/used, and hence against degradation of the said nucleotide sequences by these proteins.

As examples of co-surfactants particular mention can be made of the conjugated compounds polyethylene glycol/phosphatidyl-ethanolamine (PEG-PE), the ethers of fatty acid and of polyethylene glycol such as the products sold under the trade names Brij® (for example Brij® 35, 58, 78 or 98) by ICI Americas Inc., the esters of fatty acid and of esters polyethylene glycol such as the products sold under the trade names Myrj® by ICI Americas Inc. (for example Myrj® 45, 52, 53 or 59) and the block copolymers of ethylene oxide and propylene oxide such as the products sold under the trade names Pluronic® by BASF AG (for example Pluronic® F68, F127, L64, L61, 10R4, 17R2, 17R4, 25R2 or 25R4) or the products sold under the trade name Synperonic® by Unichema Chemie BV (for example Synperonic® PE/F68, PE/L61 or PE/L64).

Therefore the co-surfactant is contained both in the continuous aqueous phase and in the dispersed phase. The hydrophobic part of the co-surfactant inserts itself in the droplets of the dispersed phase, whilst the polyalkoxylated chains are in the continuous aqueous phase. In the present application, the described weight percentages of the dispersed phase are calculated when considering that the co-surfactant belongs to the dispersed phase.

The formulation comprises 10% to 55 mole % of co-surfactant relative to the whole (amphiphilic lipid/cationic surfactant/co-surfactant/optional helper lipid). Below 10% the formulations are not stable and in general cannot even be formulated (the formation of the nanoemulsion is not possible since the droplets coalesce to form two phases). Over and above 55%, the subsequent complexing of the «premix» formulation with the nucleotide sequences does not take place probably because the positive charges of the cationic surfactant are masked by the poly(ethylene oxide) chains of the co-surfactant, and hence are more accessible for binding via electrostatic bonding with the nucleotide sequences.

The co-surfactant may also exhibit other effects in the envisaged application of the nanoemulsion.

According to one embodiment, the dispersed phase of the nanoemulsion is grafted on the surface with molecules of interest such as biological ligands, to increase the specific targeting of an organ. Said grafting allows specific recognition of some cells or some organs by promoting the internalisation of the droplets of the formulation of the invention by the target cells which express the surface receptor. It is therefore possible to transfect cells known to be resistant to prior art transfecting agents. Preferably, surface grafting is performed by coupling the molecules of interest or their precursors with an amphiphilic compound in particular with the co-surfactant. The nanoemulsion then comprises a grafted co-surfactant. In this case, the co-surfactant acts as spacer allowing the accommodating of the molecules of interest on the surface.

For example, the molecules of interest may be:
  targeting biological ligands such as antibodies, peptides, saccharides, aptamers, oligonucleotides or compounds such as folic acid;
  a stealth agent: an added entity to impart stealth to the nanoemulsion against the immune system, to increase its circulation time in the body and to slow down the elimination thereof.

For example when the biological ligand is a peptide comprising one or more cysteins, grafting to the alkylene oxide chain of the surfactant can be ensured by thiol maleimide coupling.

Tracer

According to an embodiment, the formulation in nanoemulsion form to be used in the frame of the invention further comprises a tracer.

The term "tracer" denotes a molecule giving the possibility of determining whether the nanoparticle was integrated into a cell. In certain embodiments, said tracer is a magnetic tracer, a radioactive tracer or a fluorophore.

The magnetic tracer may be a gadolinium chelate or a magnetic nanocrystal, such as for example a nanocrystal of iron, manganese oxide or iron-platinum (Fe—Pt).

The radioactive tracer may be a compound comprising a radionuclide, such as for example $^{123}$I, $^{18}$F, $^{11}$C, or a chelate of $^{99m}$Tc or $^{111}$In, or a chelate of metal cations $^{68}$Ga, $^{64}$Cu.

Preferably the imaging agent is a lipophilic fluorophore allowing the performing of optical imaging.

During in vitro or ex vivo applications, for which imaging methods are applied, such as fluorescence microscopy or cytometry of the FACS (Fluorescence Activating Cell Sorting) type, fluorophores are generally applied which are excited with visible wavelengths, typically comprised between 450 nm and 650 nm. These are notably hydrophilic cyanins or FITC (Fluorescein isothiocyanate). These fluorophores may be encapsulated in the lipid core of the nanoparticles or, when they are hydrophilic be localised at their surface.

As lipophilic fluorophore it is possible to cite the compounds described in Chapter 13 ("Probes for Lipids and Membranes") in the InVitrogen catalogue. More specifically, as fluorophore mention can particularly be made of indocyanine green (ICG), the analogues of fatty acids and phospholipids functionalised by a fluorescent group such as the fluorescent products sold under the trade names Bodipy® for example Bodipy® 665/676 (Ex/Em.); the lipophilic derivatives of carbocyanines such as 1,1-dioctadecyl-3,3,3',3'-tetramethylindodicarbocyanine perchlorate (DiD) sold for example under the reference D-307, 3,3'-dihexadecyloxacarbocyanine perchlorate (DiO) sold for example under the reference D1125, 1,1'-dihexadecyl-3,3, 3',3'-tetramethylindocarbocyanine perchlorate (DiI) sold for example under the reference D384; fluorescent probes derived from sphingolipids, from steroids or from lipopolysaccharides such as the products sold under the trade names BODIPY® TR ceramids, BODIPY® FL C5-lactosylceramide, BODIPY® FL C5-ganglioside, BODIPY® FL cerebrosides; the amphiphilic derivatives of cyanines, of rhodamines, of fluoresceins or coumarins such as octadecyl rhodamine B, octadecyl ester of fluorescein and 4-heptadecyl-7-hydroxycoumarin; and diphenylhexatriène (DPH) and derivatives thereof; all these products being sold by Invitrogen.

According to one preferred embodiment of the invention, the fluorophore is indocyanine green, 1,1'-dioctadecyl-3,3, 3',3'-tetramethylindodicarbocyanine perchlorate, 3,3'-dihexadecyloxacarbocyanine perchlorate, or 1,1'-dihexadecyl-3,3,3',3'-tetramethylindocarbocyanine perchlorate.

Therapeutic Agent

The formulation in the form of a nanoemulsion may further comprise a therapeutic agent.

The therapeutic agents able to be encapsulated in the nanoemulsion of the invention particularly contain the active ingredients acting via chemical, biological or physical route. These may therefore be pharmaceutical active ingredients or biological agents such as DNA, proteins, peptides or antibodies or agents useful for physical therapy such as compounds useful for heat therapy, compounds releasing singlet oxygen when excited by light and used for phototherapy, and radioactive agents. Preferably they are active ingredients administered via parenteral route.

Depending on its lipophilic or amphiphilic affinity the therapeutic agent can be encapsulated by the dispersed phase or is positioned at the interface of the two phases.

The type of therapeutic agent encapsulated in the nanoemulsion is not particularly limited. However the nanoemulsion is of particular interest for scarcely soluble compounds which are difficult to formulate in conventional administration systems, and for active ingredients used in phototherapy for which the quantum yield can be maintained.

On account of the mild conditions of the preparation method, the described formulation is of particular interest for the encapsulating of therapeutic agents which are degraded at high temperature.

Among the pharmaceutical active ingredients of interest as therapeutic agents, particular mention can be made of the agents used in the treatment of AIDS, the agents used in the treatment of heart disease, analgesics anaesthetics, anorexigenics, anthelmintics, antiallergics, antianginals, antiarrhythmics, anticholinergics, anticoagulants, antidepressants, antidiabetics, antidiuretics, antiemetics, anticonvulsants, antifungals, antihistaminics, antihypertensives, anti-inflammatories, anti-migraines, antimuscarinics, antimycobacterials, anticancer drugs including antiparkinsons, antithyroid drugs, antivirals, astringents, blocking agents, blood products, blood substitutes, cardiac inotropic agents, cardiovascular agents, central nervous system agents, chelators, chemotherapy agents, hematopoietic growth factors, corticosteroids, antitussives, dermatological agents, diuretics, dopaminergic drugs, elastase inhibitors, endocrine agents, ergot alkaloids, expectorants, gastro-intestinal agents, genitourinary agents, growth hormone triggering factor, growth hormones, hematologic agents, hematopoietic agents, hemostatics, hormones, immunosuppressives, interleukins, analogues of interleukins, lipid regulating agents, gonadoliberin, muscle relaxants, narcotic antagonists, nutrients, nutritive agents, oncology therapy, organic nitrates, vagomimetics, prostaglandins, antibiotics, renal agents, respiratory agents, sedatives, sexual hormones, stimulants, sympathomimetics, systemic anti-infectious agents, tacrolimus, thrombolytic agents, thyroid agents, treatments for attention disorders, vasodilators, xanthines, cholesterol-reducing agents. Particularly targeted are anticancer agents such as taxol (paclitaxel), doxorubicin and cisplatin.

Among the physical or chemical agents, particularly cited are radioactive isotopes and photo-sensitizers.

Among the photo-sensitizers, mention can be made of those belonging to the class of tetrapyrroles such as the porphyrins, bacteriochlorins, phthalocyanines, chlorines, purpurins, porphycenes, pheophorbides, or those belonging to the class of texaphyrins or hypericins. Among the first-generation photo-sensitizers mention can be made of hemato-porphyrin and a mixture of derivatives of hemato-porphyrin (HpD) (sold under the trade name Photofrin® by Axcan Pharma). Among the second-generation photo-sensitizers mention can be made of meta-tetra-hydroxyphenyl chlorin (mTHPC; trade name Foscan®, Biolitec AG) and the cycle A monoacid derivative of benzoporphyrin (BPD-MA sold under the trade name Visudyne® by QLT and Novartis Opthalmics). The formulations of second generation photo-sensitizers which associate a molecule therewith (lipid, peptide, sugar etc.) termed a transporter allowing their selective conveying to the tumour tissue are called third generation photo-sensitizers.

Among the biological agents, particular mention is made of peptides, proteins and saccharides.

Evidently the therapeutic agent can be formulated directly in its active form or in prodrug from. Also it is envisaged that several therapeutic agents are able to be formulated in association within the nanoemulsion.

The amount of therapeutic agent is dependent on the targeted application and the type of agent. However it is generally sought to formulate the nanoemulsion with a maximum concentration of therapeutic agent, in particular if they are scarcely soluble therapeutic agents to limit the volume and/or period of administration to the patient.

Yet it has been found that the presence of the solubilising lipid in the dispersed phase allows the incorporation of a high quantity of compounds even hydrophobic or amphiphilic compounds.

Core Proportion in the Droplets

In general the mole proportion of components in the core of the droplets relative to the components of the droplets is 10 to 80%, in particular 25 to 75%, preferably 33.35 to 73.99%. In other words, the mole proportion (mol/mol) of the whole (solubilising lipid/optional oil/optional imaging agent/optional lipophilic therapeutic agent) relative to the dispersed phase (i.e. to all the components of the dispersed phase) is generally 10 to 80%, in particular 25 to 75%, preferably 33.35 to 73.99%.

In general the weight proportion (wt/wt) of the core components of the droplets relative to the components of the droplets is 10 to 60%, in particular 20 to 60%, preferably 23.53 to 59.51%. In other words, the weight proportion of the whole (solubilising lipid/optional oil/optional tracer/optional lipophilic therapeutic agent) relative to the dispersed phase (i.e. to all the components of the dispersed phase) is generally 10 to 60%, in particular 20 to 60%, preferably 23.53 to 59.51%.

These mole and/or weight proportions are particularly adapted so that the «premix» formation is stable on storage, in particular stable when stored more than 28 days at 40° C., even more than 300 days at 40° C. Stability can measured in particular by monitoring the size of the droplets, their polydispersity index and/or their zeta potential (e.g. by dynamic light scattering using apparatus of type ZetaSizer, Malvern). This stability of the «premix» formulation is important for the envisaged applications. As detailed below, the «premix» formulation is used to prepare the «final» formulation comprising a nucleic acid that modulates endogenous mechanisms of RNA interference. It is of particular advantage to be able to store the «premix» formulation and to perform complexing with the said sequence just before use of the «final» formulation.

Aqueous Phase

The aqueous phase of the nanoemulsion used in the invention is preferably formed of water and/or a buffer such as a phosphate buffer e.g. PBS ("Phosphate Buffer Saline") or a saline solution in particular sodium chloride.

According to one embodiment, the continuous aqueous phase also comprises a thickening agent such as glycerol, a saccharide, oligosaccharide or polysaccharide, a gum or a protein, preferably glycerol. The use of a continuous phase of higher viscosity facilitates emulsification and thereby allows a reduction in sonication time.

The aqueous phase advantageously comprises 0 to 50% by weight, preferably 1 to 30% by weight and more particularly 5 to 20% by weight of thickening agent.

Evidently the aqueous phase may further contain other additives such as dyes, stabilisers and preserving agents in suitable amounts.

The proportion of dispersed phase and aqueous phase is most variable. However, most often the nanoemulsions are prepared with 1 to 50%, preferably 5 to 40% and more particularly 10 to 30% by weight of dispersed phase and 50 to 99%, preferably 60 to 95% and more particularly 70 à 90% by weight of aqueous phase.

Emulsion in which the Droplets are Covalently Bonded Together

In one embodiment, the formulation comprises a surfactant of following formula (I):

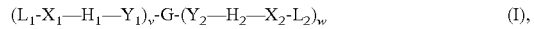

$$(L_1\text{-}X_1\text{—}H_1\text{—}Y_1)_v\text{-}G\text{-}(Y_2\text{—}H_2\text{—}X_2\text{-}L_2)_w \qquad (I),$$

where:

$L_1$ and $L_2$ are independently lipophilic groups;

$X_1$, $X_2$, $Y_1$, $Y_2$ and G are independently a linkage group;

$H_1$ and $H_2$ rare independently hydrophilic groups comprising a polyalkoxylated chain;

v and w are independently an integer from 1 to 8, and the droplets in the dispersed phase are covalently bonded together by the surfactant of formula (I).

The surfactant of formula (I) is partly contained in the continuous aqueous phase and partly in the dispersed phase.

The surfactant of formula (I) in fact comprises two lipophilic groups ($L_1$ and $L_2$) and two hydrophilic groups ($H_1$ and $H_2$). The hydrophilic groups are mostly located on the surface of the droplets, in the continuous aqueous phase, whereas the lipophilic groups are located inside the droplets of the formulation.

More specifically the lipophilic group $L_1$ is located inside some droplets and the group $L_2$ in adjacent droplets. The droplets are therefore covalently linked together by the group —$(X_1-H_1-Y_1)_v$-G-$(Y_2-H_2-X_2)_w$— of the surfactant of formula (I).

The groups $X_1$ and $X_2$ are linkage groups linking the lipophilic and hydrophilic groups. Group G is a linkage group between the two parts [lipophilic-hydrophilic] of the surfactant of formula (I). The groups $Y_1$ and $Y_2$ are linkage groups linking group G to these two parts [lipophilic-hydrophilic].

The formulation of this embodiment can advantageously be shaped (e.g. by placing in a mould or receptacle of given shape) and can remain in the desired shape depending on the desired application. This embodiment of the invention is therefore particularly adapted when the formulation is used in the form of a capsule, gel, ovule or patch.

In addition it resists dilution to an aqueous phase. More specifically, when an aqueous phase is added to this formulation, the formulation maintains its shape and is not diluted. In the medium, first the formulation comprising the droplets can be seen and secondly an aqueous phase essentially free of droplets.

Without wishing to be bound by any particular theory, it would seem that these properties of this formulation can be accounted for through the presence of the covalent bonds between the droplets, which impart very strong cohesion thereto.

In one embodiment, in above-mentioned formula (I):

$L_1$ and $L_2$ are independently selected from the group consisting of:
- an R or R—(C=O)— group, where R is a linear hydrocarbon chain having 11 to 23 carbon atoms;
- an ester or amide of fatty acids having 12 to 24 carbon atoms and phosphatidylethanolamine such as distearyl phosphatidylethanolamine (DSPE); and
- a poly(propylene oxide); and/or $X_1$, $X_2$, $Y_1$ and $Y_2$ are independently selected from the group consisting of:
- a single bond;
- a Z group selected from the group consisting of —O—, —NH—, —O(OC)—, —(CO)O—, —(CO)NH—, —NH(CO)—, —O—(CO)—O—, —NH—(CO)—O—, —O—(CO)—NH— and —NH—(CO)—NH;
- an Alk group being an alkylene comprising 1 to 6 carbon atoms; and
- a Z-Alk, Alk-Z, Alk-Z-Alk or Z-Alk-Z group where Alk and Z are such as defined above and where the two Z groups of the Z-Alk-Z group are the same or different; and/or $H_1$ and $H_2$ are independently selected from the group consisting of a poly(ethylene oxide) typically comprising 3 to 500 units of ethylene oxide, preferably 20 to 200 units of ethylene oxide; and/or G comprises at least one G' group having one of the following formulas (the groups $Y_1$ and $Y_2$ being linked on the left and right of the formulas described below):

 (XI)

 (XII)

 (XIII)

 (XIV)

 (XV)

 (XVI)

 (XVII)

 (XVIII)

 (XVIII')

 (XIX)

 (XX)

 (XXI)

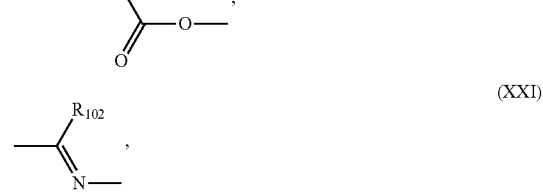

(XXII)

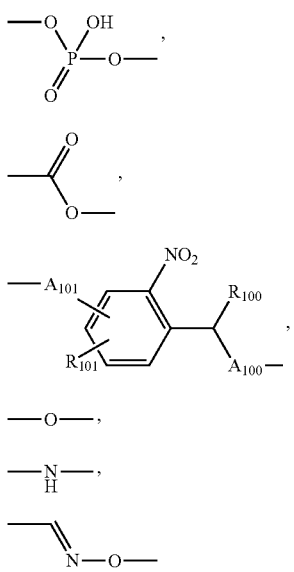

(XXIII)

(XXIV)

(XXV)

(XXVI)

(XXVII)

where $A_{102}$ represents CH or N, $R_{102}$ represents H or a linear hydrocarbon chain having 1 to 6 carbon atoms, $A_{101}$ represents —O—, —NH—(CO)— or —O—(CO)—, $R_{100}$ represents H or a methyl, $A_{100}$ represents —O— or —NH— and $R_{101}$ represents H, Me or —OMe.

By the formula

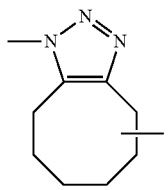

it is meant that the $Y_2$ group can be linked to any of the six atoms of the cyclooctyl and by the formula

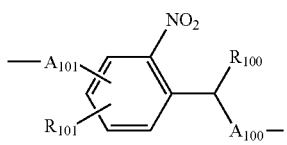

it is meant that the groups $A_{101}$ and $R_{101}$ can be linked to any of the four atoms of the phenyl.

In particular, v and w independently represent 1 or 2. Preferably v and w are 1.

The G group may comprise one or more G' groups defined above.

Therefore in a first embodiment the G group is formed of one G' group. In this embodiment, in formula (I), v and w represent 1.

In a second embodiment, the G group meets formula -G'-Y$_3$-G'- where:
Y$_3$ is a linkage group selected in particular from the group consisting of:
a single bond;
a Z group selected from the group consisting of —O—, —NH—, —O(OC)—, —(CO)O—, —(CO)NH—, —NH(CO)—, —O—(CO)—O—, —NH—(CO)—O—, —O—(CO)—NH— and —NH—(CO)—N;
an Alk group being an alkylene having 1 to 6 carbon atoms; and
a Z-Alk, Alk-Z, Alk-Z-Alk or Z-Alk-Z group where Alk and Z are such as defined above and where the two Z groups of the Z-Alk-Z group are the same or different;
each G' group independently represents a group of above-mentioned formulas (XI) to (XXVI and preferably the two G' groups of the formula -G'-Y$_3$-G'- are the same.

In this embodiment in formula (I), v and w represent 1.

This embodiment is of particular interest when the two G' groups are the same and comprise a cleavable function. It is then sufficient to cleave only one of the two functions to break the covalent bonds between the droplets of the formulation.

In a third embodiment, the G group is a dendrimer comprising (v+w) G' groups. The G group may in particular be a dendrimer comprising several G' groups, such as a dendrimer comprising a polyamidoamine group (PAMAM). For example the G group may have one of the following formulas (XXX) to (XXXIII) which comprise:

4 G' groups of formula (XXVI): v and w represent 2.

4 G' groups of formula (XXIV) where $R_{101}$ represents —O-Me, $A_{101}$ represents —NH—, $R_{100}$ represents a methyl and $A_{100}$ represents —NH—. v and w represent 2.

4 G' groups of formula (XIV). v and w represent 2.

16 G' groups of formula (XXVI). v and w represent 8.

(XXX)

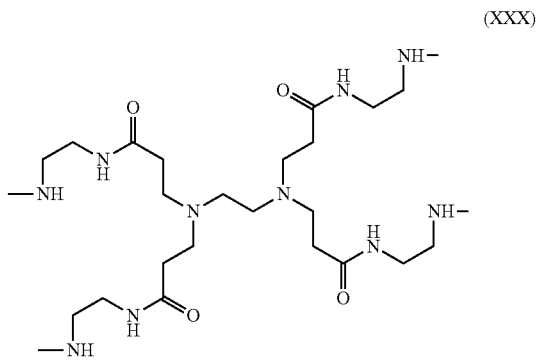

(XXXI) (Formula shown in original application)
(XXXII) (Formula shown in original application)
(XXXIII) (Formula shown in original application)

When $L_1$ and/or $L_2$ are an R—(C=O)— group where R represents a linear hydrocarbon chain having 11 to 23 carbon atoms, $L_1$ and/or $L_2$ represent groups derived from fatty acids having 12 to 24 carbon atoms.

By «$L_1$ and $L_2$ represent an ester or amide of fatty acids having 12 to 24 carbon atoms and phosphatidylethanolamine», it is meant that they represent a group of formula

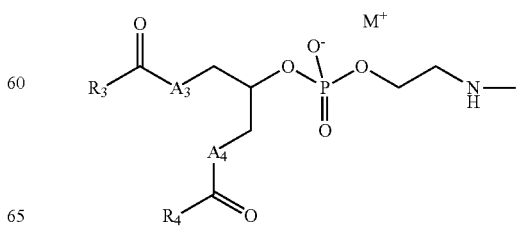

where:

$R_3$ and $R_4$ are independently a linear hydrocarbon chain having 11 to 23 carbon atoms;

$A_3$ and $A_4$ are O or NH; and

M is H or a cation.

Preferably, $L_1$ and $L_2$ are the same and/or $X_1$ and $X_2$ are the same and/or $H_1$ and $H_2$ are the same. Particularly preferred surfactants of formula (I) are those in which $L_1$ and $L_2$ are the same, $X_1$ and $X_2$ are the same, and $H_1$ and $H_2$ are the same. These surfactants are symmetrical compounds and are therefore generally easier to synthesize and hence less costly.

In one embodiment, in the abovementioned formula (I) the radicals $L_1$-$X_1$—$H_1$— and/or $L_2$-$X_2$—$H_2$— consist of one of the groups of the following formulas (the $Y_1$ or $Y_2$ group being linked on the right of the formulas described below):

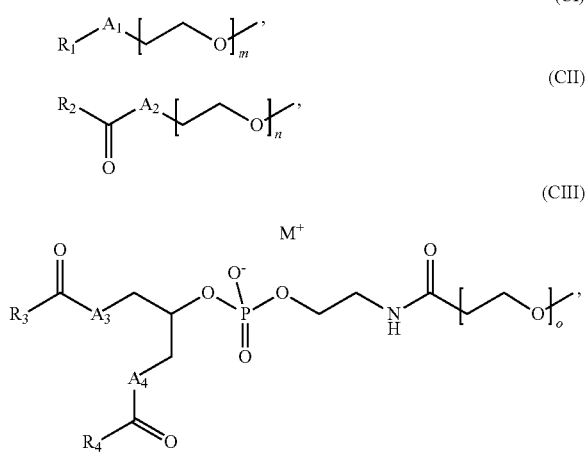

(CI)

(CII)

(CIII)

-continued

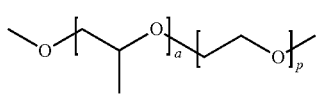

(CIV)

where:

$R_1$, $R_2$, $R_3$ and $R_4$ are independently a linear hydrocarbon chain having 11 to 23 carbon atoms;

$A_1$, $A_2$, $A_3$ et $A_4$ are O or NH;

m, n, o and p are independently integers from 3 to 500, preferably 20 to 200; and a is an integer from 20 to 120;

M is H or a cation.

The radicals $L_1$-$X_1$—$H_1$— and/or $L_2$-$X_2$—$H_2$— of formula (CII) are preferred. They are easy to prepare (in particular by formation of an ester or amide between a fatty acid and a derivative of poly(ethylene glycol). Also a formulation comprising a surfactant comprising a radical $L_1$-$X_1$—$H_1$— and/or $L_2$-$X_2$—$H_2$— of formula (CII) can generally be prepared with a larger amount of this surfactant than a formulation comprising a surfactant comprising a $L_1$-$X_1$—$H_1$— and/or $L_2$-$X_2$—$H_2$— radical of formula (CIII). The greater the proportion of surfactant of formula (I) in the formulation the greater the cohesion between the droplets and the more the formulation maintains its shape and resists dilution. Therefore these two properties can be further enhanced with a formulation comprising a surfactant comprising a $L_1$-$X_1$—$H_1$— and/or $L_2$-$X_2$—$H_2$— radical of formula (CII).

The radicals $L_1$-$X_1$—$H_1$— and/or $L_2$-$X_2$—$H_2$— of formula (CII) where $A_2$ represents NH are particularly preferred since the surfactants comprising such radicals can prevent leakage outside the droplets of optionally present lipophilic agents of interest in more efficient manner than the surfactants comprising $L_1$-$X_1$—$H_1$— and/or $L_2$-$X_2$—$H_2$— radicals of formula (CII) where $A_2$ represents O.

In one embodiment, in formula (I), v and w represent 1, $L_1$ and $L_2$ are independently R—(C=O)—, where R is a linear hydrocarbon chain having 11 to 23 carbon atoms, $H_1$ and $H_2$ are independently poly(ethylene oxide) comprising 3 to 500 units of ethylene oxide, $X_1$ and $X_2$ represent —O— or —NH—, G is formed of a G' group representing —S—S— (group of formula (XV) above) and $Y_1$ and $Y_2$ represent —CH$_2$—CH$_2$—NH—CO—CH$_2$—CH$_2$— (Alk-Z-Alk group above where Alk represents —CH$_2$—CH$_2$— and Z represents —NH—(CO)—) and the surfactant of the formulation then has following formula (I'):

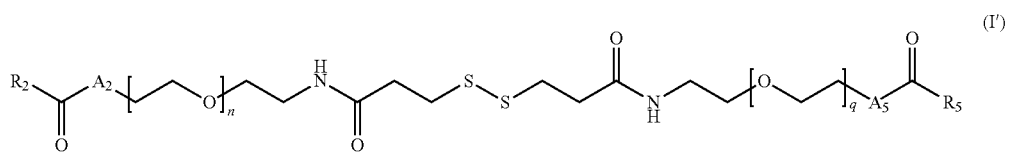

(I')

where:

$R_2$ and $R_5$ are independently a linear hydrocarbon chain having 11 to 23 carbon atoms preferably 17, $A_2$ and $A_5$ represent O or NH, preferably NH, and n and q are independently integers of 3 to 500, preferably 20 to 200.

In one embodiment, the groups $H_1$ and $H_2$ are independently selected from the group consisting of a poly(ethylene oxide) comprising more than 3 units of poly(ethylene oxide) even more than 20 units, in particular more than 50 (in the above-mentioned formulas m, n, o, p and/or q are preferably higher than 3, even 20, in particular higher than 50).

In one embodiment the G group of the surfactant in formula (I) of the formulation comprises a function that is cleavable, in particular at certain pH values (basic or acid pH), by enzymes, by light (visible light, ultraviolet or infrared) and/or over and above certain temperatures. In general the G group then includes a group G' comprising a cleavable function.

For example:
the β-ketoaminoester function of the G group in formula (XX) is cleavable at acid pH (typically at around 5),
the disulfide function of the G group in formula (XV) is cleavable under ultraviolet or with enzymes such as thioreductases,
the amide function of the G group in formula (XI) is cleavable with enzymes such as proteases,
the phosphate function of the G group in formula (XXII) is cleavable with enzymes such as phosphatases,
the imine function of the G groups in formulas (XXI) and (XIII) are cleavable at acid pH or over and above certain temperatures,
the cyclohexene crown of the G group in formula (XVII) is cleavable over and above certain temperatures (via retro Diels-Alder),
the carbonate function of the G group in formula (XIX) and the carbamate function of group G in formula (XII) are cleavable at acid pH.

Persons skilled in the art, in the light of their general knowledge, know which functions are cleavable and under which conditions. It is notably within their reach to select the function of the G' group of the surfactant in formula (I) so that it can be cleaved under the conditions encountered for administration of the formulation according to the invention.

Preferably the ratio of the weight of surfactant of formula (I) to the weight of the whole (surfactant of formula (I)/co-surfactant) is no lower than 15%. It has effectively been observed that such formulations are easier to prepare.

Size of the Droplets in the «Premix» Formulation

The droplets of the «premix» formulation defined above generally have a diameter of between 20 and 200 nm. In particular this diameter can be measured by dynamic light scattering on Malvern ZetaSizer apparatus.

It is possible to obtain droplets of more specific size by adapting the percentages of the components of the nanoemulsion.

For a formulation comprising droplets of size between 20 and 40 nm, preference is given to a formulation comprising at least 5 mole % of amphiphilic lipid, and:
  25 to 45 mole % of co-surfactant (below 25 mole % the formulation may exhibit stability problems); and/or
  15 to 50 mole % of cationic surfactant.

For a formulation comprising droplets of size between 40 and 100 nm, preference is given to a formulation comprising at least 5 mole % of amphiphilic lipid and:
  45 to 50 mole % of co-surfactant (below 45 mole %, the formulation may exhibit stability problems. Above 50% the transfecting efficacy of the «final» formulation after complexing with the nucleotide sequences is lower); and/or
  30 to 40 mole % of cationic surfactant (below 30 mole % the transfecting efficacy of the «final» formulation after complexing with the nucleotide sequences is lower. Over and above 40% the formulation may exhibit stability problems).

For a formulation comprising droplets of size between 130 and 175 nm, preference is given to a formulation comprising at least 5 mole % of amphiphilic lipid and 15 to 70 mole % of at least one cationic surfactant, and:
  10 to 25 mole %, in particular 10 to 15% of co-surfactant.

The mole percentages of amphiphilic lipid, of cationic surfactant and of co-surfactant are relative to the whole (amphiphilic lipid/cationic surfactant/co-surfactant/optional helper lipid).

Formulation Comprising a Nucleic Acid (Also Called «Final Formulation»)

By complexing the «premix» formulation defined above with a nucleic acid intended to be transfected, and optionally further with DNA tags, a «final» formulation is obtained useful for delivering said nucleic acid to cells.

Therefore the formulation in nanoemulsion form comprises a nucleic acid (i.e. a plurality of copies of at least one nucleic acid), and optionally further a single DNA tag.

Nucleic Acid (Intended to be Transfected)

The nucleic acids to be transfected and which are comprised in the formulation are DNA and/or RNA molecule.

In an embodiment, the nucleic acid is a single stranded DNA or RNA molecule. Preferably said single stranded nucleic acid comprises fewer than 200 bases.

In another embodiment, the nucleic acid is a double stranded DNA, RNA, or DNA/RNA molecule (one strand DNA, the other strand RNA). Preferably said double stranded nucleic acid comprises fewer than 200 base pairs.

In an embodiment, the nucleic acid comprises a cDNA sequence or antisense sequence.

In another embodiment, the nucleic acid consists in a messenger RNA (mRNA) sequence.

In still another embodiment, the nucleic acid is a nucleic acid which modulates endogenous mechanisms of RNA interference.

By "nucleic acid which modulates RNA interfering mechanisms", is meant an antisense nucleic acid which binds to an RNA target via RNA-RNA, RNA-DNA or protein-RNA interactions (Egholm et al., 1993, Nature, 365: 566) and alters the activity of the RNA target (for a review, see Stein and Cheng, 1993, Science, 261, 1004 and Woolf et al., U.S. Pat. No. 5,849,902).

Generally, a contiguous sequence of the antisense nucleic acid is complementary to a target sequence. However, in certain embodiments, the antisense nucleic acid may be bound to a substrate so that the substrate forms a loop or a hairpin structure, and/or the antisense nucleic acid may fold back so as to form a loop or a hairpin structure.

Thus, (i) the antisense nucleic acid may be complementary to 2, 3, 4, 5, 6, 7, 8, 9, 10, or more non-contiguous substrate sequences, and/or (ii) 2, 3, 4, 5, 6, 7, 8, 9, 10, or more portions of a non-contiguous sequence of the antisense nucleic acid may be complementary to the target sequence (for example, see Crooke, 2000, Methods Enzymol., 313: 3-45).

The antisense nucleic acid enters a cell route which is commonly called RNA interfering route (RNAi). The term of "interference by RNA" refers to selective intracellular degradation of RNA also known under the name of "gene silencing". The RNAi also includes repression of the translation by the small interfering RNAs (siRNA). The iRNA may for example be initiated by introducing a double-strand of long RNA (dsRNA) or siRNA.

In certain embodiments, said nucleic acid which may modulate RNA interfering mechanisms is:
  a small interfering RNA (siRNA) ("short-interfering RNA" or "small interfering RNA"),
  a blocked nucleic acid ("Locked Nucleic Acid" (LNA)),
  a microRNA (miRNA) ("MicroRNA2 or "miRNA"),
  a long double stranded RNA (dsRNA),
  a PIWI-interacting RNA (piRNA), or
  a small hairpin RNA (shRNA).

In one embodiment the said nucleotide sequences is a siRNA or shRNA.

A siRNA is a nucleotide sequence of double strand RNA. It is a natural or synthetic sequence. A siRNA is able to target a transcript of interest i.e. the nucleotide sequence of one of the strands of the siRNA is complementary to the nucleotide sequence of the transcript of interest. The size of each strand of the double stranded siRNA generally varies from 15 nucleotides to 50 nucleotides, preferably between 20 nucleotides and 35 nucleotides, still preferably between 21 nucleotides and 29 nucleotides or from 15 to 30 nucleotides, preferably 19 to 25 nucleotides, in particular 19 to 21 nucleotides.

The duplex portion of the siRNA may be part of a hairpin structure ("shRNA" or "short-hairpin RNA") which contains a loop between both sequences forming the duplex. The loop may vary in length. A shRNA is RNA molecule where typically less than about 50 nucleotides, preferably about 19 to about 23 nucleotides, is base paired with a complementary sequence located on the same RNA molecule, and where said sequence and complementary sequence are separated by an unpaired region of at least about 4 to about 15 nucleotides which forms a single-stranded loop above the stem structure created by the two regions of base complementarity. In certain embodiments, the length of the loop is of 5, 6, 7, 8, 9, 10, 11, 12, or 13 nucleotides.

Two deoxythymidines are generally added to the 3' portion of each of its strands to increase the stability thereof. Therefore a siRNA in which deoxythymidines have been grafted onto its 3' portion does not depart from the definition of a siRNA according to the present application. A siRNA allows a reduction in the expression of a target protein by interfering with the messenger RNA encoding this protein.

In one embodiment the said nucleotide sequence is a locked nucleic acid.

A locked nucleic acid is a nucleotide sequence of single strand RNA and/or DNA of which at least one of the nucleic acids contains a methylene bridge between the hydroxyl at position 2 and the carbon atom 4 of ribose. It is a synthetic nucleotide sequence. A locked nucleic acid is an inhibitor of microRNA and allows regulating of the expression of one or more target proteins the mRNA of which were in interference with the RNA sequences derived from the said microRNA. Regulation most often entails lifting of the inhibition of protein expression.

In one embodiment the said nucleotide sequence is a microRNA.

A microRNA is a nucleotide sequence of single strand RNA (in the order of 100 bases). It is a synthetic nucleotide sequence. A miRNA allows regulating of the expression of one or more target proteins by interference with one or more mRNAs respectively encoding these proteins. Regulation most often entails inhibition of the expression of the proteins.

In an embodiment, said nucleic acid is a dsRNA.

The term of "Long double-stranded RNA" (dsRNA) refers to an oligoribonucleotide or a polyribonucleotide, either modified or not, as well as in its fragments or portions, of genomic or synthetic origin or derived from the expression of an expression vector, which may be partly or totally double-stranded and for which the ends may be blunt ("blunt ended") or contain leaving ends in 5' and in 3', and which may also have a hairpin shape. In certain embodiments, the dsRNA has a size comprised between 250 bp to 2000 bp, preferably between 300 bp and 1000 bp. In certain embodiments, the dsRNA has a size of at least 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950, 1000, 1500 bp. In certain embodiments, the dsRNA has a size of at most 3000, 2500, 2000, 1500, 1000, 950, 900, 850, 800, 750, 700, 650, 600, 550, 500, 450, 400, 350, 300 bp.

In an embodiment, said nucleic acid is a piRNA.

piRNAs are small non-coding RNA in the typical size range of 26-32 or 33 nucleotides (ranges from 19-33 have been reported), typically with a U on the 5'-end and a 2'-OMethyl modified 3'-end and which form RNA-protein complexes through interactions with Piwi proteins.

Said nucleic acids are maintained on the surface of the droplets of the dispersed phase of the formulation by means of electrostatic interactions with the cationic surfactant. They are therefore located on the surface of the droplets at the crown part of the droplets on the hydrophilic side of the crown.

Apart from the optional binding of the siRNA to deoxythymidines mentioned above, said nucleic acids are not chemically modified and they are not denatured. In particular, said nucleic acids are not covalently bonded to the other components of the droplets. In particular said nucleic acids are not covalently bonded either to the co-surfactant, or to the amphiphilic lipid or to any optional imaging agent. Said nucleic acids are solely linked to the droplets of the nanoemulsion via electrostatic interactions with the cationic surfactants. This is of great advantage since said nucleic acids once released from their site of action are not denatured and can play their expected role. In addition, it is not necessary to prepare derivatives of nucleic acids which would be costly. Commercially available nucleic acids can therefore be complexed to the droplets without prior modification.

The droplets of the «final» formulation generally have a diameter of between 20 and 250 nm, typically between 40 and 200 nm, and preferably between 40 and 100 nm, still preferably between 40 and 60 nm. In particular this diameter can be measured by dynamic light scattering using Malvern ZetaSizer apparatus.

DNA Tag and Library of Formulations in Nanoemulsion Form

In one embodiment the "final" formulation in nanoemulsion form comprises a DNA tag.

By "DNA tag", is meant a specific double-stranded or single-stranded nucleotide sequence of a candidate molecule.

In certain embodiments, said DNA tag consists in a sequence of single-stranded DNA with at least 50, 55, 60, 65, 70, 75, 80, 85, 90, 95, 100 nucleotides, or of at most 100, 95, 90, 85, 80, 75, 70, 65, 60, 55, 50 nucleotides. In certain embodiments, said DNA tag consists in a sequence of double-stranded DNA with at least 50, 55, 60, 65, 70, 75, 80, 85, 90, 95, 100 base pairs (bp), or with at most 100, 95, 90, 85, 80, 75, 70, 65, 60, 55, 50 bp.

According to an embodiment of the invention, a plurality of formulations in nanoemulsion form is used, each formulation in nanoemulsion form comprising:
a different nucleic acid intended to be transfected,
optionally a tracer, and
a single DNA tag specific to said nucleic acid intended to be transfected,
thereby forming a library of formulations in nanoemulsion form containing a nucleic intended to be transfected.

Preferably, the formulation in nanoemulsion form comprises a tracer, in particular when present in a library of formulations.

According to an embodiment, the premix formulations of each final formulation forming said library of formulations in nanoemulsion form are identical, the final formulations of the library differing from one another only by the nature of the nucleic acid intended to be transfected, optional tracer, and single DNA tag specific to said nucleic acid intended to be transfected.

According to another embodiment, the premix formulations of each final formulation forming said library of formulations in nanoemulsion form are not identical, and further differ from one another by the nature of the nucleic acid intended to be transfected, optional tracer, and single DNA tag specific to said nucleic acid intended to be transfected.

Preferably, in the library of formulations in the nanoemulsion form to be used according to the invention, said single DNA tag consists in a sequence of DNA, preferably double-stranded DNA, with at least 50 nucleotides or bp consisting in, on a strand and in the 5'-3' sense:
- a first sequence of at least 20 nucleotides common to all the single DNA tags of the library,
- a single sequence of at least 10 nucleotides specific to the candidate molecule as defined above,
- a second sequence of at least 20 nucleotides common to all the single DNA tags of the library.

Said first and second sequences are notably useful for amplifying and/or sequencing said single DNA tag. For this purpose, it is preferable that said first or second sequences have a nucleotide sequence which does not exist in the genome of the cell, of the tissue or of the organism from which stems the cell put into contact with the library of formulations in nanoemulsion form. For example, (i) when the cell put into contact with the library of formulations in nanoemulsion form is a human cell, said first and second sequences are not part of the human genome; (ii) when the cell put into contact with the library of formulations in nanoemulsion form is a cell of an animal, such as a rodent (rat, mouse) cell, said first and second sequences are not part of the genome of said animal; (iii) when the cell put into contact with the library of formulations in nanoemulsion form is a cell of a plant, said first and second sequences are not part of the genome of said plant. Preferably, said first or second sequences comprise at least 1, 2, 3, 4, 5, 6, or more of modified nucleotides. For example, said first and second sequences comprise at least 1, 2, 3, 4, 5, 6, or more of inosine.

In certain embodiments, said first and second sequences are identical or different, preferably said first and second sequences are different. This gives the possibility of using a single pair of primers for the whole of the tags, during the amplification step. In certain embodiments, said first and second sequences have a length of at least 20, 25, 30, 35, 40, 45, 50 nucleotides, or of at most 50, 45, 40, 35, 30, 25, 20 nucleotides.

By "single sequence of at least 10 nucleotides specific to the candidate molecule", is meant a sequence associated in silico to a determined nucleic acid intended to be transfected. The "single DNA tag" containing said single sequence of at least 10 nucleotides specific to the candidate molecule is thereby also rendered specific to the nucleic acid intended to be transfected.

Thus, in a library of nanoparticles, each candidate molecule is associated with a single sequence of at least 10 nucleotides and may be identified by means of this single sequence contained in the single DNA tag. In certain embodiments, said single sequence specific to the candidate molecule has a length of at least 10, 11, 12, 13, 14, 15, 16, 17, 18, 19, 20, 21, 22, 23, 24, 25, 30, 35, 40, 45, 50 nucleotides, or at most 50, 45, 40, 35, 30, 25, 24, 23, 22, 21, 20, 19, 18, 17, 16, 15, 14, 13, 12, 11, 10 nucleotides.

In certain embodiments, the single sequence has a nucleotide sequence which does not exist in the genome of the cell, of the tissue or of the organism from which stems the cell put into contact with the library of formulations in nanoemulsion form. For example, (i) when the cell put into contact with the library of formulations in nanoemulsion form is a human cell, said single sequence is not part of the human genome; (ii) when the cell put into contact with the library of formulations in nanoemulsion form is a cell of an animal, such as a rodent cell (rat, mouse), said single sequence is not part of the genome of said animal; (iii) when the cell put into contact with the library of formulations in nanoemulsion form is a cell of a plant, said single sequence is not part of the genome of said plant. Preferably, said single sequence comprises at least 1, 2, 3, 4, 5, 6, or more of modified nucleotides. For example, said single sequence comprises at least 1, 2, 3, 4, 5, 6, or more of inosine.

The synthesis of said single DNA tags may be carried out with methods known to one skilled in the art.

In certain embodiments, the library of formulations in nanoemulsion form comprises or consists in at least 2, 10, 50, 100, 250, 500, 1000, 2500, 5000, 7500, 10,000, 12,500, 15,000, 20,000, 30,000, 50,000, 75,000, 100,000, or more formulations in nanoemulsion form as defined above. In certain embodiments, said library comprises or consists in a number of formulations in nanoemulsion form comprised between 2 and 100,000, preferably between 500 and 50,000, still preferably between 1000 and 15,000.

In certain embodiments, said library of formulations in nanoemulsion form comprises or consists in a number of formulations in nanoemulsion form at least equal to the number of nucleic acids intended to be transfected present in a collection of molecules commercially available, i.e., there exists at least one copy of each type of formulations, the type being defined by the combination of the nucleic acid intended to be transfected, the optional tracer and the single DNA tag.

In certain embodiments, said library of formulations in nanoemulsion form comprises or consists in at least 1, 2, 10, 50, 100, 250, 500, 1000, 2500, 5000, 7500, 10,000, 20,000, 50,000, 75,000, 100,000 type(s) of formulations in nanoemulsion form, each type of formulations in nanoemulsion form being present in a number of copies at least equal to 10, 50, 100, 500, 1000, 2000, 5000, 7500, 10,000, 15,000, 20,000 nanoparticles.

As non-limiting examples of a collection of nucleic acids intended to be transfected, and in particular of nucleic acids which modulates endogenous mechanisms of RNA interference, mention may notably be made of the collection of 1292 siRNAs from Qiagen targeting 646 kinases (Human Kinase siRNA set V1.0; Ref. 1027091), or the collection of 2375 siRNAs from Qiagen targeting 1183 genes involved in cancers (Human Cancer siRNA set V2.0), or the collection of 278 siRNAs targeting 139 genes involved in cancers (Human Cancer siRNA set V1.0; Ref. 1022171), or the collection of 91,800 siRNAs from Qiagen targeting 22,950 human genes (Human Genome Wide siRNA set), or the collection of 982 LNAs from Exiqon targeting all the known human miRNAs (miRCURY LNA Human microRNA Inhibitor Library; Ref. 190102-2).

As a non-limiting example, said library of formulations in nanoemulsion form comprises or consists in 1292 formulation in nanoemulsion form, each formulation in nanoemulsion form comprising one of the siRNAs of the collection of 1292 siRNAs from Qiagen targeting 646 kinases, a tracer and a single DNA tag specific to said siRNA; or said library of formulations in nanoemulsion form comprises or consists in 2375 formulations in nanoemulsion form, each formulation in nanoemulsion form comprising one of the siRNAs of the collection of 2375 siRNAs from Qiagen targeting 1183 genes involved in cancers, a tracer and a single DNA tag specific to said siRNA; or said library of formulations in nanoemulsion form comprises or consist in 278 formulations in nanoemulsion form, each formulation in nanoemulsion form comprising one of the siRNAs of the collection of 278 siRNAs targeting 139 genes involved in cancers, a tracer and a single DNA tag specific to said siRNA; or said library of formulations in nanoemulsion form comprises or consists in 91,800 formulations in nanoemulsion form, each formulation in nanoemulsion form comprising one of the siRNAs of the collection of 91,800 siRNAs from Qiagen targeting 22,950 human genes, a tracer and a single DNA tag specific to said siRNA; or said library of formulations in nanoemulsion form comprises or consists in 982 formulations in nanoemulsion form, each formulation in nanoemulsion form comprising one of the LNAs of the collection of 982 LNAs from Exiqon targeting all the known human miRNAs, a tracer and a single DNA tag specific to said LNA.

Biological Ligand for Targeting a Cell and/or an Organ

Examples of targeting biological ligands include, without limitation, an antibody, a peptide, a saccharide, an aptamer, an oligonucleotide or a compound like folic acid.

According to an embodiment, said targeting biological ligand is grafted at the surface with an amphiphilic compound, notably with the co-surfactant, of the droplet of the formulation in the form of a nanoemulsion comprising a continuous aqueous phase and at least one dispersed phase as defined above. The nanoemulsion then comprises a grafted co-surfactant. In this case, the co-surfactant plays the role of a spacer allowing accommodation of the targeting biological ligand at the surface. For example, when the biological ligand is a peptide comprising one or more cysteines, the grafting to the alkylene oxide chain of the surfactant may be ensured by thiol-maleimide coupling.

Localisation of the Components of the Nanoparticles

In the formulation in the form of a nanoemulsion comprising a continuous aqueous phase and at least one dispersed phase as defined above, the negatively charged nucleic acid intended to be transfected and said (single) DNA tag are maintained at the surface of the droplets of the dispersed phase of the formulation by means of the electrostatic interactions with the cationic surfactant, i.e., they are therefore localised at the surface of the droplets, at the crown of the droplets, on the hydrophilic side of the crown, and the tracer when present is localised in the core of the droplets.

Figure 1:
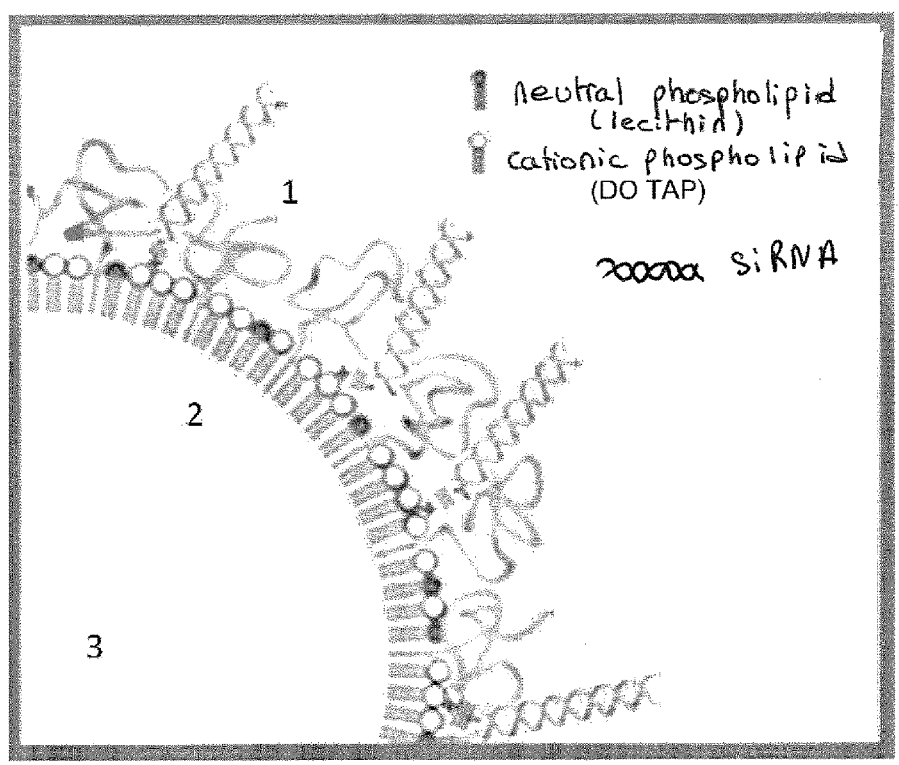
FIG. 1 gives a schematic illustrating the core/ring structure of a droplet of a formulation according to the invention («final» formulation with a nucleic acid that modulates endogenous mechanisms of RNA interference). 1 represents the continuous aqueous phase, 2 the crown (in part) of the droplet and 3 the core (in part) of the droplet. In the crown 2 are illustrated: the amphiphilic liquid (e.g. neutral phospholipid such as lecithin), the cationic surfactant (e.g. cationic phospholipid DOTAP), the co-surfactant of which the folding poly(ethylene oxide) chain is represented in the aqueous phase and the double strand nucleic acid that modulates endogenous mechanisms of RNA interference (e.g. siRNA).

Accordingly as illustrated in FIG. 1, the droplets of the formulation according to the invention are organised in the form of a core-crown, wherein:
the core comprises:
the solubilizing lipid,
the optional oil,
the optional tracer,
optional therapeutic agent if it is lipophilic
the crown comprises:
the amphiphilic lipid,
the cationic surfactant,
the co-surfactant (optionally grafted with a molecule of interest),
the nucleic acid intended to be transfected,
the optional(single) DNA tag,
the optional fusogenic lipid,
the optional surfactant of formula (I),
the optional targeting biological ligand.

In addition to the optional binding of the siRNAs to the deoxythymidines mentioned above, said nucleic acids are not chemically modified and they are not denatured. In particular, said nucleic acids are not covalently bound to the nanoparticles. Notably, said nucleic acids are not covalently bound either to the co-surfactant, or to the amphiphilic lipid, or to the optional imaging agent. Indeed, said nucleic acids are only bound to the droplets of the nanoemulsion by electrostatic interactions with the cationic surfactants. This is highly advantageous since said nucleic acids, once released in their site of action, are not denatured and may play the expected role. Further, it is not necessary to prepare derivatives of nucleic acids, which is costly. The nucleic acids available commercially may therefore be complexed to the droplets without any modification beforehand.

Preparation Method

The method for preparing the above-defined formulation is typically carried out as explained below.

Typically, the different oil constituents are first mixed to prepare an oily premix for the dispersed phase of the emulsion, and it is then dispersed in an aqueous phase under shear effect.

The preparation method typically comprises the following steps:
(vi) preparing an oil phase comprising a solubilising lipid, an amphiphilic lipid, the cationic surfactant;
(vii) preparing an aqueous phase optionally comprising the co-surfactant;
(viii) dispersing the oil phase in the aqueous phase under the action of sufficient shear to form a «premix» formulation; then
(ix) adding nucleic acids intended to be transfected to the formed «premix» formulation; then
(x) recovering the formulation thus formed.

Step (i)

In general the preparation of the oil phase comprises the mixing of the oily components of the formulation (solubilising lipid/amphiphilic lipid/cationic surfactant). If the formulation comprises a lipid able to facilitate cytosolic release via destabilisation of the endosomal membrane, and/or an oil, and/or an imaging agent, and/or a therapeutic agent, these are generally added to the oil phase at step (i).

Mixing can optionally be facilitated by placing one of the constituents or the complete mixture in solution in a suitable organic solvent. The organic solvent is then evaporated to obtain a homogenous oily premix for the dispersed phase.

Also, it is preferable to conduct the pre-mixing (step (i)) at a temperature at which all the ingredients are liquid.

Step (iii)

Advantageously the oil phase is dispersed in the aqueous phase in the liquid state. If one of the phases solidifies at ambient temperature, it is preferable to perform mixing by heating one or preferably both phases to melting temperature or higher.

Emulsification under shear effect is preferably performed using a sonicator or microfluidiser. Preferably the aqueous phase and then the oil phase are added in the desired proportions to a cylindrical container and the sonicator is immersed in the centre thereof and set in operation for sufficient time to obtain a nanoemulsion, most often for a few minutes.

At the end of step (iii), a homogeneous nanoemulsion is generally obtained in which:
the mean diameter of the oil droplets is generally greater than 10 nm and smaller than 200 nm, preferably between 30 and 190 nm; and the zeta potential is higher than 20 mV, generally between 25 mV and 60 mV, preferably between 40 and 55 mV, preferably when the aqueous phase of the formulation is a 0.15 mM aqueous solution of NaCl.

The nanoemulsion obtained at the end of step (iii) corresponds to the «premix» formulation defined above.

Step (iv)

Step (iv) then allows the preparing of the formulation used to deliver the said nucleotide sequences, by complexing the said nucleic acids on the «premix» formulation obtained at the end of step (iii).

In general the nucleic acids are added to the formed nanoemulsion and the mixture obtained is mixed at ambient temperature e.g. for 30 minutes.

At step (iv), the nucleic acids intended to be transfected, carrying negatively charged phosphate groups, are linked via electrostatic bonds to the droplets of which the surface is positively charged by means of the cationic groups of the cationic surfactants. Complexes are thus formed between the nucleic acids and the droplets of the nanoemulsion. The nucleic acids are generally added to the aqueous phase e.g. water free of nucleases, cell culture media, cell media optimised for transfection in particular Opti-MEM medium, or buffer solutions and in particular 4-(2-hydroxyéthyl)-1-piperazine ethane sulfonic acid (HEPES). Step (iv) is typically conducted at ambient temperature (25° C.), under simple homogenisation or agitation (e.g. between 100 and 1000 rpm) for a time of between 5 minutes and 2 hours, for example in the order of 30 minutes.

Preferably at step (iv), the quantity of added nucleic acids is such that the ratio between the amount of positive charges due to the cationic surfactant in the «premix» formulation and the amount of negative charges provided by the nucleotide sequences added to the medium is higher than 8:1. It is within the reach of persons skilled in the art to calculate the amount of negative charges provided by the nucleic acids added to the medium and the amount of positive charges due to the cationic surfactant in the «premix» formulation. A said ratio allows quantitative complexing to be obtained i.e. there no longer remain in the medium any free nucleic acids.

Step (iv) can be monitored by various methods, for example by:

agarose gel electrophoresis which allows observation of the migration of the nucleic acids. With good complexing, the nucleic acids are heavier and can be seen in the wells. With lesser complexing, free nucleic acids will migrate to another position.

dynamic light scattering (DLS), by observing the impact of complexing on hydrodynamic diameter. The more complexing is efficient the more the profile tends towards monomodal distribution.

At the end of step (iv), a homogeneous nanoemulsion is generally obtained in which the mean diameter of the oil droplets is generally greater than 10 nm and smaller than 200 nm, preferably between 60 and 200 nm.

Advantageously the method for preparing the formulation does not require chemical modification of the nucleic acids, and in particular does not require covalent grafting thereof onto another component of the formulation. It is therefore very easy to prepare numerous formulations of the invention in parallel containing nucleic acids.

Optional Subsequent Steps

The formulation can be purified, for example by column purification or dialysis.

Before packaging, the emulsion can be diluted and/or sterilised, for example by filtration or dialysis. This step allows the removal of any aggregates which may have been formed during preparation of the emulsion.

The emulsion thus obtained is ready for use, optionally after dilution.

Preparation of a Formulation Comprising a Surfactant of Formula (I)

In the embodiment in which the formulation comprises a surfactant of formula (I), the nanoemulsion used for complexing with the nucleic acids intended to be transfected can be prepared using a method comprising the contacting of:

an emulsion 1 comprising a continuous aqueous phase and a dispersed phase in the form of droplets comprising an amphiphilic lipid and a surfactant of following formula (LI):

$L_1$-$X_1$—$H_1$—$Y_1$-$G_1$ (LI), with an emulsion 2 comprising a continuous aqueous phase and a dispersed phase in the form of droplets comprising an amphiphilic lipid and a surfactant of following formula (LII):

$G_2$-$Y_2$—$H_2$—$X_2$-$L_2$ (LII)

where $L_1$, $X_1$, $H_1$, $Y_1$, $L_2$, $X_2$, $H_2$ and $Y_2$ are such as defined above, and $G_1$ and $G_2$ are groups able to react to form group G such as defined above, under conditions allowing the reaction of the surfactants of formulas (LI) and (LII) to form the surfactant of formula (I) such as defined above, after which covalent bonds between the droplets in the dispersed phase are formed.

The continuous aqueous phases of emulsions 1 and 2 comprise a co-surfactant such as defined above. The dispersed phases of emulsions 1 and 2 comprise a solubilising lipid such as defined above. The dispersed phase of emulsion 1 and/or the dispersed phase of emulsion 2 comprises a cationic surfactant such as defined above.

When group G comprises a single G' group, the groups $G_1$ and $G_2$ are typically groups able to react with one another to form group G.

When group G comprises several G' groups, the emulsions 1 and 2 are generally contacted with a compound able to react with the surfactants of formulas (LI) and (LII) to form group G. This compound typically comprises at least a v number of $G'_1$ functions able to react with group $G_1$ and a w number of $G'_2$ functions able to react with group $G_2$.

Therefore in the embodiment in which the G group meets formula -G'-$Y_3$-G'- defined above, the method for preparing the formulation typically comprises the contacting of:

an emulsion 1 such as defined above;

and an emulsion 2 such as defined above;

with a compound of formula $G'_1$-$Y_3$-$G'_2$ where $Y_3$ is such as defined above, $G'_1$ is a group able to react with $G_1$ to form the first group G' such as defined above and $G'_2$ is a group able to react with $G_2$ to form the second group G' such as defined above (of same or different type to the first group G'), under conditions allowing reaction of the surfactants of formulas (LI) et (LII) and of the compound of formula $G'_1$-$Y_3$-$G'_2$ to form the surfactant of formula (I) in which group G meets formula -G'-$Y_3$-G'-defined above, after which covalent bonds are formed between the droplets of the dispersed phase.

Similarly in the embodiment defined above in which the G group is a dendrimer comprising (v+w) G' groups, the method for preparing the formulation typically comprises the contacting of:

an emulsion 1 such as defined above;

an emulsion 2 such as defined above;

with a dendrimer of formula $(G'_1)_v$—$Y_4$-$(G'_2)_w$ in which v and w are such as defined above, $G'_1$ is independently a group able to react with $G_1$ to form a G' group such as defined above and $G'_2$ is independently a group able to react with $G_2$ to form a group G' such as defined above (each G' being of same or different type to the other G' groups) and $Y_4$ is the backbone of a dendrimer, under conditions allowing the reaction of the surfactants of formulas (LI) and (LII) and of the dendrimer of formula $(G'_1)_v$—$Y_4$-$(G'_2)_w$ to form the surfactant of formula (I) in which group G is a dendrimer comprising (v+w) groups G', after which covalent bonds are formed between the droplets of the dispersed phase.

For example, to form a group G of formula (XXX), (XXXI), (XXXII) and (XXXIII), the compound of formula $(G'_1)_v$—$Y_4$-$(G'_2)_w$ can respectively have one of the following formulas (XXX'), (XXXI'), (XXXII') and (XXXIII'):

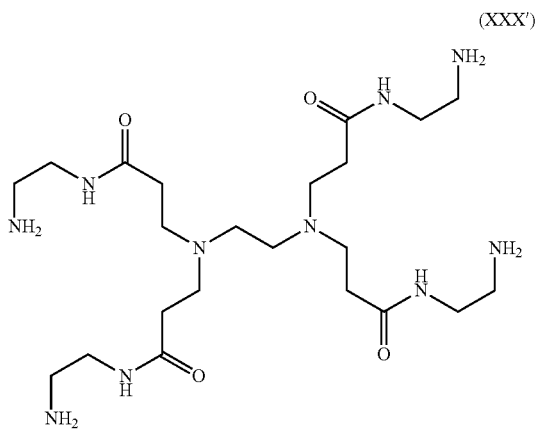 [SMILES: NCCNC(=O)CCN(CCC(=O)NCCN)CCN(CCC(=O)NCCN)CCC(=O)NCCN]

(XXX')

(where $G'_1$ and $G'_2$—represent $NH_2$ and v and w represent 2), (XXXI') (Formula shown in original application)
(where $G'_1$ and $G'_2$-represent $NH_2$ and v and w represent 2), (XXXII') (Formula shown in original application)
(where $G'_1$ and $G'_2$—represent

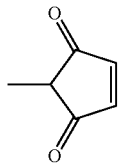

and v and w represent 2), (XXXIII') (Formula shown in original application)
(where $G'_1$ and $G'_2$—represent $NH_2$ and v and w represent 8).

In the light of their general chemistry knowledge, persons skilled in the art are able to select the type of groups $G'_1$, $G'_2$, $Y_3$, $Y_4$, $G_1$ and $G_2$ to be used to form group G and the conditions allowing the reaction. The usual reactions of organic chemistry can be used in particular those described in «Comprehensive Organic Transformations: A Guide to Functional Group Preparations» by Richard C. Larock published by John Wiley & Sons Inc, and the references cited therein. Therefore the examples of groups $G_1$ and $G_2$ below are given by way of illustration and are non-limiting.

Typically when group G is formed of one G' group, the groups $G_1$ and $G_2$ of the compounds of formulas (LI) and (LII) can be chosen as follows for example:

$G_1$ is a thiol (—SH) and $G_2$ is:
either a maleimide, a surfactant of formula (I) then being formed in which G comprises a G' group representing a group of formula (XIV) where $A_{102}$ represents N;
or a vinylsulfone, a surfactant of formula (I) then being formed in which G comprises a G' group representing a group of formula (XVI);
or a —S—S-pyridinyl or —SH group, a surfactant of formula (I) then being formed in which G comprises a G' group representing a group of formula (XV);

$G_1$ is a hydroxyl and $G_2$ is —COOH or an activated ester, a surfactant of formula (I) then being formed in which G comprises a group G' representing a group of formula (XXIII);

$G_1$ is an amine —$NH_2$ and $G_2$ is —COOH or an activated ester, a surfactant of formula (I) then being formed in which G comprises a group G' representing a group of formula (XI);

$G_1$ is a hydroxyl and $G_2$ is an activated carbonate, a surfactant of formula (I) then being formed in which G comprises a group G' representing a group of formula (XIX);

$G_1$ is an amine —$NH_2$ and $G_2$ is an activated carbonate, a surfactant of formula (I) then being formed in which G comprises a group G' representing a group of formula (XII);

$G_1$ is an amine —$NH_2$ and $G_2$ is a —CHO aldehyde, a surfactant of formula (I) then being formed in which G comprises a group G' representing a group of formula (XXI);

$G_1$ is a hydrazide of formula —(C=O)—NH—$NH_2$ and $G_2$ is a —(C=O)—$R10_2$ group, a surfactant of formula (I) then being formed in which G comprises a group G' representing a group of formula (XIII);

$G_1$ is an alkyne and $G_2$ is an azide, a surfactant of formula (I) then being formed in which G comprises a group G' representing a group of formula (XVIII);

$G_1$ is a cyclooctyne and $G_2$ is an azide, a surfactant of formula (I) then being formed in which G comprises a group G' representing a group of formula (XVIII');

$G_1$ is a furan and $G_2$ is a maleimide, a surfactant of formula (I) then being formed in which G comprises a group G' representing a group of formula (XVII);

$G_1$ is an aldehyde and $G_2$ is an amine, a surfactant of formula (I) then being formed in which G comprises a group G' representing a group of formula (XXI);

$G_1$ is a phosphate of formula —O—P(=O)(OH)$_2$ and $G_2$ is a hydroxyl, a surfactant of formula (I) then being formed in which G comprises a group G' representing a group of formula (XXII);

$G_1$ is a good leaving group LG and $G_2$ is a group of following formula

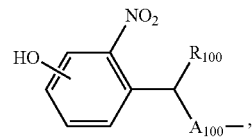

a surfactant of formula (I) then being formed in which G comprises a group G' representing a group of formula (XXIV) in which $A_{101}$ is O;

$G_1$ is a hydroxyl or —$NH_2$ amine and $G_2$ represents a group of following formula

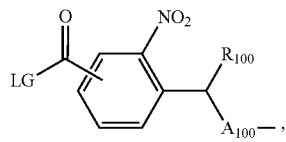

a surfactant of formula (I) then being formed in which G comprises a group G' representing a group of formula (XXIV) in which $A_{101}$ respectively represents —O—(CO)— or —NH—(CO);

$G_1$ is a good leaving group LG and $G_2$ is a hydroxyl, a surfactant of formula (I) then being formed in which G comprises a G' group representing a group of formula (XXV);

$G_1$ is a good leaving group LG and $G_2$ is an amine —$NH_2$, a surfactant of formula (I) then being formed in which G comprises a group G' representing a group of formula (XXVI);

$G_1$ is an oxyamine —O—$NH_2$ and $G_2$ is an aldehyde, a surfactant of formula (I) then being formed in which G comprises a group G' representing a group of formula (XXVII).

When group G comprises several groups G', the choice of groups reacting together: $G'_1$ and $G_1$, $G'_2$ and $G_2$ can be made in the same manner by replacing groups $G_1$ or $G_2$ in the above-mentioned examples with $G'_1$ or $G'_2$.

The emulsions 1 and 2 used in the method can be prepared using the first method described above comprising steps (i), (ii), (iii) and (v) (and not performing step (iv) to add the nucleotide sequences able to modulate endogenous mechanisms of RNA interference).

Preparation of a library of formulations in nanoemulsion form is typically carried out according to the following steps: (i) preparation and composition of a formulation in the form of a nano-emulsion, comprising a continuous aqueous phase and at least one dispersed phase, (ii) encapsulation or complexation of the tracer, (iii) complexation of the DNA tag, (iv) encapsulation or complexation of the nucleic acid intended to be transfected. The steps (i) to (iv) may notably be carried out according to the methods described in Example 1 in paragraphs 1.1, 1.5, 1.4 and 1.2, respectively.

Eukaryotic Cells

The cells used in the methods or 3D scaffold according to the invention are eukaryotic cells. The cells may be primary cells or immortalized cells. Examples of eukaryotic cells which may be used in the invention are cells of mammals, preferably human cells, or plant cells. Mammalian cells may for example be lymphoid cells, embryo cells, fetal cells, epithelial cells, myeloid cells, tumoural cells, in particular solid tumour cells, adult or embryo stem cells, cells infected by a virus, a bacterium, a fungus or a parasite. Preferably, the cells are human cells, including those from healthy donors. Still preferably, the cells are tumoural cells or cells infected by a virus. Said tumoural cells may stem from tumours at various evolutionary stages and/or tumours having different sensitivities to anticancer therapies. As a non-limiting example, the tumoural cells may be cells from breast, prostate, brain cancer (neuroblastoma, astrocytoma, oligodendroglioma), kidney, liver cancer (hepatocarcinoma), pancreas, adrenal gland, colon cancer, colorectal cancer, cancer of the ovaries, of the testicles, of the uterus, of the lungs, a carcinoma, a sarcoma, a lymphoma, a myeloma, a haematopoietic cancer, leukaemia, a melanoma.

The plant cells may be cells from a monocotyledonous plant or a dicotyledonous plant. For example, the plant cells may stem from the leaves, from the stem, from the root, from an embryo, from a shoot.

The cells used in the methods and culture according to the invention are in a three-dimensional environment, i.e. in a natural or synthetic 3D scaffold. In an embodiment the eukaryotic cells in 3D scaffold are eukaryotic cells cultivated in and/or on a three-dimensional biocompatible polymeric matrix. In another embodiment, eukaryotic cells in 3D scaffold are eukaryotic cells embedded in native extracellular matrix, i.e. said eukaryotic cells in 3D scaffold consist of a biological sample (preferably solid sample) comprising eukaryotic cells embedded in extracellular matrix.

Three-Dimensional Environment

In the frame of the method and 3D scaffold of the invention, the eukaryotic cells are in three-dimensional scaffold, e.g. in 3D culture.

The three-dimensional culture, or 3D culture, is based on the use of a 3D scaffold on and/or in (in particular, on and in) which the cells are seeded and on which they can adhere. The support helps to guide the growth and proliferation of cells in a 3D configuration. The 3D scaffold may be made from a variety of materials, for example of polymer materials forming a hydrogel or a porous inert matrix. The seeded cells are then fixed and grow within the pores of the scaffold. Bioactive agents, such as components of the extracellular matrix, particularly collagen, and/or growth factors can also be used to improve the function of the scaffold and allow greater cell adhesion, cell polarity and induce a tissue organization. The three-dimensional hydrogel cultures are typically performed on media containing animal products (Matrigel®, collagen), plant products (alginate/agarose) or synthetic products.

Matrigel® is the 3D culture medium the most commonly used. It is sold by many distributors. It is a soluble preparation of an extract of basement membrane of Engelbreth-Holm-Swarm (EHS) mouse sarcoma containing laminin (about 60%), collagen IV (about 30%), entactin (about 8%), and growth factors whose content may be variable according to the Matrigel® preparation. Growth factors typically present include heparan sulfate proteoglycans (perlecan), TGF-β, EGF, IGF, FGF, TPA, and other growth factors existing naturally in the EHS tumor. Matrigel® may also contain matrix metalloproteinases (MMPs). Matrigel® is generally used at 8-11% (8-11 mg/ml of culture medium). It is liquid/viscous at 2-6° C. and begins to gel at 10° C. It rapidly forms a gel at 37° C.

A hydrogel of collagen can also be used for the three-dimensional culture. 3D collagen matrix is formed by polymerization of collagen fibrils from monomers of type I collagen. Fibril formation is initiated by neutralizing the pH of an acidic solution of collagen type I (usually dissolved in HCl 0.02N) to pH 7.1-7.4 and bringing the solution to 20-37° C. The concentration of collagen I monomers used for the polymerization determines the density of the matrix and the pore size. Solutions of collagen type I of concentrations ranging from 1 to 7 mg/ml can be typically used.

Alternatively, polymers derived from plants can be used for 3D microfluidic culture. For example, for the culture alginate matrix, the cells are suspended in a solution of sodium alginate and poured dropwise into a calcium chloride bath. Calcium ions trigger crosslinking of alginate monomers and encapsulation of the cells in droplets whose size can be controlled. In particular, for the alginate droplets used in the frame of the invention, core of droplets preferably comprises a hydrogel.

Synthetic hydrogels mimicking the extracellular matrix are also available.

The QGel® matrix, from the society Qgel, is for example composed of PEG molecules that can be functionalized with the RGD motif that mediates cell attachment. These hydrogels are described in the patent application WO2011/131642.

The "3-D Life Biomimetic Hydrogels" matrix, from the company Cellendes, is formed of dextran or polyvinyl alcohol (PVA) polymers functionalized by maleimide as an inert carrier, on which are grafted RGD motifs.

The hydrogel PuraMatrix®, from the company 3-D Matrix, is an absorbable hydrogel matrix composed of repetitive amino acid sequences arginine-alanine-alanine-aspartic acid, prepared in an aqueous solution. The matrix self-assembles into nanofibers on a similar scale to the extracellular matrix when monomers are exposed to physiological salt levels. The density of the nanofibers and average pore size (5-200 nm) can be controlled and adjusted according to the concentration of the peptide solution used. The support may be functionalized by the addition of biologically active peptide sequences.

As an example of polymer materials forming a porous inert matrix, mention may be made of Alvetex®, commercialised by Reinnervate. Alvetex® is a highly porous, inert polystyrene scaffold that provides cultured cells with an environment and physical space in which to grow in 3 dimensions. The architecture of Alvetex® is made of voids which are interconnected by pores creating a scaffold with >90% porosity. Once seeded onto Alvetex®, cells easily invade the scaffold and start to produce genuine, homogeneous 3D cellular structures that resemble micro-slabs of tissue. Alvetex® Scaffold is supplied as 200 μm thick discs is 384-well or 96-well plate on which the cells are seeded after rehydrating and washing the discs, and further addition of culture medium, if the cells are not added directly in their culture medium.

A 3D culture of eukaryotic cells is typically prepared by preparing the 3D culture scaffold and seeding the eukaryotic cells on the 3D scaffold, or by preparing a 3D culture scaffold, seeding the eukaryotic cells on the 3D scaffold, and adding an overlay of 3D culture scaffold on the seeded cells.

Accordingly, in an embodiment, the eukaryotic cells in 3D culture are cultivated in and/or on a three-dimensional biocompatible polymeric matrix. In an embodiment, said three-dimensional biocompatible polymeric matrix is a hydrogel. In another embodiment, said three-dimensional biocompatible polymeric matrix forms a porous inert matrix.

According to some embodiments, the eukaryotic cells in 3D culture are cultivated in and/or on a three-dimensional hydrogel comprising Matrigel®, collagen (in particular type I collagen), QGel® matrix, 3-D Life Biomimetic Hydrogel matrix, or PuraMatrix®.

In some embodiments, the three-dimensional biocompatible polymeric matrix, e.g. hydrogel, intrinsically contains growth factors. In some embodiments, the three-dimensional biocompatible polymeric matrix, e.g. hydrogel, is complemented with growth factors.

As mentioned above, the eukaryotic cells can also be in a 3D scaffold if present in a biological sample, such as a solid biological sample, for instance a tissue or solid tumour biopsy. In this embodiment the 3D scaffold thus comprises or consists of a native hydrogel, namely extracellular matrix.

Non limitative examples of solid biological sample include breast, prostate, brain, kidney, liver, pancreas, adrenal gland, colon, colorectal, ovary, testis, uterus, lung, lymphatic, and skin tissue or tumour samples.

Contacting the Eukaryotic Cells in 3D Scaffold with at Least One Formulation in Nanoemulsion Form The putting of the cells in 3D scaffold into contact with the formulation in nanoemulsion form, or plurality of formulations in nanoemulsion form, as described above has the purpose of allowing at least one nanoparticle of the formulation, hence the nucleic acid complexed thereto, to be integrated into the cells. It may be carried out by methods known to one skilled in the art. The contacting is performed under conditions sufficient to allow a nucleic acid which is contained in a formulation in nanoemulsion form to transfect the eukaryotic cells in 3D scaffold.

Thus, the cells are for example cultivated or present in and/or on a suitable 3D scaffold, and are then collectively transfected with the nanoparticles or library of nanoparticles contained in the formulation(s) in nanoemulsion form, for example in a 1/1 (1 nanoparticle/1cell) ratio. According to another example, each nanoparticle of the library is deposited on a support, for example in a well of a cultivation plate, and the cells are added onto said support.

The step of contacting the eukaryotic cells in 3D scaffold with at least one formulation in nanoemulsion form is typically carried out for 5 min to 8 days, for instance 5 min to 5 days, 15 min to 3 days. In particular, the step of contacting is typically carried out for at least 5 min, 10 min, 15 min, 30 min, 1 hour, 2 h, 3 h, 5 h, 10 h, 24 h, 36 h, 48 h, or more, and/or at most for 10 days, 7 days, 3 days, 24 h, 12 h, 6 h, 3 h, 1 h or 30 min.

The step a) for putting the cells in contact with the nanoparticles or library of nanoparticles contained in the formulation(s) in nanoemulsion form is for example carried out at a temperature in the range 20-40° C., for instance 20-25° C. or 35-40° C. In particular the temperature is of at least 20, 21, 22, 23, 24, 25, 26, 27, 28, 29, 30, 31, 32, 33, 34, 35, 36, 37, 38, 39, or 40° C., and/or of at most 40, 39, 38, 37, 36, 35, 34, 33, 32, 31, 30, 29, 28, 27, 26, 25, 24, 23, 22, 21, or 20° C.

In an embodiment the eukaryotic cells are contacted with the nanoparticles or library of nanoparticles contained in the formulation(s) in nanoemulsion form for a given period of time, for instance 12 h or 24 h, and the 3D scaffold is then washed, for instance with PBS, before fresh culture medium deprived of formulation(s) in nanoemulsion form is added. Alternatively, the formulation(s) in nanoemulsion form can be simply removed and replaced with fresh culture medium (deprived of formulation(s) in nanoemulsion form). In some cases, depending on the concentration of nanoparticles used for transfection, a washing step is carried out after the step of contacting in order to avoid possible toxic effects.

As shown on the following examples, efficient nucleic acid transfection was achieved using formulations in nanoemulsion form with a N/P ratio (where N=positive charge brought by the ammonium group of the nitrogen of the cationic lipids making up the crown of the lipid particle; P=negative charge brought by the phosphate group of the nucleic acids) of 80:1 for a nucleic acid concentration of 100 nM, or formulations in nanoemulsion form with a N/P ratio of 400:1 for a nucleic acid concentration of 20 nM. Accordingly, the value of N/P ratio of the nanoparticles in the premix formulation can be adapted depending on the concentration of nucleic acids to be complexed thereto, in order to modulate the amount of lipid nanoparticle-nucleic acid complexes placed in contact with the cells. The skilled person readily knows how to adjust the amount of formulations in nanoemulsion form placed in contact with the cells in order to optimize the transfection efficacy.

Screening

In the method wherein only one type of formulation in nanoemulsion form is used, the eukaryotic cells in 3D scaffold are selected according to presentation of a phenotype of interest, and optionally according to the integration or non integration of the tracer, if formulation in nanoemulsion form comprised a tracer.

In the method wherein a plurality of formulations in nanoemulsion form is used, the cells are selected according to the two following criteria: (i) integration of the tracer as described above and (ii) presentation of a phenotype of interest.

Identification of the cells having integrated the tracer may be carried out by means of methods known to one skilled in the art.

In an embodiment, when said tracer is a fluorophore or radioactive tracer, the selection of the cells having integrated said tracer is carried out by imaging (fluorescence imaging or nuclear imaging).

In another embodiment, the 3D scaffold, in particular if a native or synthetic hydrogel, is disrupted to recover the eukaryotic cells that were contacted with the formulation(s) in nanoemulsion form. When said tracer is a magnetic tracer, the selection of the cells having integrated said magnetic tracer is carried out by magnetic cell sorting (MACS® for "Magnetic Activated Cell Sorting"). When said tracer is a fluorophore, the selection of the cells having integrated said fluorophore is carried out by flow cytometry.

The identification of the cells having a phenotype of interest may be carried out by means of methods known to one skilled in the art. Preferably, identification of the cells having a phenotype of interest is carried out by imaging or flow cytometry.

In an embodiment, the identification of the cells having integrated the tracer is carried out before identifying the cells having a phenotype of interest. In another embodiment, the identification of the cells having integrated the tracer and the identification of the cells having a phenotype of interest are carried out simultaneously.

Non-limiting examples of a phenotype of interest are notably apoptosis, cell proliferation, differentiation, the expression of a cancer maker, such as for example the expression of the prostate specific antigen (PSA), resistance or sensitivity to a therapeutic agent, for example a chemotherapy agent, the resistance or sensitivity to an infectious agent, preferably to a virus, the resistance or sensitivity to an environmental stress, such as for example resistance or sensitivity to drought or to an insect.

The phenotypes of interest may be studied without any preliminary marking or with marking with a fluorescent reporter gene or else further after marking with a fluorescent antibody. Identification of the proliferation of the cells may notably be achieved by marking with propidium iodide, EdU, or Hoechst 33342. Identification of apoptosis of the cells may notably be achieved by Annexine V-FITC marking or by so called TUNEL ("Terminal deoxynucleotidyl transferase dUTP Nick End Labelling") marking or by analysis of activation of caspases.

In the method of screening of the invention, the candidate nucleic acid is identified as a sequence of interest if a phenotype of interest has been detected, or identified as a sequence of no interest if no phenotype of interest was detected.

Identification of the Nucleotide Sequence of the Candidate Nucleic Acid of Interest In the method of screening according to the invention, the identification of the candidate nucleotide sequence of the nucleic acid in step b) is achieved by identifying the single DNA tag sequence. Indeed, as each candidate nucleic acid is associated with a single DNA tag, by identifying said single DNA tag, it is possible to determine which candidate nucleic acid was transfected into the cells.

Identification of the DNA tag is achieved after (i) extraction of the DNA from the selected cells, (ii) amplifying the DNA extracted in step (i) with complementary universal primers of the first and second sequences with at least 20 nucleotides of said single DNA tags, as defined above, and sequencing of the amplified DNA, or (iib) sequencing of the DNA extracted in step (i).

The DNA extraction step (i) may be achieved with methods known to one skilled in the art.

In step (ii), the amplification may be achieved by using polymerase chain reaction conventional techniques (PCR).

In certain embodiments, the amplification in step (ii) comprises an initial denaturation step followed by denaturation-hybridization-elongation cycles and by a final extension step.

The initial denaturation step may be achieved under temperature conditions ranging from 90° C. to 105° C., for 15 s to 15 min, preferably from 92° C. to 102° C., still preferably from 95° C. to 100° C. Preferably, the initial denaturation step is carried out for 1 min to 15 min, still preferably for 2 min to 12 min, still preferably for 5 min to 10 min.

Each denaturation-hybridization-elongation cycle includes a denaturation phase under heating conditions, followed by a phase for hybridization of the primers, produced under conditions allowing hybridization of the primers with the single DNA tag to be amplified, and an elongation phase produced under conditions allowing the polymerase to synthesize an extension product from each primer having been hybridized with the DNA tag to be amplified.

The denaturation phase may be achieved between 90° C. and 105° C., preferably between 92° C. and 100° C., still preferably between 94° C. and 98° C., for 10 s to 4 min, preferably for 10 s to 2 min, still preferably for 15 s to 1 min.

The hybridization phase, i.e., the hybridization phase of the primers, may be achieved between 35° C. and 70° C., preferably between 40° C. and 65° C., still preferably between 45° C. and 60° C., for 10 s to 2 min, preferably for 20 s to 1.5 min, still preferably for 25 s to 45 s.

The elongation phase may be achieved between 40° C. and 80° C., preferably between 50° C. and 75° C., still preferably between 60° C. and 72° C., for 10 s to 5 min, preferably for 20 s to 3 min, still preferably for 25 s to 1 min.

The denaturation-hybridization-elongation steps may be repeated for 30 to 60 cycles, preferably for 35 to 45 cycles.

The final extension step may be achieved between 40° C. and 80° C., preferably between 50° C. and 75° C., still preferably between 60° C. and 72° C., for 1 min to 10 min, preferably for 3 min to 8 min, still preferably for 4 min to 6 min.

The sequencing in steps (ii) and (iib) may be carried out by using conventional sequencing techniques.

Preferably, the sequencing step (iib) is carried out on third generation sequencers which allow sequencing of a single DNA molecule, e.g. by using the Pacific Bioscience® method, the ion Torrent® method, the Oxford Nanopore® method, the so called "optipore" method (Noblegen BioSciences). The sequencing in steps (ii) and (iib) therefore allows identification of the single sequence of at least 10 nucleotides of each DNA tag.

Individual Screening of Candidate Nucleic Acids of Interest

In the screening methods according to the invention, it is possible that the cells integrate several nanoparticles, this leading to the identification of several candidate nucleic acids as being responsible for the phenotype of interest. Thus, in order to make sure that all the identified candidate nucleic acids are really responsible for the phenotype of interest, the screening methods according to the invention may therefore, further comprise an individual screening step of the identified candidate nucleic acid.

This individual screening step is carried out by achieving a second cycle of steps a) to c), it being understood that the contacting of the cells in step a) is achieved with a nanoparticle comprising a tracer, a fluorophore and the candidate nucleic acid identified.

The following examples are given to enable those skilled in the art to more clearly understand and practice the present invention. They should not be considered as limiting the scope of the invention, but merely as being illustrative and representative thereof.

EXAMPLES

Example 1: Design and Preparation of Fluorescent Nanoparticles Containing a siRNA or miRNA 1.1 Preparation and Composition of «Premix» Formulations Before Complexing with siRNA The aqueous phase used was a PBS 1× buffer solution.
The suppliers of the compounds were the following:
Lipoid S75-3: Lipoid
Lipoid S75: Lipoid
Lipoid S100-3: Lipoid
DOTAP: Avanti Polar
DOPE: Avanti Polar
MyrjS40: Croda
Suppocire NB: Gattefossé
Soybean oil: Croda The hydrodynamic diameter of the droplets in the formulations and their zeta potential were measured by dynamic light scattering using ZetaSizer apparatus, Malvern. The hydrodynamic diameter of the droplets was measured in 0.1× solution of PBS, the zeta potential in 0.15 mM aqueous solution of NaCl.

Sixteen different formulations were prepared, the compositions of which are given in Tables 1 to 5.

TABLE 1

|  |  | A1 (comp.) | A2 | A3 |
|---|---|---|---|---|
| RING | Amphiphilic lipid: Lipoid | S75-3 | S75-3 | S75-3 |
|  | wt. % Lipoid/droplet | 35.29 | 8.83 | 3.53 |
|  | wt. % Lipoid/ring without PEG | 100 | 25 | 10 |
|  | wt. % Lipoid/crown | 46.15 | 11.54 | 4.62 |
|  | mol. % Lipoid/crown | 70.02 | 16.86 | 6.74 |
|  | Cationic surfactant DOTAP | X | DOTAP | DOTAP |
|  | wt. % DOTAP/droplet | 0 | 26.47 | 26.47 |
|  | wt. % DOTAP/crown without PEG | 0 | 75 | 75 |
|  | wt. % DOTAP/crown | 0 | 34.61 | 34.61 |
|  | mol. % DOTAP/crown | 0 | 54.28 | 54.24 |
|  | Co-surfactant | Myrj S40 | Myrj S40 | Myrj S40 |

TABLE 1-continued

|  |  | A1 (comp.) | A2 | A3 |
|---|---|---|---|---|
|  | wt. % co-surfactant/droplet | 41.17 | 41.17 | 41.17 |
|  | wt. % (co-surfactant)/crown | 53.85 | 53.85 | 53.85 |
|  | mol. % (co-surfactant)/crown | 29.98 | 28.86 | 28.84 |
|  | Helper lipid DOPE | X | X | DOPE |
|  | wt. % DOPE/droplet | 0 | 0 | 5.29 |
|  | wt. % DOPE/crown without PEG | 0 | 0 | 15 |
|  | wt. % DOPE/crown | 0 | 0 | 6.92 |
|  | mol. % DOPE/crown | 0 | 0 | 10.18 |
| CORE | Solubilising lipid | Suppocire NB | Suppocire NB | Suppocire NB |
|  | wt. % solubilising lipid/core | 75 | 75 | 75 |
|  | wt. % solubilising lipid/droplet | 17.65 | 17.65 | 17.65 |
|  | Oil | Soybean oil | Soybean oil | Soybean oil |
|  | wt. % oil/core | 25 | 25 | 25 |
|  | wt. % oil/droplet | 5.88 | 5.88 | 5.88 |
|  | wt. % core/droplet |  | 23.53 | 23.53 |
|  | mol. % core/droplet |  | 33.35 | 33.35 |
|  | Formulation (number of repeats) | 3 | 4 | 3 |
| RESULT | Hydrodynamic diameter (nm) - average | 124.9 | 49.1 | 44.48 |
|  | ZP (mV)_in 0.15 mM NaCl | −26 | 25.38 | 30.87 |
|  | Stability | ok | ok | ok |
|  | Complexing (%) | 0 | 100 | 100 |
|  | Silencing efficacy (%) | 0 | 72.88 | 75.06 |

TABLE 2

|  |  | B1 (comp.) | B2 | B3 |
|---|---|---|---|---|
| CORE | Amphiphilic lipid: Lipoid | S75-3 | S75 | S100-3 |
|  | wt. % Lipoid/droplet | 8.75 | 4.25 | 4.25 |
|  | wt. % Lipoid/crown without PEG | 100 | 50 | 50 |
|  | wt. % Lipoid/crown | 15.98 | 7.99 | 7.99 |
|  | mol. % Lipoid/crown | 34.14 | 17.89 | 17.89 |
|  | Cationic surfactant DOTAP | X | DOTAP | DOTAP |
|  | wt. % DOTAP/droplet | 0 | 4.25 | 4.25 |
|  | wt. % DOTAP/crown without PEG | 0 | 50 | 50 |
|  | wt. % DOTAP/crown | 0 | 7.99 | 7.99 |
|  | mol. % DOTAP/crown | 0 | 17.85 | 17.85 |
|  | Co-surfactant | Myrj S40 | Myrj S40 | Myrj S40 |
|  | wt. % co-surfactant/droplet | 46 | 46 | 46 |
|  | wt. %(co-surfactant)/crown | 84.02 | 84.02 | 84.02 |
|  | mol. % (co-surfactant)/crown | 65.86 | 64.27 | 64.27 |
|  | Helper lipid DOPE | X | X | X |
|  | wt. % DOPE/droplet | 0 | 0 | 0 |
|  | wt. % DOPE/crown without PEG | 0 | 0 | 0 |
|  | wt. % DOPE/crown | 0 | 0 | 0 |
|  | mol. % DOPE/crown | 0 | 0 | 0 |
| CORE | Solubilising lipid | Suppocire NB | Suppocire NB | Suppocire NB |
|  | wt. % solubilising lipid/core | 75 | 75 | 75 |
|  | wt. % solubilising lipid/droplet | 33.94 | 33.94 | 33.94 |
|  | Oil | Soybean oil | Soybean oil | Soybean oil |
|  | wt. % oil/core | 25 | 25 | 25 |
|  | wt. % oil/droplet | 11.31 | 11.31 | 11.31 |
|  | wt. % core/droplet |  | 45.25 | 45.25 |
|  | mol. % core/droplet |  |  |  |
|  | Formulation (number of repeats) | 6 | 2 | 2 |

TABLE 2-continued

|  |  | B1 (comp.) | B2 | B3 |
|---|---|---|---|---|
| RESULT | Hydrodynamic diameter (nm) - average | 59.51 | 42.11 | 6..43 |
|  | ZP (mV) in 0.15 mM NaCl | −21.8 | 21.4 | 6.72 |
|  | Stability | ok | ok | ok |
|  | Complexing (%) | 0 | ND | ND |
|  | Silencing efficacy (%) | 0 | 0 | 0 |

TABLE 3

|  |  | B4 (comp.) | B5 | B6 |
|---|---|---|---|---|
| RING | Amphiphilic lipid: Lipoid | S75-3 | S75-3 | S75-3 |
|  | wt. % Lipoid/droplet | 6.58 | 2.19 | 2.84 |
|  | wt. % Lipoid/crown without PEG | 100 | 25 | 25 |
|  | wt. % Lipoid/crown | 14.29 | 4 | 6.9 |
|  | mol. % Lipoid/crown | 31.24 | 8.39 | 12.39 |
|  | Cationic surfactant DOTAP | X | DOTAP | DOTAP |
|  | wt. % DOTAP/droplet | 0 | 6.56 | 8.52 |
|  | wt. % DOTAP/crown without PEG | 0 | 75 | 75 |
|  | wt. % DOTAP/crown | 0 | 11.99 | 20.67 |
|  | mol. % DOTAP/crown | 0 | 26.99 | 39.87 |
|  | Co-surfactant | Myrj S40 | Myrj S40 | Myrj S40 |
|  | wt. % co-surfactant/droplet | 39.48 | 46 | 29.87 |
|  | wt. % (co-surfactant)/crown | 85.71 | 84.02 | 72.43 |
|  | mol. % (co-surfactant)/crown | 68.76 | 64.63 | 47.74 |
|  | Helper lipid DOPE | X | X | X |
|  | wt. % DOPE/droplet | 0 | 0 | 0 |
|  | wt. % DOPE/crown without PEG | 0 | 0 | 0 |
|  | wt. % DOPE/crown | 0 | 0 | 0 |
|  | mol. % DOPE/crown | 0 | 0 | 0 |
| CORE | Solubilising lipid | Suppocire NB | Suppocire NB | Suppocire NB |
|  | wt. % solubilising lipid/core | 75 | 75 | 75 |
|  | wt. % solubilising lipid/droplet | 40.46 | 33.94 | 44.07 |
|  | Oil | Soybean oil | Soybean oil | Soybean oil |
|  | wt. % oil/core | 25 | 25 | 25 |
|  | wt. % oil/droplet | 13.49 | 11.31 | 14.69 |
|  | wt. % core/droplet |  | 45.25 | 58.76 |
|  | mol. % core/droplet |  |  | 73.99 |
|  | Formulation (number of repeats)) | 3 | 4 | 6 |
| RESULT | Hydrodynamic diameter (nm) - average | 84.88 | 56.68 | 86.77 |
|  | ZP (mV) in 0.15 mM NaCl | −18.89 | 26.51 | 36.38 |
|  | Stability | ok | ok | ok |
|  | Complexing (%) | 0 | 100 | 100 |
|  | Silencing efficacy (%) | 0 | 0 | 42.81 |

TABLE 4

|  |  | B9 (Comp.) | B10 |
|---|---|---|---|
| RING | Amphiphilic lipid: Lipoid | S75-3 | S75-3 |
|  | wt. % Lipoid/droplet | 0 | 1.71 |
|  | wt. % Lipoid/crown without PEG | 0 | 15 |
|  | wt. % Lipoid/crown | 0 | 4.14 |
|  | mol. % Lipoid/crown | 0 | 7.43 |
|  | Cationic surfactant DOTAP | DOTAP | DOTAP |
|  | wt % DOTAP/droplet | 8.25 | 8.25 |
|  | wt. % DOTAP/crown without PEG | 75 | 75 |
|  | wt. % DOTAP/crown | 20.67 | 20.67 |
|  | mol. % DOTAP/crown | 39.87 | 39.87 |
|  | Co-surfactant | Myrj S40 | Myrj S40 |
|  | wt. % co-surfactant/droplet | 29.87 | 29.87 |
|  | wt. % (co-surfactant)/crown | 72,.43 | 72.43 |
|  | mol. % (co-surfactant/crown | 47.74 | 47.74 |
|  | Helper lipid DOPE | DOPE | DOPE |
|  | wt. % DOPE/droplet | 2.84 | 1.71 |
|  | wt. % DOPE/crown without PEG | 25 | 10 |
|  | wt. % DOPE/crown | 6.9 | 2.76 |
|  | mol. % DOPE/crown | 10.18 | 4.99 |
| CORE | Solubilising lipid | Suppocire NB | Suppocire NB |
|  | wt. % solubilising lipid/core | 75 | 75 |
|  | wt. % solubilising lipid/droplet | 44.07 | 44.07 |
|  | Oil | Soybean oil | Soybean oil |
|  | wt. % oil/core | 25 | 25 |
|  | wt. % oil/droplet | 14.69 | 14.69 |
|  | wt. % core/droplet |  | 58.76 |
|  | mol. % core/droplet |  | 73.74 |
|  | Formulation (number of repeats) | 1 poor formulation | 5 |
| RESULT | Hydrodynamic diameter (nm) - average | ND | 88.64 |
|  | ZP (mV) in 0.15 mM NaCl | ND | 36.9 |
|  | Stability | ND | Ok |
|  | Complexing (%) | ND | 100 |
|  | Silencing efficacy (%) | ND | 49.34 |

TABLE 5

|  |  | C1 (comp.) | C2 | C3 |
|---|---|---|---|---|
| RING | Amphiphilic lipid: Lipoid | S75-3 | S75-3 | S75-3 |
|  | wt. % Lipoid/droplet | 28.44 | 7.11 | 4.27 |
|  | wt. % Lipoid/crown without PEG | 100 | 25 | 15 |
|  | wt. % Lipoid/crown | 70.24 | 17.56 | 10.54 |
|  | mol. % mol. Lipoid/crown | 86.55 | 20.65 | 12.38 |
|  | Cationic surfactant DOTAP | X | DOTAP | DOTAP |
|  | wt. % DOTAP/droplet | 0 | 21.33 | 21.33 |
|  | wt. % DOTAP/crown without PEG | 0 | 75 | 75 |
|  | wt. % DOTAP/crown | 0 | 52.68 | 52.68 |
|  | mol. % DOTAP/crown | 0 | 66.51 | 66.47 |
|  | Co-surfactant | Myrj S40 | Myrj S40 | Myrj S40 |
|  | wt. % co-surfactant/droplet | 12.05 | 12.05 | 12.05 |
|  | wt. % (co-surfactant/crown | 29.76 | 29.76 | 29.76 |
|  | mol. % (co-surfactant/crown | 13.45 | 12.84 | 12.83 |
|  | Helper lipid DOPE | X | X | DOPE |
|  | wt. % DOPE/droplet | 0 | 0 | 2.84 |
|  | wt. % DOPE/crown without PEG | 0 | 0 | 10 |
|  | wt. % DOPE/crown | 0 | 0 | 7.02 |
|  | mol. % DOPE/crown | 0 | 0 | 8.32 |
| CORE | Solubilising lipid | Suppocire NB | Suppocire NB | Suppocire NB |
|  | wt. % solubilising lipid/core | 75 | 75 | 75 |
|  | wt. % solubilising lipid/droplet | 44.63 | 44.63 | 44.63 |
|  | Oil | Soybean oil | Soybean oil | Soybean oil |
|  | wt. % oil/core | 25 | 25 | 25 |
|  | wt. % oil/droplet | 14.88 | 14.88 | 14.88 |
|  | wt. % core/droplet |  | 59.51 | 59.51 |
|  | mol. % core/droplet |  | 65.85 |  |
|  | Formulation (number of repeats) | 4 | 4 | 3 |
| RESULT | Hydrodynamic diameter (nm) - average | 153.03 | 162.2 | 168.9 |

TABLE 5-continued

|  | C1 (comp.) | C2 | C3 |
|---|---|---|---|
| ZP (mV)_in 0.15 mM NaCl | −37.71 | 53.7 | 51.83 |
| Stability | ok | ok | ok |
| Complexing (%) | 0 | 100 | 100 |
| Silencing efficacy (%) | 0 | 80.51 | 81.72 |

In Tables 1 to 5: wt % corresponds to weight percent; mol. % corresponds to mole percent. ND (non-determined) means that the experiment was not performed. The percentages «/droplet» represent percentages relative to the whole (Lipoid/DOTAP/Myrj S40/optional DOPE/Suppocire NB/Soybean oil). The percentages «/ring» represent percentages relative to the whole (Lipoid/DOTAP/Myrj S40/optional DOPE). The percentages «/ring without PEG» represent percentages relative to the whole (Lipoid/DOTAP/optional DOPE). The percentages «/core represent percentages relative to the whole (Suppocire NB/Soybean oil). Lipoid S75-3 comprises 65-75% of phosphatidylcholine. The aliphatic chains of the phospholipids are mostly saturated (mean composition: 12-16% of C16:0, 80-85% of C18:0, <5% of C18:1, <2% of C18:2). Lipoid S75 comprises 65-75% of phosphatidylcholine. The aliphatic chains of the phospholipids are mostly unsaturated (mean composition: 17-20% of C16:0, 2-5% of C18:0, 8-12% of C18:1, 58-65% of C18:2, 4-6% of C18:3). Lipoid S100-3 comprises >94% of phosphatidylcholine, i.e. The aliphatic chains of the phospholipids are mostly saturated (mean composition: 12-16% of C16:0, 85-88% of C18:0, <2% of C18:1, <1% of C18:2).

The formulations A1, B1, B4 and C1 are comparative examples, since they do not comprise any cationic surfactant.

Their zeta potentials are negative.

The complexing of siRNA did not occur on the surface of the droplets as was expected.

Formulation B9 is a comparative example since it does not comprise an amphiphilic lipid. It was not possible to prepare the emulsion.

The preparation method given below was followed:

(vi) Preparation of the Oil Phase:

The soybean oil, suppocire NC, amphiphilic lipid, DOTAP, optional DOPE were weighed and mixed with dichloromethane before being heated to 60° C. to obtain a homogeneous viscous solution. The dichloromethane promotes solubilisation. The solvents were then evaporated in vacuo.

(vii) Preparation of the Aqueous Phase:

During the ethanol evaporation phase the aqueous phase was prepared. In a 5 ml Eppendorf tube, the co-surfactant, glycerol, and aqueous solution of PBS (154 mM NaCl, pH 7.4) were mixed then dissolved in a bath at 75° C.

(viii) Mixing of the Two Phases:

The oil phase was at about 40° C. (in viscous form) and the aqueous phase at about 70° C. (on leaving the bath). The aqueous bath was poured into the oil phase.

(ix) Emulsification:

The bottle containing the two phases was fitted inside the sonication chamber of an AV505® sonicator (Sonics, Newton, USA). The protocol entailed sonication cycles (10 seconds of activity every 30 seconds) at a power of 100 W over a period of 40 minutes.

(x) Purification:

The droplets produced were then purified by dialysis (cut-off threshold: 12 kDa, against 154 mM NaCl overnight) to remove the lipid components non-integrated in the LNPs. Finally the formulation was sterilised by filtration on a cellulose membrane.

Size of the Droplets of the Formulation and Zeta Potential Influence of the Composition of the Formulation The results in Tables 1 to 5 show that a decrease in the proportion of co-surfactant (Myrj S40) leads to an increase in the diameter of the droplets.

Trend in Time

The trend in droplet size (Table 6) and zeta potential (Table 7) of the formulations were measured at 40° C. (accelerated stability). The formulations were stored at 40° C. between two measurements.

TABLE 6

Trend in droplet size and polydispersity index (PDI) measured by dynamic light scattering as a function of time

| Days | B1 | B4 | B5 | B6 | B10 | C1 | C2 |
|---|---|---|---|---|---|---|---|
| 0 | 58.27 | 98.87 | 60.03 | 87.93 | 91.53 | 157.43 | 171.4 |
| 7 | 60.52 | 97.12 | 58.96 | 87.1 | 90.51 | 156.17 | 172.63 |
| 14 | 62.59 | 98.36 | 58.28 | 86.25 | 89.87 | 156.46 | 170.15 |
| 21 | 59.41 | 97.81 | 59.23 | 85.78 | 90.3 | 153.03 | 162.2 |
| 28 | 61 | 97.15 | 60.36 | 87.61 | 90.96 | 153.9 | 161.47 |

TABLE 7

Trend in zeta potential of the formulations as a function of time

| Days | B1 | B4 | B5 | B6 | B10 | C1 | C2 |
|---|---|---|---|---|---|---|---|
| 0 | −21.3 | −21.16 | 24.03 | 34.13 | 34.97 | −40.27 | 57.33 |
| 7 | −25.6 | −21.17 | 28.23 | 31.77 | 34.73 | −43.13 | 56.77 |
| 14 | −24.73 | −21.03 | 29.45 | 28.4 | 33.47 | −42.33 | 55.33 |
| 21 | −21.8 | −20.47 | 28.63 | 34.3 | 33.07 | −38.1 | 53.9 |
| 28 | −18.93 | −19.83 | 27.5 | 33 | 31.23 | −39.03 | 51.6 |

It was observed that the size of the droplets and the zeta potential of the formulations according to the invention when stored at 40° C. for 300 days showed no change.

These results demonstrate that the formulations of the invention are stable over time.

1.2. Complexing with siRNA: Preparation of «Final» Formulations Comprising siRNA Nucleotide Sequences.

The general procedure below was followed:

Complexing involved simple mixing of the formulations prepared above and of a siRNA solution in a buffer. The choice of buffer related to the envisaged application: for an in vitro study, the optimised culture medium for the transfection steps was OptiMEM. For a complexing study the buffer used was 5 mM Hepes.

The amount of siRNA used was 0.5 μg (GFP-22 siRNA rhodamine (catalogue no 1022176) (Qiagen) or siGFP (Sigma)) (25 μg/mL in 20 μL).

The mixture was left under agitation for 30 minutes at 600 rpm, at ambient temperature (about 25° C.).

Complexing was Visualised by Means of Two Instruments:

Agarose gel electrophoresis which allowed observation of siRNA migration. If there is good complexing then the droplets comprising the complexed siRNA will be heavier than the free siRNA and will be seen in the wells. If complexing is less extensive, free siRNA migrate towards another position.

With DLS the impact of complexing on hydrodynamic diameter was observed. The more complexing is efficient the more the profile tends towards monomodal distribution.

The amount of formulation needed to obtain a quantitative complexing yield of siRNA was optimised.

In practice the negative charges provided by the siRNA are offset by the positive charges of the formulation (i.e. the positive charges of the cationic surfactant DOTAP).

Figure 2:
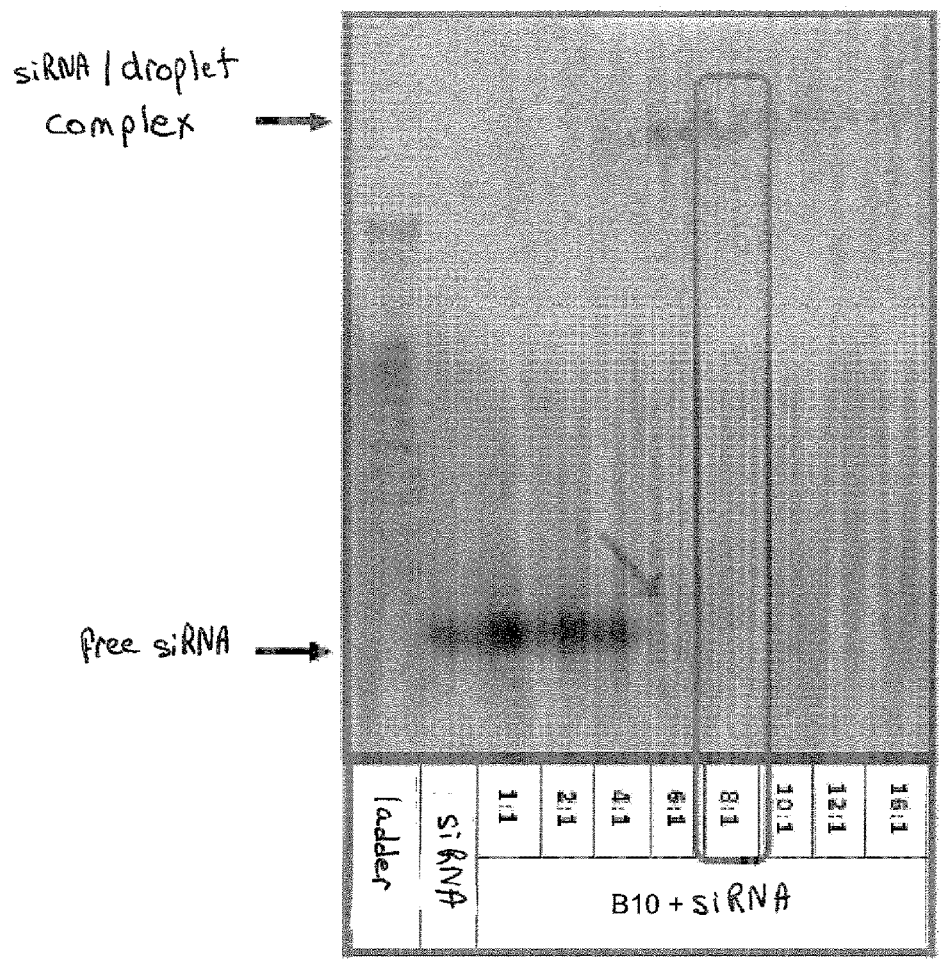
FIG. 2 shows an electrophoresis with UV detection after complexing of siRNA with the formulation B10 and the concentrations specified in Table 8. The scale and siRNA (reference) are given on the left.
Figure 3:
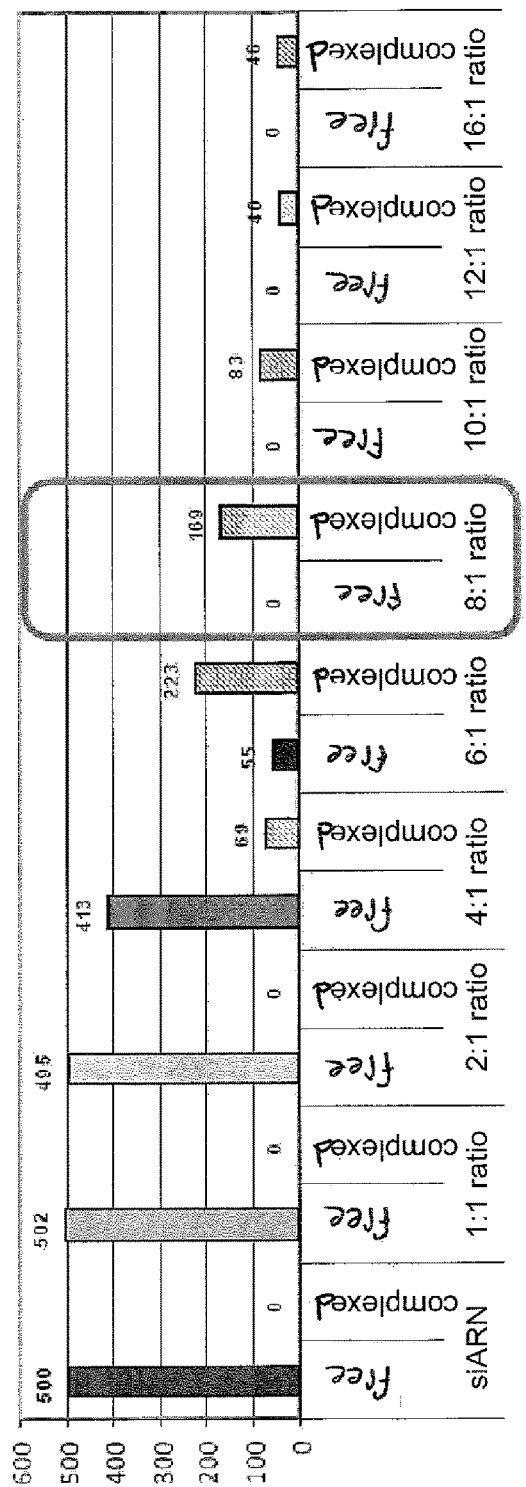
FIG. 3 gives the results of the amount of siRNA (ng) obtained when processing electrophoresis data with ImageJ software for the electrophoresis gel with UV detection in FIG. 2.

Typically, when the only cationic surfactant of the formulation is DOTAP (which only comprises a single positive charge) a quantitative complexing yield is obtained when the ratio of amount of positive charges due to the cationic surfactant in the «premix» formulation to the amount of negative charge provided by the siRNA is greater than 8:1 as illustrated in FIGS. 2 and 3.

FIG. 2 shows an electrophoresis gel with UV detection after complexing of siRNA with formulation B10 at the concentrations specified in Table 8 by mixing a solution of siRNA and the formulation in 5 mM Hepes buffer. Before depositing on 1.5% agarose gel, 2 µL of loading buffer were added to the tests. After 1 h30 electrophoresis at 100 V, the gel was immersed in GelRed 3×. Finally UV detection was carried out.

TABLE 8

| ratio between amount of positive charges due to the catatonic surfactant in the <<premix>> formulation and amount of negative charges provided by siRNA | 1:1 | 2:1 | 4:1 | 6:1 | 8:1 | 10:1 | 12:1 | 16:1 |
|---|---|---|---|---|---|---|---|---|
| Concentration of siARN (µg/mL) | | | | | 25 | | | |
| Concentration of DOTAP (µg/mL) | 0 | 25 | 50 | 100 | 150 | 200 | 250 | 300 | 400 |

FIG. 3 gives the results obtained by processing electrophoresis data on same experiments using ImageJ software.

FIGS. 2 and 3 show that when the ratio between the amount of positive charges due to the cationic surfactant in the «premix» formulation and the amount of negative charges provided by siRNA is greater than 8:1 there no longer remains any free siRNA in the medium and that the siRNA has been fully complexed.

Figure 4:
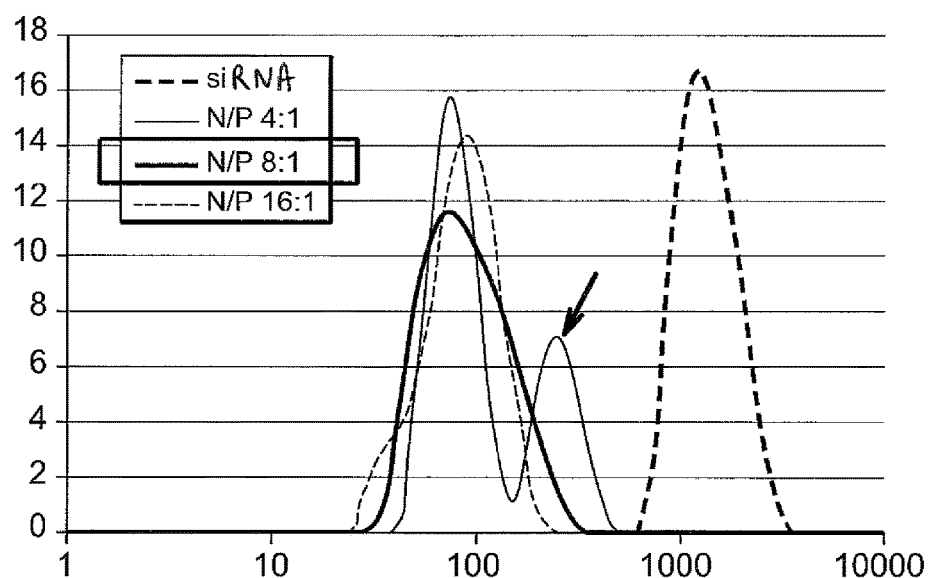
FIG. 4 gives the intensity obtained on ZetaSizer Malvern apparatus as a function of hydrodynamic diameter in nm for free siRNA (comparison) and for three formulations of the invention obtained by complexing with a ratio N/P: between the amount of positive charges due to the cationic surfactant in the «premix» formulation (due to charged nitrogen hence the N in N/P), and the amount of negative charges provided by the siRNAs (due to the phosphorus of siRNA hence the P in N/P) of 4:1, 8:1 or 16:1.

FIG. 4 shows the intensity obtained on Malvern ZetaSizer apparatus as a function of hydrodynamic diameter in nm for free siRNA (comparison) and for three formulations of the invention obtained by complexing with ratio values between amount of positive charges due to the cationic surfactant in the «premix» formulation and the amount of negative charges provided by siRNA of 4:1, 8:1 and 16:1.

The diameter was greater for free siRNA (comparison).

When the ratio between amount of positive charges due to the cationic surfactant in the «premix» formulation and amount of negative charges provided by siRNA is 4:1, two populations were observed: a siRNA/droplet complex of about 100 nm and a population of greater size representing siRNA in free form (arrow).

When the ratios of amount of positive charges due to the cationic surfactant in the «premix» formulation and amount of negative charges provided by the siRNA are 8:1 and 16:1, a single population representing the siRNA/droplet complex was observed.

These results also show that quantitative complexing (100%) of siRNA on the droplets is possible.

The complexing step was performed with various formulations.

By way of comparison, a complexing test was performed with a formulation free of cationic surfactant: formulation B1 described above. As expected, the complexing of the siRNA did not take place and the siRNA remained in free form.

Figure 5:
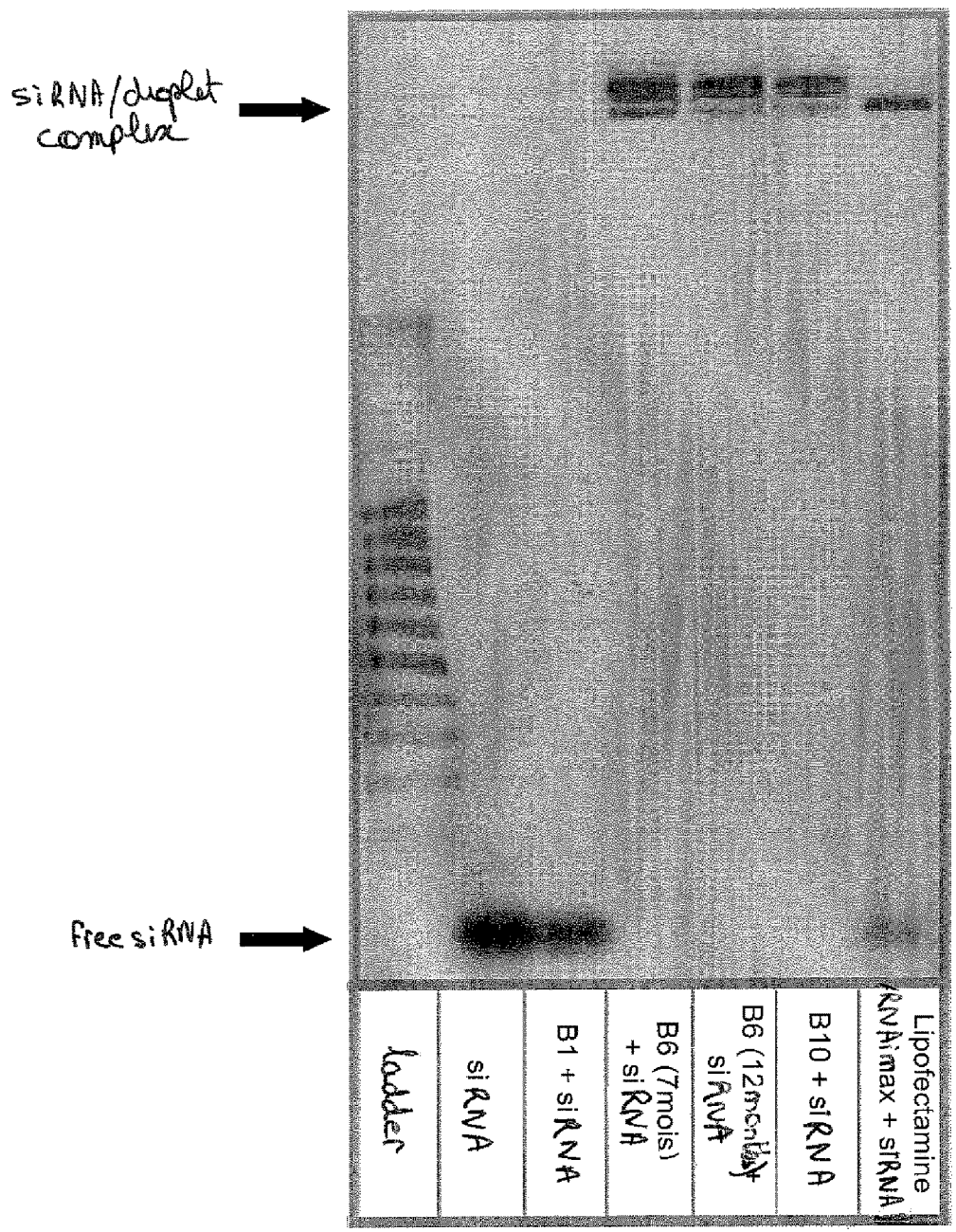
FIG. 5 shows an electrophoresis gel after UV detection with from left to right:
  the scale,
  free siRNA (reference)
  then the migrations obtained by siRNA complexing:
    with formulation B1 (comparative example) (no complexing, the siRNA are free);
    with formulation B6 with a ratio between the amount of positive charges due to the cationic surfactant in the «premix» formulation and the amount of negative charges provided by the siRNA of 8:1 (quantitative complexing).
    with formulation B6 and a ratio between amount positive charges due to the cationic surfactant in the «premix» formulation and amount of negative charges provided by the siRNA of 8:1 (quantitative complexing)

FIG. 5 shows an electrophoresis gel with UV detection giving from left to right:
the scale,
free siRNA (reference)
then the migrations obtained by siRNA complexing:
    with formulation B1 (comparative example) (no complexing, the siRNA are free);
    with formulation B6 (premix formulated 6 months previously) having a ratio between amount of positive charges due to the cationic surfactant in the «premix» formulation and amount of negative charges provided by the siRNA of 8:1 (quantitative complexing);
    with formulation B6 (premix formulated 12 months previously) with a ratio between amount of positive charges due to the cationic surfactant in the «premix» formulation and amount of negative charges provided by the siRNA of 8:1, the formulation having been stored 7 months at ambient temperature prior to complexing (quantitative complexing);
    with formulation B10 and a ratio between amount of positive charges due to the cationic surfactant in the «premix» formulation and amount of negative charges provided by the siRNA of 8:1 (quantitative complexing);
    with lipofectamine (comparative example) (incomplete complexing).

The complexing of siRNA was quantitative when formulation B6 or B10 was used. The storage of the formulation at ambient temperature before complexing with siRNA did not have any influence on the yield of complexing which remained quantitative, thereby showing the stability of the formulations used.

The yield was quantitative whether or not the formulation used contained DOPE.

With the commercial transfection agent Lipofectamine RNAimax, more than 60% of the siRNA were found in free form. This implies that the formulations of nanoemulsions used in the invention offer a better complexing yield than Lipofectamine.

Finally the release kinetics of siRNA in the siRNA/formulation B10 complex prepared above were studied to observe the trend in complexing over time and are illustrated in FIG. 6. Up to 3 hours after complexing the siRNA are not found in free form. At 6 hours the siRNA start to be released. The complex is therefore stable for at least three hours.

1.3. In Vitro Transfection

Transfection tests were conducted on different cell lines overexpressing Green Fluorescent Protein (GFP) by providing a siRNA specifically inhibiting a sequence of messenger RNA of this protein (GFP-22 siRNA rhodamine (catalog no 1022176) (Qiagen)).

Transfection was performed with a final siRNA concentration of 100 nM. Cells expressing GFP were seeded in 12-well plates (25 000 cells/well) and the wells were treated with the complexes siRNA/Formulations (B1, B6, B6 7 months after its preparation or B10) obtained above. The cells were then incubated 72 hours at 37° C., and recovered for analysis of fluorescence intensity by flow cytometry to determine the efficacy of the formulation as transfecting agent. The active delivery of siRNA specifically inhibiting the expression of the GFP protein causes a decrease in the fluorescence provided by this protein.

The commercial transfecting agent Lipofectamine RNAimax was used for comparison.

FIG. 7 shows the % decrease in fluorescence intensity when transfecting the cell lines with:

Lipofectamine RNAimax;
the siRNA/formulation B1 complex;
the siRNA/formulation B6 complex, the formulation having been stored 7 months at ambient temperature prior to complexing;
the siRNA/formulation B6 complex, the formulation having been stored 12 months at ambient temperature prior to complexing;
the siRNA/formulation B10 complex,
a complex siRNA/formulation of cationic liposomes comprising DOTAP (58 wt. %), DOPE (18 wt. %), cholesterol (2 wt. %) and DSPE-PEG3000 (22 wt. %)) (comparative).

A decrease in fluorescence of 33 to 50% is observed with the tested formulations of the invention. The formulations of the invention therefore allow active delivery of siRNA inducing relative silencing of the expression of the GFP gene.

In addition, by incorporating DOPE in the formulations, a greater decrease in fluorescence was observed, DOPE promoting endosomal escape.

No decrease in fluorescence was observed with the complex of siRNA./formulation of cationic liposomes which could be attributed for example to poor stability of the liposomes in the culture medium, poor complexing yield and/or poor retaining of siRNA by the liposomes after complexing.

Finally such results on the active delivery of siRNA mediated by the formulations of the invention were reproduced on 3 cell lines expressing GFP: U2OS, PC3 and Hela, as illustrated in FIG. 8.

1.4. Complexing with Synthetic microRNA: Preparation of «Final» Formulations Comprising Nucleotide Sequences of Synthetic microRNA (Mimic).

The general procedure given below was followed:

Complexing involved simple mixing of the A3 premix formulation prepared above with a solution of microRNA (miRIDIAN Mimic Human has-miR612 (ThermoScientific REF#C-300937-01 Batch no 130611)), in a buffer. The choice of buffer was dependent on the envisaged application: for an in vitro study the optimised culture for transfection steps OptiMEM®, was used. For a study on complexing 5 mM Hepes buffer was used.

An amount of 0.5 µg of microRNA was used (miRIDIAN Mimic Human has-miR612 (ThermoScientific REF#C-300937-01 Batch no 130611).

The mixture was left under agitation 30 minutes at 600 rpm, at ambient temperature (about 25° C.).

Complexing was visualised by detection on agarose gel obtained by electrophoresis which allowed observation of microRNA migration. With good complexing the droplets comprising the complexed microRNA are heavier than the free microRNA and can be seen in the wells. If complexing is less extensive, free microRNA migrate towards another position.

The amount of A3 premix formulation required to obtain a quantitative yield of microRNA was optimised.

In practice the negative charges provided by the microRNA are offset by the positive charges of the premix formulation (i.e. the positive charges of the cationic surfactant DOTAP). Typically, when the sole cationic surfactant of the premix formulation is DOTAP (which only comprises a single positive charge) a quantitative yield of complexing is obtained when the ratio between amount of positive charges due to the cationic surfactant in the «premix» formulation and amount of negative charges provided by the microRNA (N/P ratio) is greater than 8:1, as previously with the siRNA.

FIG. 9 shows an electrophoresis gel with UV detection after complexing microRNA with formulation A3 at the concentrations specified in Table 9, by mixing a solution of microRNA and the A3 premix formulation in 5 mM HEPES buffer. Before depositing on 1.5% agarose gel, 2 µL of loading buffer were added to the tests. After 1 h30 electrophoresis at 100 V, the gel was immersed in GelRed 3×. Finally UV detection was carried out.

TABLE 9

| ratio between amount of positive charges due to the cationic surfactant in the <<premix>> formulation and amount of negative charges provided by microRNA | 1:1 | 2:1 | 4:1 | 6:1 | 8:1 | 10 1 | 12:1 | 16:1 |
|---|---|---|---|---|---|---|---|---|
| Concentration of microRNA (µg/mL) | | | | 25 | | | | |
| Concentration of DOTAP (µg/mL) | 0 | 25 | 50 | 100 | 150 | 200 | 250 | 300 | 400 |

FIG. 9 shows that for a ratio value between amount of positive charges due to the cationic surfactant in the «premix» formulation and amount of negative charges provided by microRNA higher than 8:1, there are no longer any free microRNA remaining in the medium and that the microRNA has been fully complexed, as illustrated in FIGS. 2 and 3 with siRNA.

1.5. Complexation with Single DNA Tags

Complexation consists in a simple mixing of the formulations prepared above and of an siRNA solution, the whole in a buffer. The selection of the buffer depends on the envisioned application: for a study in vitro, the optimized culture medium for transfection steps, OptiMEM, was used. For a complexation study, Hepes buffer 5 mM was used. The mixture is stirred for at least 30 minutes at 600 rpm, this at room temperature (about 25° C.).

1.6. Encapsulation of the Fluorophore

The encapsulation of the fluorophore is achieved according to the method defined in application WO2008104717. More specifically, the fluorescent nanoparticles are obtained by sonication of the oily phase in the aqueous phase. The oily phase comprises a mixture of soya oil and of Suppocire® NC as well as lecithin and fluorophores (for solubility reasons). The aqueous phase as for it comprises the pegylated surfactant, the aqueous solution (NaCl or PBS) and optionally glycerol in order to increase the viscosity of the mixture. The fluorescent nanoparticles are produced by batches of 2 or 5 mL. Briefly, the oily phase is prepared by mixing the soya oil, Suppocire® NC and lecithin (dispersed phase+lecithin). An organic solvent (dichloromethane) is added in order to facilitate dissolution of lecithin. Once all the compounds are dissolved, the solvent is evaporated in vacuo at a temperature above the boiling point of the wax. The fluorescent molecules are then added into the oily phase. In order to facilitate their dispersion, the fluorophores are dissolved beforehand in an organic solvent (ethanol). The solution is homogenized and the organic solvent is removed by evaporation in vacuo. The aqueous phase is prepared by hot mixing of glycerol, of the pegylated surfactant and of the aqueous phase. Both phases maintained beforehand at about 50° C. are mixed and then homogenized with ultrasound, so as to form nanoparticles trapping in their cores the lipophilic fluorophores. The solutions of fluorescent nanoparticles obtained are then purified by dialysis so as to remove the molecules which possibly have not been encapsulated.

1.7. Preparation of a Library of Nanoparticles

The preparation of 1000 fluorescent nanoparticles is carried out by using siRNAs from the collection of 1292 siRNAs from Qiagen targeting 646 kinases (Human Kinase siRNA set V1.0; Ref. 1027091), or the collection of 2375 siRNAs from Qiagen targeting 1183 genes involved in cancers (Human Cancer siRNA set V2.0), or the collection of 278 siRNAs targeting 139 genes involved in cancers (Human Cancer siRNA set V1.0; Ref. 1022171), or the collection of 91,800 siRNAs from Qiagen targeting 22,950 human genes (Human Genome Wide siRNA set), or by using LNAs from the collection of 982 LNAs from Exiqon targeting all the known human miRNAs (miRCURY LNA Human microRNA Inhibitor Library; Ref. 190102-2).

The single DNA tag contains two sequences of 50 bp in 5' and in 3' allowing amplification of the tag flanking a single sequence of 10 bp containing synthetic bases. Each siRNA or each LNA of the collections is associated in silico with a single sequence of 10 bp.

Example 2: 2D and 3D Cultivation of Prostate Cells

The following prostate cells are used:
PTN1 and RWPE1 cells, which are immortalized normal epithelial cells of the prostate,
the cells WPE1-NA22, WPE1-NB14, WPE1-NB11 and WPE1-NB26, which are derived from RWPE1 cells and which mimic different tumorigenesis stages after exposure to N-methyl-N-nitrosourea,
the cell line 22Rv1, which is a line of human prostate carcinoma epithelial cells responding to a deficiency of androgens,
the cell lines VcaP and LNCaP, which are metastatic prostate cancer cell lines in vitro and in vivo sensitive to androgens,
the cell lines PC3 and DU145, which are metastatic prostate cancer cell lines which no longer respond to androgen deficiency,
primary prostate cells from healthy subjects.

The 3D structure production in the form of acini from these prostate cells is also achieved.

The transfection efficiency and the toxicity of the nanoparticles comprising a fluorophore, an siRNA and a single DNA tag are evaluated on each of these prostate cell cultures.

Example 3: Deconvolution of the Single DNA Tag, Analysis of the Data and Validation A small aliquot of cells selected after flow cytometry is used for identifying the single DNA tag. The DNA is extracted from fluorescent cells, subject to PCR with universal primers, and sequenced with a second generation sequencer (Illumina or Roche 454 or ABI solid). The identification of the sequence of 10 bp of the single DNA tag is then correlated with the siRNA or the LNA which has been associated with it in silico. A list of genes for which inhibition by siRNA or LNA induces the phenotype of interest is then established. The screening method also allows the establishment of sets of functional genomic data for each of the cell lines tested according to their sensitivity to hormonal therapies, lists of genes coding for proteins or miRNAs which are potential markers of sensitivity to hormones.

A validation in vitro on the remaining cells of the occurrence of the phenotype and of the inhibition of the gene is achieved by quantitative real time PCR and by Western-blot.

Example 4: Validations In Vivo and Clinical Validations

A validation strategy in two phases is achieved:
for validation in vivo, control human prostate cancer cells and prostate cancer cells transfected with the nanoparticles according to the invention (e.g. containing siRNAs or LNAs) are implanted in "nude" athymic cells. The volume of tumours is monitored and after euthanasia, the tumours are excised and fixed for immunohistological analysis of the proliferation or apoptosis in cells transformed with the nanoparticles according to the invention.
for clinical validation, commercial microchips of prostate tissues containing several hundred prostate cancer tissues of different grades are used.

This allows validation of biomarkers for prostate cancer, new therapeutic targets and siRNA as new therapeutic agents.

Example 5: Co-Delivery of siRNA of Interest and of a DNA Tag (Bar Code) by Fluorescent Nanoparticles, Sorting of the Cells Having Incorporated the Nanoparticles According to a Phenotype of Interest and a Posteriori Identification of the Bar Code of the DNA Tag by Extracting DNA and Specific Amplification from the Sorted Cells 5.1. Complexation Between Different Nucleic Acids, Tag DNA and siRNA, with a Formulation of Fluorescent Nanoparticles In this example, co-transfection of the target cells is carried out with an siRNA of interest and a specific DNA tag of the siRNA by resorting to dispersion of fluorescent nanoparticles.

Gel Delay Experiment (FIG. 9):

The formulations of lipid nanoparticles used in this example were achieved according to the same manufacturing method as the one described in Example 1 and corresponds to the formulation A3. The general complexation procedure is the same as the one followed for example 1. Briefly, complexation consists in simply mixing a formulation A3 comprising a lipophilic fluorophore encapsulated in the core (DiD, Invitrogen, Ref. D7757) and of a siRNA and DNA tag solution with nanoparticles, the whole in a buffer. In this study, the buffer used is HEPES (5 mM, pH 7.2). For the well 1, the nanoparticles A3 were complexed with a solution containing 11 ng of siRNA (siAllStar Negative Control siRNA, Qiagen, Ref. 1027280) and 20 ng of DNA tag (Eurogentec). For the following wells (wells numbered from 2 to 7), this siRNA/DNA tag solution was diluted by a factor two before complexation with the nanoparticles, according to the cascade dilution technique. The N/P ratios used here (N=positive charge brought by the ammonium group of the nitrogen of the cationic lipids making up the crown of the lipid particle; P=negative charge brought by the phosphate group of the nucleic acids) are 12/1, 24/1, 48/1, 96/1, 192/1, 384/1, 768/1 for the wells 1 to 7 respectively. The mixture was stirred for 30 minutes at 600 rpm at room temperature (about 25° C.). An electrophoresis on agarose gel (gel with 1.5% of agarose with Agarose ultrapure 1000, Invitrogen, Ref. 16550100; buffer TBE 10×, Ref. 15581044; ultrapure water, Ref. 10977035) gives the possibility of demonstrating that both nucleic acids are actually complexed at the fluorescent lipid droplet, as illustrated in FIG. 10. Indeed, if the nanoparticles/siRNA/DNA tag complexes are stable, all the nucleic acids (siRNA and DNA tag) are retained in the wells (wells 1 to 7) and cannot migrate within the gel. Conversely, a free siRNA (not complexed with the nanoparticles) will be visible in the form of a band migrating towards 21 bp (well 8). Also, a free DNA tag (non-complexed with the nanoparticles) will migrate in the form of a visible band towards 129 bp (well 9). This experiment shows the efficiency of the lipid nanoparticles, of the type Lipidot® of formulation A3, to be simultaneously and in a stable way for complexing the siRNAs and the DNA tags.

5.2. Co-Transfection of Two Nucleic Acids, siRNA and DNA Tag, by Fluorescent Nanoparticles A Transfection Experiment In Vitro of HeLa Over Expressing GFP with Formulation A3/DNA Tag/siRNA Complexes:

Simultaneous delivery, in target cells in vitro, of the different molecules transported by the lipid nanoparticle (formulation A3) containing a fluorophore was evaluated.

To do this, a study was conducted on HeLa cells, i.e., cells stemming from uterine cervix cancer (ATCC, Ref. HeLa-CCL2), which were modified in order to over express the GFP protein. Active delivery of siRNA is validated by extinction of the GFP protein (decrease in the FITC signal) by specific screening of its mRNA by an siGFP. In parallel, the observation of the interaction of the fluorescent nanoparticles with the cell is made possible by studying the time dependent change of the fluorescent signal brought by the encapsulated fluorophore, DID (followed by the APC signal). This first step shows a very strong decrease in the FITC signal and therefore of the expression of GFP in cells treated with the nanoparticle A3/DNA tag/siGFP complex as well as an increase in the APC signal indicating the interaction of the fluorescent nanoparticles (bearing the fluorophore DID) with the cells (FIGS. 11 and 12).

These results show that the presence of tag DNA does not perturb the delivery of siRNA in the cells and that the functionality of the latter is preserved, i.e., the interaction with the mRNA coding for GFP and inhibition of the expression of this protein by an RNA interfering mechanism. The efficiency of extinction of FITC fluorescence corresponding to the expression of GFP is of the order of 70% in these experiments following incubation of the cells with the fluorescent nanoparticle A3/DNA tag/siRNA targeted against mRNA of GFP complexes (FIG. 11).

Identification of the DNA Tag in the Sorted Cells on the Basis of GFP Extinction after Transfection by A3/DNA Tag/siRNA Complexes:

In this experiment, the cell populations strongly or weakly expressed in GFP were sorted by flow cytometry (Cytomation, MoFlo). In practice, 200,000 HeLa-GFP cells were sown in wells of 6-well plates. After 24 hours of cultivation, these cells were transfected with fluorescent nanoparticles A3/DNA tag/siAllStar complexes or fluorescent nanoparticles A3/DNA tag/siGFP complexes. Seventy two hours after transfection, the cells are detached from the wells by adding trypsin. The cells contained in three wells for a same transfection condition are added and sorted into two distinct populations, according to their strong or weak expression level of GFP (FIG. 13). The DNA content of the thereby recovered cells is extracted via the QiaAmp DNA mini kit (Qiagen, Ref. 51304) and then a PCR is carried out by using the specific primers of the DNA tag. The primers used for this amplification are the pGEX 3' and 5' primers (Eurogentec, Ref. UN-PR130-005 and UN-PR135-005). The PCR is carried out with 35 amplification cycles (Qiagen, HotStar-Taq Master Mix, Ref. 203443). The thereby amplified nucleic acids are then deposited in the wells of a 2% agarose gel prepared beforehand. In FIG. 14, we may observe that the cells transfected with the fluorescent nanoparticles A3/DNA tag/siGFP complexes have a very strong decrease in the expression of GFP, and also bear the DNA tag which is detected by PCR. This result shows the capability of the fluorescent nanoparticles of formulation A3 of simultaneously delivering within the cells, a DNA tag and a functional siRNA.

These results demonstrate:
  that the nanoparticles according to the invention allow simultaneous delivery in target cells of two nucleic acids (siRNA and DNA tag), the cells transfected by siRNA being therefore fluorescent.
  the feasibility of the sorting of the cells having incorporated the fluorescent nanoparticles and having a phenotype of interest,
  the feasibility of a posteriori identification of the siRNA of interest by analysing the bar code of the DNA tag specifically associated with this siRNA, after extraction of cell DNA and amplification of the tag DNA.

Example 6: Transfecting a Three-Dimensional Culture of PC3-GFP Cells in Matrigel 6.1. Seeding of PC3-GFP Cells in the Matrigel On Day 1, about 150 µL of Matrigel (Matrigel, BD Biosciences, reference 356231) 8% diluted in the complete culture medium (RPMI 1640 Glutamax (ref 61870-010, Life Technologies SAS, Invitrogen Division)) at 4° C., is poured into Lab-Tek Chamber Slides (4 wells, Ref 154526). After 30 min at 37° C., the time that the matrigel solidifies, about 7000 times PC3-GFP cells in 200 µl of medium are added to each well. Again, after 30 min at 37° C., the time that the cells enter the matrigel, 300 µL of Matrigel 8% (diluted in the culture medium) are added. Thus, the cells are completely immersed in the matrigel.

Every two days, the culture medium is changed.

At Day 4, spheroids are obtained and it is proceeded to the step of transfection with lipid nanoparticles ("Lipidots"-siGFP) or the control (Oligofectamine™-siGFP).

At Day 7: matrigel is lysed with Cell Recovery (VWR—ref: 734-0107) and trypsin for 40 min at 4° C. Then the cells are centrifuged and resuspended in PBS for analysis by FACS.

6.2. Transfection of siGFP with Oligofectamine™

Oligofectamine™ (ref 12252-011, Life Technologies SAS, Invitrogen Division), a commercial transfection agent, is used at dilutions from 0.4 to 6.4% (Oligofectamine™ volume/matrigel culture volume), for a fixed concentration siRNA (100 nM siGFP, Qiagen, ref 1022064).

The results obtained are shown in FIGS. 16-18. FIGS. 16 and 17 show a decrease in fluorescence measured for PC3-GFP cells contacted with Oligofectamine™-siGFP, indicating an inhibition of the expression of the protein. FIG. 18 compares the level of fluorescence inhibition induced by Oligofectamine™-siGFP compared to the control (non-transfected PC3-GFP cells). It is observed that the efficiency of the inhibition of GFP activity with Oligofectamine™ does not exceed 30%, regardless of the concentration of commercial agent used.

By comparison, siGFP transfected into PC3 cells expressing GFP (PC3-GFP cells) using Lipofectamine™, a commercial transfection agent known to be less effective Oligofectamine™ inhibited by 88.6% the activity of GFP in the cells in 2D culture.

The transfection efficiency of siRNA using Oligofectamine™ is therefore very significantly reduced when the cells were cultured in 3D.

6.3 Transfection of siGFP with the Formulation in the Nanoemulsion Form (Lipidots)

The formulation "B10" of example 1 (table 4), with or without encapsulated DiD (1,1'-dioctadecyl-3,3,3',3'-tetramethylindodicarbocyanine perchlorate) fluorophore, hereinafter called "Lipidots", was used for transfection.

For incorporation of siGFP, the following general procedure was followed: the complexation step consists in a simple mixture of the formulations in nanoemulsion form prepared above, such as formulation B10, and a solution of siRNA, in a buffer. The choice of the buffer is dependent on the envisaged application: for in vitro study, the OptiMEM® culture medium (ref 11058-021, Life Technologies SAS, Invitrogen Division), optimized for the transfection, was used.

100 mM of siRNA (GFP-22 siRNA rhodamine (catalog No. 1022176) (Qiagen) or siGFP (Sigma)) was used.

The mixture was stirred for 30 minutes at 600 rpm, at room temperature (about 25° C.).

The siGFP has been incorporated into the lipid nanoparticles at different N/P ratios, of 19/1 to 95/1, where N corresponds to the ammonium of the cationic lipid of the lipid nanoparticle and P denotes the phosphate of the nucleic acid, with a fixed concentration of 100 nM siRNA.

FIGS. 19 to 21 show that the effectiveness of inhibition of the GFP is dependent upon the cationic lipid concentration of the lipid nanoparticle. FIG. 21 shows in particular that it is possible to achieve a level of inhibition of the GFP fluorescence of about 80% in 3D culture, with the adequate relative concentrations of siRNA and nanoparticles. Hence in 3D culture, GFP inhibition is as efficient as in 2D culture.

Moreover, all the cells are positive for the presence of perchlorate, 1,1 dioctadecyl-3,3,3',3'-tétraméthylindodicarbocyanine (DiD)—and therefore to the presence of nanoparticle—and more than 70% of the cells become negative for GFP.

Altogether, transfection in 3D culture is more efficient with lipid nanoparticles than with the commercial transfection agent, Oligofectamine™.

Example 7: Transfection Tests with Medium Change at D+1 Following Transfection to Reduce the Potential Toxicity The experiments conducted in example 7 were reproduced, with a contacting of the cells with the formulation for 24 hours, followed by a change of the culture medium. Results shown in FIGS. 22-24 show that the particles still remain effective even in these conditions.

Example 8: Reduction in siGFP Concentration

The effect of a decrease in the concentration of siGFP on inhibition of GFP expression by PC3-GFP cells was assessed. The results shown in FIGS. 25-27 indicate that the concentration of siGFP can be reduced down to 20 nM without losing efficiency of inhibition of GFP expression (here, 50%). It is noted that for a N/P ratio=80/1, 100 nM of siGFP or N/P ratio=400/1 to 20 nM of siGFP the DOTAP lipid concentration in the nanoparticles is the same, with a concentration of DOTAP about 200 μg/mL. For the transfection efficiency, the key is ultimately not the value of N/P ratio, but rather the amount of lipid nanoparticles placed in contact with the cells.

What is claimed is:

1. A method for in vitro or ex vivo transfection of a nucleic acid into a eukaryotic cell in a 3D scaffold, said method comprising:
    a) providing eukaryotic cells in a 3D scaffold;
    b) contacting the eukaryotic cells in the 3D scaffold with at least one formulation in nanoemulsion form, under conditions sufficient to allow a nucleic acid and which is contained in said formulation in nanoemulsion form to transfect the eukaryotic cells in the 3D scaffold,
    wherein said at least one formulation in nanoemulsion form comprises a continuous aqueous phase and a least one dispersed phase, and further comprises:
    i) at least 5 mole % of amphiphilic lipid;
    ii) 15 to 70 mole % of at least one cationic surfactant comprising:
        ii-1) at least one lipophilic group selected from the group consisting of:
            an R or R—(C═O)— group, where R is a linear hydrocarbon chain having 11 to 23 carbon atoms,
            an ester or amide of fatty acids having 12 to 24 carbon atoms and phosphatidylethanolamine, and
            a poly(propylene oxide), and
        ii-2) at least one hydrophilic group comprising at least one cationic group selected from the group consisting of:
            a linear or branched alkyl group having 1 to 12 carbon atoms and interrupted and/or substituted by at least one cationic group; and
            a hydrophilic polymeric group comprising at least one cationic group; and
    iii) 10% to 55 mole % of a co-surfactant comprising at least one poly(ethylene oxide) chain comprising at least 25 ethylene oxide units;
    iv) a solubilising lipid; and
    v) said nucleic acid;
    wherein the mole percentages of amphiphilic lipid, cationic surfactant and co-surfactant are relative to the whole (amphiphilic lipid/cationic surfactant/co-surfactant/optional helper lipid); and
    wherein the solubilising lipid is solid at 20° C.

2. The method according to claim 1, wherein said at least one formulation in nanoemulsion form further comprises:
    vi) a helper lipid.

3. The method according to claim 2, wherein said helper lipid in the formulation is 1,2-Dioleoyl-sn-Glycero-3-Phosphoethanolamine.

4. The method according to claim 1, wherein the amphiphilic lipid is a phospholipid.

5. The method according to claim 1, wherein the cationic surfactant is selected from the group consisting of:
- N[1-(2,3-dioléyloxy) propyl]-N,N,N-trimethylammonium,
- 1,2-dioleyl-3-trimethylamonium-propane,
- N-(2-hydroxyethyl)-N,N-dimethyl-2,3-bis(tetradecyloxy-1-propananium),
- 1-[2-(oleoyloxy)ethyl]-2-oleyl-3-(2-hydroxyethyl)imidazolinium, and
- dioctadecylamidoglycylspermine.

6. The method according to claim 1, wherein said nucleic acid is a DNA sequence comprising a cDNA sequence or antisense sequence.

7. The method according to claim 1, wherein said nucleic acid consists in a mRNA sequence.

8. The method according to claim 1, wherein said nucleic acid is a nucleic acid which modulates endogenous mechanisms of RNA interference is selected from the group consisting of:
- small interfering RNA (siRNA);
- locked nucleic acid;
- microRNA (miRNA);
- a long double-stranded RNA (dsRNA);
- PIWI-interacting RNAs (piRNA); and
- small hairpin RNA (shRNA).

9. The method according to claim 8, wherein said nucleic acid which modulates endogenous mechanisms of RNA interference is a siRNA.

10. The method according to claim 1, wherein said formulation in nanoemulsion form further comprises a DNA tag.

11. The method according to claim 1, wherein in step b) the eukaryotic cells in 3D scaffold are contacted with a plurality of formulations in nanoemulsion form, each formulation in nanoemulsion form comprising:
- a different nucleic acid,
- a tracer, and
- a single DNA tag specific to said nucleic acid,
- thereby forming a library of formulations in nanoemulsion form containing a nucleic acid.

12. The method according to claim 11, wherein said single DNA tag consists in a sequence of DNA with at least 50 nucleotides or base pairs (bp) consisting in, on a strand or in the 5'-3' sense:
- a first sequence of at least 20 nucleotides common to all the single DNA tags of the library, fused to
- a single sequence of at least 10 nucleotides specific to said nucleic acid, which is fused to
- a second sequence of at least 20 nucleotides common to all the single DNA tags of the library.

13. The method according to claim 1, wherein said eukaryotic cells in 3D scaffold are eukaryotic cells cultivated in and/or on a three-dimensional biocompatible polymeric matrix.

14. The method according to claim 13, wherein said biocompatible polymeric matrix is a hydrogel.

15. The method according to claim 1, wherein said eukaryotic cells in 3D scaffold consist of a biological sample comprising eukaryotic cells embedded in extracellular matrix.

16. A method for in vitro or ex vivo transfection of a nucleic acid into a eukaryotic cell in a 3D scaffold, said method comprising:
a) providing eukaryotic cells in a 3D scaffold;
b) contacting the eukaryotic cells in the 3D scaffold with at least one formulation in nanoemulsion form, under conditions sufficient to allow a nucleic acid and which is contained in said formulation in nanoemulsion form to transfect the eukaryotic cells in the 3D scaffold,
wherein said at least one formulation in nanoemulsion form comprises a continuous aqueous phase and a least one dispersed phase, and further comprises:
i) at least 5 mole % of amphiphilic lipid;
ii) 15 to 70 mole % of at least one cationic surfactant comprising:
 ii-1) at least one lipophilic group selected from the group consisting of:
  an R or R—(C=O)— group, where R is a linear hydrocarbon chain having 11 to 23 carbon atoms,
  an ester or amide of fatty acids having 12 to 24 carbon atoms and phosphatidylethanolamine, and
  a poly(propylene oxide), and
 ii-2) at least one hydrophilic group comprising at least one cationic group selected from the group consisting of:
  a linear or branched alkyl group having 1 to 12 carbon atoms and interrupted and/or substituted by at least one cationic group; and
  a hydrophilic polymeric group comprising at least one cationic group; and
iii) 10% to 55 mole % of a co-surfactant comprising at least one poly(ethylene oxide) chain comprising at least 25 ethylene oxide units;
iv) a solubilising lipid; and
v) said nucleic acid;
wherein the mole percentages of amphiphilic lipid, cationic surfactant and co-surfactant are relative to the whole (amphiphilic lipid/cationic surfactant/co-surfactant/optional helper lipid); and
wherein the solubilising lipid is a glyceride of saturated fatty acids.

* * * * *